US011877861B2

(12) United States Patent
Heneghan et al.

(10) Patent No.: US 11,877,861 B2
(45) Date of Patent: *Jan. 23, 2024

(54) METHODS AND SYSTEMS FOR LABELING SLEEP STATES

(71) Applicant: Fitbit, Inc., San Francisco, CA (US)

(72) Inventors: Conor Joseph Heneghan, Campbell, CA (US); Jacob Anthony Arnold, Fremont, CA (US); Zachary Todd Beattie, Pleasant Hill, CA (US); Alexandros A. Pantelopoulos, Berkeley, CA (US); Allison Maya Russell, Berkeley, CA (US); Philip Foeckler, Richmond, CA (US); Adrienne M. Tucker, Fremont, CA (US); Delisa Lopez, San Francisco, CA (US); Belen Lafon, San Francisco, CA (US); Atiyeh Ghoreyshi, San Francisco, CA (US)

(73) Assignee: FITBIT, INC., San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/690,369

(22) Filed: Mar. 9, 2022

(65) Prior Publication Data

US 2022/0265208 A1 Aug. 25, 2022

Related U.S. Application Data

(63) Continuation of application No. 17/560,639, filed on Dec. 23, 2021, now abandoned, which is a
(Continued)

(51) Int. Cl.
*A61B 5/00* (2006.01)
*A61B 5/024* (2006.01)
*A61B 5/11* (2006.01)

(52) U.S. Cl.
CPC ........ *A61B 5/4812* (2013.01); *A61B 5/02416* (2013.01); *A61B 5/02438* (2013.01);
(Continued)

(58) Field of Classification Search
None
See application file for complete search history.

(56) References Cited

U.S. PATENT DOCUMENTS 4,836,219 A 6/1989 Hobson
5,724,990 A 3/1998 Ogino
(Continued)

FOREIGN PATENT DOCUMENTS

CN 103717125 4/2014
CN 103919536 7/2014
(Continued)

OTHER PUBLICATIONS

U.S. Appl. No. 16/442,304, filed Jun. 14, 2019, Arnold et al.
(Continued)

*Primary Examiner* — Benjamin S Melhus
(74) *Attorney, Agent, or Firm* — Dority & Manning, P.A.

(57) ABSTRACT

A system, computer-readable storage medium, and a method capable of, directly or indirectly, estimating sleep states of a user based on sensor data from movement sensors and/or optical sensors.

19 Claims, 29 Drawing Sheets

Related U.S. Application Data continuation of application No. 15/438,643, filed on Feb. 21, 2017, now Pat. No. 11,207,021.

(60) Provisional application No. 62/384,188, filed on Sep. 6, 2016.

(52) U.S. Cl.
CPC ............... *A61B 5/11* (2013.01); *A61B 5/1114* (2013.01); *A61B 5/681* (2013.01); *A61B 5/7264* (2013.01); *A61B 5/7267* (2013.01); *A61B 5/743* (2013.01); *A61B 2562/0219* (2013.01)

(56) References Cited

U.S. PATENT DOCUMENTS

| | | | |
|---|---|---|---|
| 5,902,250 A | 5/1999 | Verrier | |
| 6,964,641 B2 | 11/2005 | Cho | |
| 7,306,567 B2 | 12/2007 | Loree, IV | |
| 7,578,793 B2 | 8/2009 | Tadros | |
| 7,674,230 B2 | 3/2010 | Reisfeld | |
| 8,002,553 B2 | 8/2011 | Hatlestad | |
| 8,273,035 B2 | 9/2012 | Russo | |
| 8,292,819 B2 | 10/2012 | Kuo | |
| 8,548,770 B2 | 10/2013 | Yuen | |
| 8,606,356 B2 | 12/2013 | Lee | |
| 8,684,900 B2 | 4/2014 | Tran | |
| 8,690,751 B2 | 4/2014 | Auphan | |
| 8,712,723 B1 | 4/2014 | Kahn | |
| 8,764,651 B2 | 7/2014 | Tran | |
| 8,793,522 B2 | 7/2014 | Rahman | |
| 8,812,259 B2 | 8/2014 | Messenger | |
| 8,942,779 B2 | 1/2015 | Halperin | |
| 9,675,281 B2 | 6/2017 | Arnold | |
| 9,808,185 B2 | 11/2017 | Arnold | |
| 9,820,680 B2 | 11/2017 | Muzet | |
| 10,092,219 B2 | 10/2018 | Arnold | |
| 10,311,745 B2 | 6/2019 | Arnold | |
| 10,325,514 B2 | 6/2019 | Arnold | |
| 2004/0087878 A1 | 5/2004 | Krausman et al. | |
| 2005/0043652 A1 | 2/2005 | Lovett et al. | |
| 2005/0113650 A1 | 5/2005 | Pacione et al. | |
| 2005/0190065 A1 | 9/2005 | Ronnholm | |
| 2005/0209511 A1 | 9/2005 | Heruth et al. | |
| 2005/0209512 A1 | 9/2005 | Heruth et al. | |
| 2006/0020177 A1 | 1/2006 | Seo et al. | |
| 2006/0031102 A1 | 2/2006 | Teller et al. | |
| 2006/0184056 A1 | 8/2006 | de Chazal et al. | |
| 2006/0224051 A1 | 10/2006 | Teller et al. | |
| 2006/0241359 A1 | 10/2006 | Nagai et al. | |
| 2006/0281978 A1 | 12/2006 | Crucilla | |
| 2007/0161873 A1 | 7/2007 | Ni et al. | |
| 2007/0191742 A1 | 8/2007 | Park | |
| 2007/0208233 A1 | 9/2007 | Kovacs | |
| 2008/0287751 A1 | 11/2008 | Stivoric et al. | |
| 2008/0306351 A1 | 12/2008 | Izumi | |
| 2009/0164219 A1 | 6/2009 | Yeung et al. | |
| 2009/0203972 A1 | 8/2009 | Heneghan et al. | |
| 2009/0292215 A1 | 11/2009 | Todros et al. | |
| 2010/0056907 A1 | 3/2010 | Rappaport et al. | |
| 2010/0099954 A1 | 4/2010 | Dickinson et al. | |
| 2010/0102130 A1 | 4/2010 | Madej et al. | |
| 2010/0125215 A1 | 5/2010 | Kuo et al. | |
| 2010/0295684 A1 | 11/2010 | Hsieh et al. | |
| 2011/0015495 A1 | 1/2011 | Dothie et al. | |
| 2011/0124979 A1 | 5/2011 | Heneghan et al. | |
| 2011/0230790 A1 | 9/2011 | Kozlov | |
| 2011/0252684 A1 | 10/2011 | Ufer et al. | |
| 2011/0295083 A1 | 12/2011 | Doelling et al. | |
| 2012/0316455 A1 | 2/2012 | Rahman et al. | |
| 2012/0253220 A1 | 4/2012 | Rai et al. | |
| 2012/0142443 A1 | 6/2012 | Savarese et al. | |
| 2012/0316471 A1 | 12/2012 | Rahman et al. | |
| 2013/0006124 A1 | 1/2013 | Eyal et al. | |
| 2013/0018284 A1 | 1/2013 | Kahn et al. | |
| 2013/0096843 A1 | 4/2013 | Yuen et al. | |
| 2013/0338446 A1 | 12/2013 | Van Vugt et al. | |
| 2014/0058703 A1 | 2/2014 | Kimishima et al. | |
| 2014/0073486 A1 | 3/2014 | Ahmed et al. | |
| 2014/0088373 A1 | 3/2014 | Phillips et al. | |
| 2014/0088378 A1 | 3/2014 | Muzet | |
| 2014/0089243 A1 | 3/2014 | Oppenheimer | |
| 2014/0135594 A1 | 5/2014 | Yuen et al. | |
| 2014/0172362 A1 | 6/2014 | Burton et al. | |
| 2014/0176422 A1 | 6/2014 | Brumback et al. | |
| 2014/0176475 A1 | 6/2014 | Myers et al. | |
| 2014/0180022 A1 | 6/2014 | Stivoric et al. | |
| 2014/0200474 A1 | 7/2014 | Selvaraj et al. | |
| 2014/0221850 A1 | 8/2014 | Farringdon et al. | |
| 2014/0275854 A1 | 9/2014 | Venkatraman et al. | |
| 2014/0316305 A1 | 10/2014 | Venkatraman et al. | |
| 2014/0316584 A1 | 10/2014 | Matsuoka et al. | |
| 2014/0347366 A1 | 11/2014 | Emori et al. | |
| 2014/0364770 A1 | 12/2014 | Slonneger et al. | |
| 2015/0026647 A1 | 1/2015 | Park et al. | |
| 2015/0057967 A1 | 2/2015 | Albinali | |
| 2015/0112155 A1 | 4/2015 | Bijjani et al. | |
| 2015/0112158 A1 | 4/2015 | He et al. | |
| 2015/0119741 A1* | 4/2015 | Zigel | ................... A61B 5/0816 600/529 |
| 2015/0173671 A1 | 6/2015 | Paalasmaa et al. | |
| 2015/0190086 A1 | 7/2015 | Chan et al. | |
| 2015/0230750 A1 | 8/2015 | Mcdarby et al. | |
| 2015/0355612 A1 | 12/2015 | Franceschetti et al. | |
| 2016/0007934 A1 | 1/2016 | Arnold et al. | |
| 2016/0022175 A1 | 1/2016 | Arnold et al. | |
| 2016/0022201 A1 | 1/2016 | Arnold et al. | |
| 2016/0022203 A1 | 1/2016 | Arnold et al. | |
| 2016/0051184 A1 | 2/2016 | Wisbey et al. | |
| 2016/0066716 A1 | 3/2016 | Rao | |
| 2016/0151603 A1 | 6/2016 | Shouldice et al. | |
| 2016/0235344 A1 | 8/2016 | Auerbach | |
| 2016/0235359 A1 | 8/2016 | Cho et al. | |
| 2016/0246259 A1 | 8/2016 | Zhang | |
| 2016/0270718 A1 | 9/2016 | Heneghan et al. | |
| 2016/0278696 A1 | 9/2016 | Ishibashi et al. | |
| 2016/0374569 A1 | 12/2016 | Breslow et al. | |
| 2017/0055898 A1 | 3/2017 | Bandyopadhyay et al. | |
| 2017/0215808 A1 | 3/2017 | Bandyopadhyay et al. | |
| 2017/0312477 A1 | 11/2017 | Hashizaki et al. | |
| 2017/0347946 A1 | 12/2017 | Arnold et al. | |
| 2017/0347948 A1 | 12/2017 | Thein et al. | |
| 2017/0347949 A1 | 12/2017 | Arnold et al. | |
| 2017/0352287 A1 | 12/2017 | Arnold et al. | |
| 2017/0360361 A1 | 12/2017 | Long et al. | |
| 2017/0360363 A1 | 12/2017 | Fonseca et al. | |
| 2018/0106897 A1 | 4/2018 | Shouldice et al. | |
| 2018/0125418 A1 | 5/2018 | Haakma et al. | |
| 2019/0183414 A1 | 6/2019 | Ferreira dos Santos da Fonseca et al. | |
| 2019/0371197 A1 | 12/2019 | Arnold et al. | |
| 2020/0054289 A1 | 2/2020 | Shimol et al. | |

FOREIGN PATENT DOCUMENTS

| | | |
|---|---|---|
| CN | 104812300 | 7/2015 |
| CN | 105446480 | 3/2016 |
| WO | WO 2012/170586 | 2/2012 |
| WO | WO 2012/170924 | 2/2012 |
| WO | WO 2012/171032 | 2/2012 |
| WO | WO 2014/047310 | 3/2014 |
| WO | WO 2015/119726 | 8/2015 |
| WO | WO 2015/127067 | 8/2015 |
| WO | WO 2016/003269 | 1/2016 |
| WO | WO 2016/108751 | 7/2016 |
| WO | WO 2018/048951 | 3/2018 |

OTHER PUBLICATIONS

Chinese First Office Action, dated Nov. 1, 2019, in Application No. CN201910277917.9.

(56) References Cited

OTHER PUBLICATIONS

International Preliminary Report On Patentability—PCT/US17/50344—ISA/EPO—dated Mar. 21, 2019.
International Search Report and Written Opinion—PCT/US17/50344—ISA/EPO—dated Mar. 2, 2018.
Ribeiro, Pedro Ramiro Guimaraes, "Sensor based sleep patterns and nocturnal activity analysis," Faculdade de Engenharia da Universidade do Porto, Jul. 17, 2014, 38 pages.
U.S. Final Office Action, dated Aug. 30, 2016, issued in U.S. Appl. No. 14/877,920.
U.S. Final Office Action, dated Dec. 1, 2016, issued in U.S. Appl. No. 14/877,912.
U.S. Final Office Action, dated Jul. 28, 2017, issued in U.S. Appl. No. 15/199,113.
U.S. Final Office Action, dated Jul. 30, 2019, issued in U.S. Appl. No. 16/058,423.
U.S. Final Office Action, dated Jun. 15, 2017, issued in U.S. Appl. No. 15/171,049.
U.S. Final Office Action, dated Jun. 21, 2017, issued in U.S. Appl. No. 15/192,455.
U.S. Final Office Action, dated Nov. 16, 2016, issued in U.S. Appl. No. 14/877,922.
U.S. Notice of Allowance, dated Aug. 17, 2017, issued in U.S. Appl. No. 14/859,192.
U.S. Notice of Allowance, dated Dec. 31, 2018, issued in U.S. Appl. No. 15/171,049.
U.S. Notice of Allowance, dated Dec. 31, 2018, issued in U.S. Appl. No. 15/192,455.
U.S. Notice of Allowance, dated Feb. 13, 2017, issued in U.S. Appl. No. 14/877,920.
U.S. Notice of Allowance, dated May 11, 2018, issued in U.S. Appl. No. 14/877,912.
U.S. Office Action, dated Apr. 18, 2016, issued in U.S. Appl. No. 14/877,912.
U.S. Office Action, dated Apr. 22, 2016, issued in U.S. Appl. No. 14/877,920.
U.S. Office Action, dated Dec. 15, 2016, issued in U.S. Appl. No. 15/171,049.
U.S. Office Action, dated Dec. 16, 2019, issued in U.S. Appl. No. 16/058,423.
U.S. Office Action, dated Dec. 28, 2016, issued in U.S. Appl. No. 15/199,113.
U.S. Office Action, dated Feb. 8, 2017, issued in U.S. Appl. No. 14/859,192.
U.S. Office Action, dated Jan. 25, 2018, issued in U.S. Appl. No. 14/877,912.
U.S. Office Action, dated Jul. 24, 2017, issued in U.S. Appl. No. 14/877,912.
U.S. Office Action, dated Jun. 1, 2016, issued in U.S. Appl. No. 14/877,922.
U.S. Office Action, dated Jun. 24, 2016, issued in U.S. Appl. No. 14/859,192.
U.S. Office Action, dated Mar. 11, 2019, issued in U.S. Appl. No. 16/058,423.
U.S. Office Action, dated May 14, 2018, issued in U.S. Appl. No. 15/192,455.
U.S. Office Action, dated May 3, 2018, issued in U.S. Appl. No. 15/171,049.
U.S. Office Action, dated Nov. 30, 2016, issued in U.S. Appl. No. 15/192,455.

* cited by examiner

METHODS AND SYSTEMS FOR LABELING SLEEP STATES

CROSS-REFERENCE TO RELATED APPLICATION

This application is a continuation application of U.S. patent application Ser. No. 17/560,639, filed Dec. 23, 2021, and titled "METHODS AND SYSTEMS FOR LABELING SLEEP STATES," which is a continuation application of U.S. patent application Ser. No. 15/438,643, filed Feb. 21, 2017, and titled "METHODS AND SYSTEMS FOR LABELING SLEEP STATES," which claims the benefit of priority under 35 U.S.C. § 119(e) to U.S. Provisional Patent Application No. 62/384,188, filed Sep. 6, 2016, and titled "METHODS AND SYSTEMS FOR LABELING SLEEP STATES," which is hereby incorporated by reference herein in its entirety.

TECHNICAL FIELD

The present disclosure relates to wearable devices. In particular, example devices described herein may be capable of, directly or indirectly, estimating sleep states of a user based on sensor data from movement sensors and/or optical sensors.

BACKGROUND

In conventional sleep stage scoring, an expert analyzes a readout of a sleeper's brain activity. This process is a highly manual process that involves expertise from the scorer. As such, by way of error or differences in approaches, sleep stage scores may vary across scorers and across sleepers. Moreover, such sleep stage scoring requires specialized equipment, such as an electroencephalography (EEG) system, which makes it difficult to perform outside of the laboratory setting.

SUMMARY

Details of one or more implementations of the subject matter described in this specification are set forth in the accompanying drawings and the description below. Other features, aspects, and advantages will become apparent from the description, the drawings, and the claims.

In some implementations, a sleep monitoring system is provided that includes a wearable electronic device to be worn by a user, the wearable electronic device including a set of one or more motion sensors to generate motion data that represent motion of the wearable electronic device over a first time window and a set of one or more optical sensors to generate cardiopulmonary pulse-related data detected by the wearable electronic device over the first time window. Such implementations may further include a set of one or more processors configured to receive data from the set of motion sensors and the set of one or more optical sensors and a non-transitory, machine-readable storage medium operatively coupled to the set of one or more processors and having stored therein instructions that, when executed, cause the set of one or more processors to: extract a movement feature from the motion data covering the first time window; extract a pulse data feature from the cardiopulmonary pulse-related data covering the first time window; and use the movement feature and the pulse data feature to cause a classifier to label a time period associated with the first time window with an identifier indicating a first sleep stage selected from a plurality of sleep stages.

In some additional implementations, the plurality of sleep stages may include two or more sleep stages drawn from sleep stages such as an awake sleep stage, an artefact/off-wrist sleep stage, a light sleep stage, a deep sleep stage, and a random eye movement (REM) sleep stage.

In some additional or alternative implementations, the set of one or more optical sensors may include a photoplethysmogram sensor, the set of one or more motion sensors may include an accelerometer, or the set of one or more optical sensors may include a photoplethysmogram sensor and the set of one or more motion sensors may include an accelerometer.

In some additional or alternative implementations, the first time window and the time period may be the same duration and have the same start point and end point.

In some additional or alternative implementations, the movement feature and the pulse data feature, collectively, may include one or more features such as: a cumulative movement index extracted from the motion data; a first elapsed time between a first time within the first time window and a second time before the first time window when the cumulative movement index last exceeded a first threshold amount; a second elapsed time between a third time within the first time window and a fourth time after the first time window when the cumulative movement index first exceeded a second threshold amount; a third elapsed time between a fifth time within the first time window and a closest time outside of the first time window when the cumulative movement index first exceeded a third threshold amount; a first number of time windows before the first time window since the cumulative movement index last exceeded a fourth threshold amount; a second number of time windows after the first time window until the cumulative movement index first exceeded a fifth threshold amount; a variability, as assessed by sample entropy, of inter-beat intervals in the cardiopulmonary pulse-related data; a variability, as assessed by sample entropy, of the cardiopulmonary pulse-related data; a root mean square of the successive differences of the inter-beat intervals; a root mean square of the successive differences of the cardiopulmonary pulse-related data; a low-frequency spectral power of the inter-beat intervals over the frequency range of 0.04 Hz to 0.15 Hz; a low-frequency spectral power of the cardiopulmonary pulse-related data over the frequency range of 0.04 Hz to 0.15 Hz; a high-frequency spectral power of the inter-beat intervals over the frequency range of 0.15 Hz to 0.4 Hz; a high-frequency spectral power of the cardiopulmonary pulse-related data over the frequency range of 0.15 Hz to 0.4 Hz; a variability of an envelope of the cardiopulmonary pulse-related data; a variability of an envelope of the inter-beat intervals; a variability of a de-trended respiration rate extracted from the cardiopulmonary pulse-related data; an inter-percentile spread of a heart rate extracted from the cardiopulmonary pulse-related data or from the inter-beat intervals; a normalized de-trended heart rate extracted from the cardiopulmonary pulse-related data or from the inter-beat intervals; and a cross-correlation of each pulse shape of one or more pulse shapes in the cardiopulmonary pulse-related data with a previous pulse shape in the cardiopulmonary pulse-related data (in which the pulse shapes may be normalized to a common duration prior to the cross-correlation).

In some additional or alternative implementations, the movement feature and the pulse data feature, collectively, may include at least one of: a time since a last movement, a time until next movement, a time from nearest movement, a variability, assessed using sample entropy, of inter-beat intervals extracted from the cardiopulmonary pulse-related data, a variability of a de-trended respiration rate extracted from the cardiopulmonary pulse-related data, and a cross-correlation of each pulse shape of one or more pulse shapes in the cardiopulmonary pulse-related data with a previous pulse shape in the cardiopulmonary pulse-related data (in which the pulse shapes may be normalized to a common duration prior to the cross-correlation).

In some additional or alternative implementations, the instructions that cause the classifier to label the time period may include instructions that, when executed, cause the set of one or more processors to transmit the movement feature and the pulse data feature to a server system executing the classifier, and at least some of the one or more processors in the set of one or more processors may be part of the server system.

In some additional or alternative implementations, the instructions that cause the classifier to label the time period may include instructions that, when executed, cause the set of one or more processors to execute a classifier such as, for example, a nearest neighbor classifier, a random forest classifier, or a linear discriminant classifier.

In some additional or alternative implementations, the classifier may be trained using movement features and pulse data features extracted from benchmark motion data and benchmark cardiopulmonary pulse-related data collected for a population of sleep study subjects.

In some additional or alternative implementations, the instructions may further cause the set of one or more processors to fill in missing data points in the cardiopulmonary pulse-related data prior to the one or more processors being caused to generate the pulse data feature.

In some additional or alternative implementations, the instructions may further cause the set of one or more processors to change the label for the time period associated with the first time window based on labels for a plurality of consecutive time periods, including the time period associated with the first time window, satisfying a pattern constraint.

In some additional implementations, the pattern constraint may be satisfied when the time period is labeled with an indicator indicating an awake sleep stage and time periods neighboring the time period are labeled with an indicator indicating a deep sleep stage. In such implementations, the label for the time period may be changed from the indicator indicating the awake sleep stage to the indicator indicating the deep sleep stage.

In some additional or alternative implementations, the instructions may further cause the set of one or more processors to: obtain confidence numbers associated with time period, each confidence number for a different one of the sleep stages in the plurality of sleep stages; and label the time period with an identifier indicating the sleep stage of the plurality of sleep stages having the highest confidence number for the time period.

In some implementations, a method may be provided that includes receiving cardiopulmonary pulse-related data obtained from a set of one or more optical sensors in a wearable electronic device over a first time window; receiving motion data obtained from a set of one or more motion sensors in the wearable electronic device over the first time window, the motion data including at least one of a quantification of movement experienced by the wearable electronic device or data derived therefrom; and labeling a time period associated with the first time window with an indicator indicating a first sleep stage selected from a plurality of sleep stages using the motion data and the cardiopulmonary pulse-related data.

In some additional implementations, the method may further include extracting a movement feature from the motion data covering the first time window; extracting a pulse data feature from the cardiopulmonary pulse-related data covering the first time window; and using the movement feature and the pulse data feature to cause a classifier to select the first sleep stage from the plurality of sleep stages.

In some additional or alternative implementations, the classifier may be a nearest neighbor classifier, a random forest classifier, or a linear discriminant classifier.

In some additional or alternative implementations, the method may further include filling in missing data points in the cardiopulmonary pulse-related data prior to extracting the pulse data feature.

In some additional or alternative implementations, the method may further include training the classifier using movement features and pulse data features extracted from benchmark motion data and benchmark cardiopulmonary pulse-related data collected for a population of sleep study subjects.

In some additional or alternative implementations, the movement feature and the pulse data feature, collectively, may include one or more features such as: a cumulative movement index extracted from the motion data; a first elapsed time between a first time within the first time window and a second time before the first time window when the cumulative movement index last exceeded a first threshold amount; a second elapsed time between a third time within the first time window and a fourth time after the first time window when the cumulative movement index first exceeded a second threshold amount; a third elapsed time between a fifth time within the first time window and a closest time outside of the first time window when the cumulative movement index first exceeded a third threshold amount; a first number of time windows before the first time window since the cumulative movement index last exceeded a fourth threshold amount; a second number of time windows after the first time window until the cumulative movement index first exceeded a fifth threshold amount; a variability, as assessed by sample entropy, of inter-beat intervals in the cardiopulmonary pulse-related data; a variability, as assessed by sample entropy, of the cardiopulmonary pulse-related data; a root mean square deviation of the inter-beat intervals; a root mean square deviation of the cardiopulmonary pulse-related data; a low-frequency spectral power of the inter-beat intervals; a high-frequency spectral power of the inter-beat intervals; a low-frequency spectral power of the cardiopulmonary pulse-related data; a high-frequency spectral power of the cardiopulmonary pulse-related data; a variability of an envelope of the cardiopulmonary pulse-related data; a variability of an envelope of the inter-beat intervals; a variability of a de-trended respiration rate extracted from the cardiopulmonary pulse-related data; an inter-percentile spread of a heart rate extracted from the cardiopulmonary pulse-related data or from the inter-beat intervals; a normalized de-trended heart rate extracted from the cardiopulmonary pulse-related data or from the inter-beat intervals; and a cross-correlation of each pulse shape of one or more pulse shapes in the cardiopulmonary pulse-related data with a previous pulse shape in the cardiopulmonary pulse-related data (in which the pulse shapes may be normalized to a common duration prior to the cross-correlation).

In some additional or alternative implementations, the first time window and the time period may be the same duration and have the same start point and end point.

In some additional or alternative implementations, the plurality of sleep stages may include two or more sleep stages drawn from sleep stages such as an awake sleep stage, an artefact/off-wrist sleep stage, a light sleep stage, a deep sleep stage, and a random eye movement (REM) sleep stage.

In some additional or alternative implementations, the time period may be one of a plurality of time periods, each labeled with an indicator indicating a corresponding sleep stage selected from the plurality of sleep stages, and the method may further include: detecting that the first sleep stage causes the sleep stages corresponding to each time period of the plurality of time periods to match a sleep stage rule, the sleep stage rule indicating a sequence of sleep stages that are invalid; and replacing, responsive to the detecting that the first sleep stage causes the sleep stages corresponding to each time period of the plurality of time periods to match the sleep stage rule, the first sleep stage with a second sleep stage according to an update rule.

In some additional or alternative implementations, the update rule may execute according to a majority rules analysis of the plurality of sleep stages to select the second sleep stage.

In some additional or alternative implementations, the labeled time period may be part of a plurality of labeled time periods, and the method may further include generating estimates for durations of sleep time for each type of label used in the plurality of labeled time periods.

In some implementations, an apparatus may be provided that includes a communications interface; one or more processors; and a memory. The one or more processors may be communicatively connected with the memory and the communications interface, and the memory may have computer-executable instructions stored therein that, when executed, cause the one or more processors to: receive sleep stage data for a first user, the sleep stage data including data indicating time intervals associated with a first sleep session of the first user and data indicating, for each time interval, a sleep stage associated with that time interval, in which the sleep stage associated with each time interval is selected from a predetermined set of different sleep stages; and generate a first graphical user interface component that indicates a relative percentile breakdown of total time spent in each of the sleep stages for the first sleep session.

In some additional implementations, the predetermined set of different sleep stages may include one or more sleep stages drawn from sleep stages such as an artefact or off-wrist sleep stage, an awake sleep stage, a random eye movement (REM) sleep stage, a light sleep stage, or a deep sleep stage.

In some additional or alternative implementations, the memory may further have computer-executable instructions stored therein that, when executed, further cause the one or more processors to: receive representative personal sleep stage data, the representative personal sleep stage data indicating a representative relative percentile breakdown of total time spent in each of the sleep stages for a plurality of sleep sessions of the first user; and modify the first graphical user interface component to also indicate the representative relative percentile breakdown of the total time spent in each of the sleep stages for the plurality of sleep sessions of the first user in addition to the relative percentile breakdown of the total time spent in each of the sleep stages for the first sleep session.

In some additional or alternative implementations, the representative personal sleep stage data indicating the representative relative percentile breakdown of the total time spent in each of the sleep stages for the plurality of sleep sessions of the first user may be a relative percentile breakdown of the averages of the total time spent in each of the sleep stages for the plurality of sleep sessions of the first user.

In some additional or alternative implementations, the plurality of sleep sessions of the first user may include a number of sleep sessions spanning at least a time interval such as, for example, a week prior to the time when the first graphical user interface component is generated, four weeks prior to the time when the first graphical user interface component is generated, 15 days prior to the time when the first graphical user interface component is generated, or 30 days prior to the time when the first graphical user interface component is generated.

In some additional or alternative implementations, the memory may further have computer-executable instructions stored therein that, when executed, further cause the one or more processors to: receive representative demographic sleep stage data, the representative demographic sleep stage data indicating a representative demographic relative percentile breakdown of total time spent in each of the sleep stages for a plurality of sleep sessions of a plurality of users; and modify the first graphical user interface component to also indicate the representative demographic relative percentile breakdown of the total time spent in each of the sleep stages for the plurality of sleep sessions of the plurality of users in addition to the relative percentile breakdown of the total time spent in each of the sleep stages for the first sleep session.

In some additional or alternative implementations, the representative demographic relative percentile breakdown of the total time spent in each of the sleep stages for the plurality of sleep sessions of the plurality of users may include percentile ranges associated with each of the sleep stages.

In some additional or alternative implementations, the plurality of users may be users within a first age range and may be the same gender as the first user, and the first user may be within the first age range.

In some implementations, an apparatus may be provided that includes a communications interface, one or more processors, and a memory. The one or more processors may be communicatively connected with the memory and the communications interface and the memory may have computer-executable instructions stored therein that, when executed, cause the one or more processors to: receive sleep stage data for a first user, the sleep stage data including data indicating time intervals associated with a first sleep session of the first user and data indicating, for each time interval, a sleep stage associated with that time interval, in which the sleep stage associated with each time interval may be selected from a predetermined set of different sleep stages; generate a first graphical user interface component that includes a hypnogram displaying the time intervals; receive a first user input; and modify, responsive to receiving the first user input, the first graphical user interface to accentuate the time intervals associated with a first sleep stage of the predetermined set of different sleep stages and to provide textual content that is customized based on the sleep stage data of the first user that pertains to the first sleep stage.

In some additional implementations, the predetermined set of different sleep stages may include at least one of an artefact or off-wrist sleep stage, an awake sleep stage, a random eye movement (REM) sleep stage, a light sleep stage, or a deep sleep stage.

In some additional or alternative implementations, the textual content that is customized based on the sleep stage data of the first user that pertains to the first sleep stage may include text such as text indicating a number of intervals in which the first user was in the first sleep stage during the sleep session and/or text indicating a percentile amount based on a total amount of time spent in the first sleep stage during the sleep session relative to a total amount of time spent in all of the sleep stages of the predetermined set of different sleep stages during the sleep session.

In some additional or alternative implementations, the memory may further have computer-executable instructions stored therein that, when executed, cause the one or more processors to: receive a plurality of user inputs, the plurality of user inputs including the first user input; and modify, responsive to receiving each of the user inputs, the first graphical user interface to accentuate the time intervals associated with a different one of the sleep stages of the predetermined set of different sleep stages and to provide textual content that is customized based on the sleep stage data of the first user that pertains to that sleep stage.

In some additional or alternative implementations, the hypnogram may include: a vertical axis with a different elevation indicated for each of the sleep stages of the predetermined set of different sleep stages and a horizontal axis representing time; and horizontal segments, each horizontal segment corresponding to a different one of the time intervals and located at the elevation corresponding to the sleep stage for the corresponding time interval. In such implementations, the memory may further have computer-executable instructions stored therein that, when executed, cause the one or more processors to accentuate the time intervals associated with the first sleep stage by marking regions between the horizontal axis and the horizontal segments located at the elevation associated with the first sleep stage with a different graphical appearance than regions between the horizontal axis and the horizontal segments located at the elevations associated with sleep stages of the predetermined set of different sleep stages other than the first sleep stage.

In some additional or alternative implementations, the memory may further have computer-executable instructions stored therein that, when executed, cause the one or more processors to generate a second graphical user interface component that indicates a relative percentile breakdown of total time spent in each of the sleep stages for the first sleep session.

In some additional or alternative implementations, the predetermined set of different sleep stages may include one or more sleep stages such as an artefact or off-wrist sleep stage, an awake sleep stage, a random eye movement (REM) sleep stage, a light sleep stage, or a deep sleep stage.

In some additional or alternative implementations, the memory may further have computer-executable instructions stored therein that, when executed, further cause the one or more processors to: receive representative personal sleep stage data, the representative personal sleep stage data indicating a representative relative percentile breakdown of total time spent in each of the sleep stages for a plurality of sleep sessions of the first user; and modify the second graphical user interface component to also indicate the representative relative percentile breakdown of the total time spent in each of the sleep stages for the plurality of sleep sessions of the first user in addition to the relative percentile breakdown of the total time spent in each of the sleep stages for the first sleep session.

In some additional or alternative implementations, the representative personal sleep stage data indicating the representative relative percentile breakdown of the total time spent in each of the sleep stages for the plurality of sleep sessions of the first user may be a relative percentile breakdown of the averages of the total time spent in each of the sleep stages for the plurality of sleep sessions of the first user.

In some additional or alternative implementations, the plurality of sleep sessions of the first user may include a number of sleep sessions spanning at least a time interval such as: a week prior to the time when the second graphical user interface component is generated, four weeks prior to the time when the second graphical user interface component is generated, 15 days prior to the time when the second graphical user interface component is generated, or 30 days prior to the time when the second graphical user interface component is generated.

In some additional or alternative implementations, the memory may further have computer-executable instructions stored therein that, when executed, further cause the one or more processors to: receive representative demographic sleep stage data, the representative demographic sleep stage data indicating a representative demographic relative percentile breakdown of total time spent in each of the sleep stages for a plurality of sleep sessions of a plurality of users; and modify the second graphical user interface component to also indicate the representative demographic relative percentile breakdown of the total time spent in each of the sleep stages for the plurality of sleep sessions of the plurality of users in addition to the relative percentile breakdown of the total time spent in each of the sleep stages for the first sleep session.

In some additional or alternative implementations, the representative demographic relative percentile breakdown of the total time spent in each of the sleep stages for the plurality of sleep sessions of the plurality of users may include percentile ranges associated with each of the sleep stages.

In some additional or alternative implementations, the plurality of users may be users within a first age range and may be the same gender as the first user, and the first user may be within the first age range.

In some implementations, an apparatus may be provided that includes a communications interface, one or more processors, and a memory. In such implementations, the one or more processors may be communicatively connected with the memory and the communications interface, and the memory may have computer-executable instructions stored therein that, when executed, cause the one or more processors to: receive sleep stage data for a first user, the sleep stage data including data indicating time intervals associated with a first sleep session of the first user and data indicating, for each time interval, a sleep stage associated with that time interval (in which the sleep stage associated with each time interval is selected from a predetermined set of different sleep stages); identify a plurality of display time intervals, each display time interval associated with one of the sleep stages of the set of different sleep stages (in which each display time interval of the plurality of display time intervals associated with an awake sleep stage of the set of different sleep stages may be coextensive with a different one of the time intervals associated with the awake sleep stage and having a duration greater than a first threshold amount, and each display time interval of the plurality of display time intervals associated with a sleep stage of the set of different sleep stages other than the awake sleep stage may be either coextensive with a different one of the time intervals associated with that sleep stage or span across one or more consecutive time intervals of the time intervals, each of the one or more consecutive time intervals a) associated with that sleep stage or b) associated with the awake sleep stage and having a duration less than or equal to the threshold amount); and display a hypnogram based on the display time intervals and the different sleep stages.

In some additional implementations, the memory may further have computer-executable instructions stored therein that, when executed, further cause the one or more processors to: display the hypnogram by displaying a first graphical element representing each display time interval. In such implementations, each first graphical element may have a dimension extending along a horizontal direction that is proportionate to a duration of the display time interval represented by that first graphical element, a horizontal location based on a start time of the display time interval represented by that first graphical element, and a vertical location that is based on the sleep stage associated with that display time interval.

In some additional or alternative implementations, the memory may further have computer-executable instructions stored therein that, when executed, further cause the one or more processors to cause one or more second graphical elements to be displayed on the hypnogram, each of the one or more second graphical elements representing a different one of the one or more time intervals associated with the awake sleep stage and having a duration less than or equal to the threshold amount.

In some additional or alternative implementations, the memory may further have computer-executable instructions stored therein that, when executed, further cause the one or more processors to cause the second graphical elements to be displayed on the hypnogram at the same elevation as the first graphical elements representing the display time intervals associated with the awake sleep stage.

In some additional or alternative implementations, the memory may further have computer-executable instructions stored therein that, when executed, further cause the one or more processors to cause vertical extension lines to be displayed on the hypnogram, each vertical extension line spanning between an end of each of the second graphical elements and a corresponding one of the first graphical elements extending across the same horizontal location as that end of the second graphical element. In such implementations, the vertical extension lines may have a different format from vertical lines used to connect the first graphical elements together.

In some implementations, an apparatus may be provided that includes a housing configured to be worn on a person's body; a heart-rate sensor located within the housing and configured to generate time-varying data of cardiovascular behavior; one or more processors; and a memory. In such implementations, the one or more processors may be communicatively connected with the heart-rate sensor and the memory, and the memory may have computer-executable instructions stored therein that, when executed, cause the one or more processors to: a) obtain data from the heart-rate sensor at a first sampling rate, b) extract a series of inter-beat intervals from the data, c) determine a reference value associated with values of the inter-beat intervals in the inter-beat interval series, d) determine a difference between the reference value and the value of each inter-beat interval in the inter-beat interval series to produce corresponding adjusted inter-beat interval values, and e) store inter-beat interval information based on the adjusted inter-beat interval values in the memory in association with the reference value.

In some additional implementations, the apparatus may further include a wireless communications interface, and the memory may have further computer-executable instructions stored therein that, when executed, further cause the one or more processors to: perform a) through e) for multiple time periods and cause the wireless communications interface to: transmit the inter-beat interval information for the inter-beat interval series of each time period of the multiple time periods, and transmit the reference value for the inter-beat interval series of each time period of the multiple time periods in association with the inter-beat interval information for that time period.

In some additional or alternative implementations, the reference value may be within the minimum/maximum range of the inter-beat intervals in the inter-beat interval series. In some other additional or alternative implementations, the reference value may be the arithmetic mean of the inter-beat intervals in the inter-beat interval series, the median of the inter-beat intervals in the inter-beat interval series, the mode of the inter-beat intervals in the inter-beat interval series, or a measure of central tendency of the inter-beat intervals in the inter-beat interval series.

In some additional or alternative implementations, the memory may have further computer-executable instructions stored therein that, when executed, further cause the one or more processors to quantize, prior to storing the inter-beat interval information based on the adjusted inter-beat interval values in the memory, the inter-beat interval values. In such implementations, the quantizing may reduce the number of unique values in the inter-beat interval information based on the adjusted inter-beat interval values as compared with the number of unique values of inter-beat intervals in the series of inter-beat intervals extracted from the data.

In some additional or alternative implementations, the reference value may be the arithmetic mean, median, or mode, and the memory may have further computer-executable instructions stored therein that, when executed, further cause the one or more processors to quantize the adjusted inter-beat interval values that are within a first threshold of the reference value according to a first quantization step size, and quantize the adjusted inter-beat interval values that are outside of the first threshold of the reference value according to a second quantization step size that is larger than the first quantization step size.

In some additional or alternative implementations, the first threshold may be based on a predetermined fixed value. In some other additional or alternative implementations, the memory may have further computer-executable instructions stored therein that, when executed, further cause the one or more processors to determine the first threshold based on the inter-beat values in the inter-beat interval series, and store the first threshold in the memory in association with the inter-beat interval information.

In some additional or alternative implementations, the memory may have further computer-executable instructions stored therein that, when executed, further cause the one or more processors to quantize, prior to storing the inter-beat interval information based on the adjusted inter-beat interval values in the memory, at least one of the inter-beat interval values and the adjusted inter-beat interval values. In such implementations, the quantizing may reduce the number of unique values in the inter-beat interval information based on the adjusted inter-beat interval values as compared with the number of unique values of inter-beat intervals in the series of inter-beat intervals extracted from the data.

In some additional or alternative implementations, the reference value may be the arithmetic mean, median, or mode, and the memory may have further computer-executable instructions stored therein that, when executed, further cause the one or more processors to: quantize the at least one of the inter-beat interval values and the adjusted inter-beat interval values, for the inter-beat interval values or the adjusted inter-beat interval values that are within a first threshold of the reference value, according to a first quantization step size, and quantize the at least one of the inter-beat interval values and the adjusted inter-beat interval values, for the inter-beat interval values or the adjusted inter-beat interval values that are outside of the first threshold of the reference value, according to a second quantization step size that is larger than the first quantization step size.

In some additional or alternative implementations, the first threshold may be based on a predetermined fixed value. In some other additional or alternative such implementations, the memory may have further computer-executable instructions stored therein that, when executed, further cause the one or more processors to: determine the first threshold based on the inter-beat values in the inter-beat interval series, and store the first threshold in the memory in association with the inter-beat interval information.

In some additional or alternative implementations, the first sampling rate may be 25 Hz or higher, and the memory may have further computer-executable instructions stored therein that, when executed, further cause the one or more processors to: temporarily store the inter-beat interval values as 11-bit or higher values, temporarily store the adjusted inter-beat values as 9-bit or lower values prior to quantization, and store the adjusted inter-beat values as 6-bit or lower values.

In some implementations, a method may be provided that includes: a) obtaining data from a heart-rate sensor at a first sampling rate, b) extracting a series of inter-beat intervals from the data, c) determining a reference value associated with values of the inter-beat intervals in the inter-beat interval series, d) determining a difference between the reference value and the value of each inter-beat interval in the inter-beat interval series to produce corresponding adjusted inter-beat interval values, and e) storing inter-beat interval information based on the adjusted inter-beat interval values in a computer-readable memory in association with the reference value.

In some additional implementations, the method may further include performing a) through e) for multiple time periods and causing a wireless communications interface to: transmit the inter-beat interval information for the inter-beat interval series of each time period of the multiple time periods and transmit the reference value for the inter-beat interval series of each time period of the multiple time periods in association with the inter-beat interval information for that time period.

In some additional or alternative implementations, the reference value may be within the minimum/maximum range of the inter-beat intervals in the inter-beat interval series. In some additional or alternative implementations, the reference value may be the arithmetic mean, median, or mode of the inter-beat intervals in the inter-beat interval series. In some additional or alternative implementations, the reference value may be the mode of the inter-beat intervals in the inter-beat interval series. In some additional or alternative implementations, the reference value may be a measure of central tendency of the inter-beat intervals in the inter-beat interval series.

In some additional or alternative implementations, the method may further include quantizing, prior to storing the inter-beat interval information based on the adjusted inter-beat interval values in the memory, at least one of the inter-beat interval values and the adjusted inter-beat interval values. In such implementations, the quantizing may reduce the number of unique values in the inter-beat interval information based on the adjusted inter-beat interval values as compared with the number of unique values of inter-beat intervals in the series of inter-beat intervals extracted from the data. In some additional such implementations, the reference value may be the arithmetic mean, median, or mode of the inter-beat intervals in the inter-beat interval series and the quantizing may include quantizing the at least one of the inter-beat interval values and the adjusted inter-beat interval values, for the inter-beat interval values or the adjusted inter-beat interval values that are within a first threshold of the reference value, according to a first quantization step size, and quantizing the at least one of the inter-beat interval values and the adjusted inter-beat interval values, for the inter-beat interval values or the adjusted inter-beat interval values that are outside of the first threshold of the reference value, according to a second quantization step size that is larger than the first quantization step size. In some additional such implementations, the first threshold may be based on a predetermined fixed value, whereas in some other such implementations, the method may further include determining the first threshold based on the inter-beat values in the inter-beat interval series and storing the first threshold in the memory in association with the inter-beat interval information.

In some additional or alternative implementations, the first sampling rate may be 25 Hz or higher and the method may further include temporarily storing the inter-beat interval values as 11-bit or higher values, temporarily storing the adjusted inter-beat values as 9-bit or lower values prior to quantization, and storing the adjusted inter-beat values as 6-bit or lower values.

In some implementations, a sleep monitoring system may be provided that includes a wearable electronic device to be worn by a user. The wearable electronic device may include one or more motion sensors to generate motion data that represents motion of the wearable electronic device and one or more optical sensors to generate cardiopulmonary pulse-related data that represents circulatory system characteristics of the user. The wearable electronic device may also include one or more processors configured to receive data from the one or more motion sensors and the one or more optical sensors and a non-transitory, machine-readable storage medium operatively coupled to the one or more processors and having stored therein computer-executable instructions that, when executed, cause the one or more processors to, for each time period of a plurality of time periods: extract one or more movement features from the motion data for one or more first time windows associated with that time period (in which each of the first time windows may be associated with a different movement feature of the one or more movement features); extract one or more pulse data features from the cardiopulmonary pulse-related data for one or more second time windows associated with that time period, each of the second time windows associated with a different pulse data feature of the one or more pulse data features; and classify that time period with a sleep stage classification selected from a plurality of potential sleep stage classifications based on the one or more movement features extracted from the motion data for the one or more first time windows associated with that time period and the one or more pulse data features extracted from the cardiopulmonary pulse-related data for the one or more second time windows associated with that time period.

In some additional implementations, the one or more processors may be located in the wearable electronic device.

In some additional or alternative implementations, the wearable electronic device may further include a communications interface configured to communicate the motion data and the cardiopulmonary pulse-related data to the one or more processors, and the one or more processors may be located in a location remote from the wearable electronic device.

In some additional or alternative implementations, the one or more processors may be located in a portable electronic device selected from the group consisting of: smartphones, tablet computers, and laptop computers.

In some additional or alternative implementations, the one or more processors may be located in one or more servers.

In some additional or alternative implementations, at least two of the time windows of the first time windows, the second time windows, or the first time windows and the second time windows may have the same start point and the same end point and may thus have the same duration.

In some additional or alternative implementations, at least two of the time windows of the first time windows, the second time windows, or the first time windows and the second time windows may have the same start point and the same end point as the time period with which they are associated and may thus have the same duration as that time period.

In some additional or alternative implementations, the non-transitory, machine-readable storage medium may further store therein computer-executable instructions that, when executed, cause the one or more processors to apply one or more post-classification rules to the plurality of time periods, where each post-classification rule compares the sleep stage classifications for two or more of the time periods, and change one or more of the sleep stage classifications of one or more of the time periods of the plurality of time periods responsive to the one or more post-classification rules.

In some additional or alternative implementations, the plurality of potential sleep stage classifications may at least include an awake classification and a deep sleep classification, and the one or more post-classification rules may include a post-classification rule that causes the sleep stage classification of the time periods with the awake classification to be changed from the awake classification to the deep sleep classification for the time periods with the awake classification that have neighboring time periods with the deep sleep classification.

In some additional or alternative implementations, the non-transitory, machine-readable storage medium may further store therein computer-executable instructions that, when executed, cause the one or more processors to, when classifying each time period, determine, for each time period, a confidence number for each of the potential sleep stage classifications based on the one or more movement features extracted from the motion data for the one or more first time windows associated with that time period and the one or more pulse data features extracted from the cardiopulmonary pulse-related data for the one or more second time windows associated with that time period and classify that time period with the sleep stage classification corresponding to the potential sleep stage classification with the highest confidence number for that time period.

In some additional or alternative implementations, the one or more optical sensors may include a photoplethysmogram sensor, the one or more motion sensors may include an accelerometer, or the one or more optical sensors may include a photoplethysmogram sensor and of one or more motion sensors includes an accelerometer.

In some additional or alternative implementations, the one or more movement features and the one or more pulse data features for each time period, collectively, may include one or more features such as a cumulative movement index extracted from the motion data; a first elapsed time between a first time within that time period and a second time before that time period when the cumulative movement index last exceeded a first threshold amount; a second elapsed time between a third time within that time period and a fourth time after that time period when the cumulative movement index first exceeded a second threshold amount; a third elapsed time between a fifth time within that time period and a closest time outside of that time period when the cumulative movement index first exceeded a third threshold amount; a first number of time windows before that time period since the cumulative movement index last exceeded a fourth threshold amount; a second number of time windows after that time period until the cumulative movement index first exceeded a fifth threshold amount; a mean heart rate across one of the one or more second time windows associated with that time period; a standard deviation for the mean heart rate across one of the one or more second time windows associated with that time period; a mean peak-to-peak value of the cardiopulmonary pulse-related data for one of the one or more second time windows associated with that time period; a mean trough-to-trough value of the cardiopulmonary pulse-related data for one of the one or more second time windows associated with that time period; a standard deviation of the peak-to-peak value of the cardiopulmonary pulse-related data for one of the one or more second time windows associated with that time period; a standard deviation of the trough-to-trough value of the cardiopulmonary pulse-related data for one of the one or more second time windows associated with that time period; a difference between a 90th percentile peak-to-peak value and a 10th percentile peak-to-peak value of the cardiopulmonary pulse-related data for one of the one or more second time windows associated with that time period; a difference between a 90th percentile trough-to-trough value and a 10th percentile trough-to-trough value of the cardiopulmonary pulse-related data for one of the one or more second time windows associated with that time period; the power in a low-frequency band of a heart rate variability analysis of the cardiopulmonary pulse-related data for one of the one or more second time windows associated with that time period (in which the low-frequency band may be between 0.04 and 0.15 Hz); the power in a high-frequency band of a heart rate variability analysis of the cardiopulmonary pulse-related data for one of the one or more second time windows associated with that time period (in which the high-frequency band may be between 0.15 and 0.4 Hz); a ratio of the power in a low-frequency band of a heart rate variability analysis of the cardiopulmonary pulse-related data for one of the one or more second time windows associated with that time period to the power in a high-frequency band of the heart rate variability analysis of the cardiopulmonary pulse-related data for the one of the one or more second time windows associated with that time period, (in which the low-frequency band may be between 0.04 and 0.15 Hz and the high-frequency band may be between 0.15 and 0.4 Hz); the total power in a low-frequency band of a heart rate variability analysis of the cardiopulmonary pulse-related data for one of the one or more second time windows associated with that time period as a percentage of the total power of the heart rate variability analysis of the cardiopulmonary pulse-related data for the one of the one or more second time windows associated with that time period (in which the high-frequency band may be between 0.04 and 0.15 Hz); the total power in a high-frequency band of a heart rate variability analysis of the cardiopulmonary pulse-related data for one of the one or more second time windows associated with that time period as a percentage of the total power of the heart rate variability analysis of the cardiopulmonary pulse-related data for the one of the one or more second time windows associated with that time period (in which the high-frequency band may be between 0.15 and 0.4 Hz); the standard deviation of an envelope of the cardiopulmonary pulse-related data for one of the one or more second time windows associated with that time period; an estimated respiration rate based on a DC value of the cardiopulmonary pulse-related data for one of the one or more second time windows associated with that time period; or a variability of the pulse shapes in the cardiopulmonary pulse-related data for one of the one or more second time windows associated with that time period.

In some additional or alternative implementations, the one or more pulse data features for each time period may include one or more pulse data features such as: a mean heart rate across one of the one or more second time windows associated with that time period; a standard deviation for the mean heart rate across one of the one or more second time windows associated with that time period; a mean peak-to-peak value of the cardiopulmonary pulse-related data for one of the one or more second time windows associated with that time period; a mean trough-to-trough value of the cardiopulmonary pulse-related data for one of the one or more second time windows associated with that time period; a standard deviation of the peak-to-peak value of the cardiopulmonary pulse-related data for one of the one or more second time windows associated with that time period; a standard deviation of the trough-to-trough value of the cardiopulmonary pulse-related data for one of the one or more second time windows associated with that time period; a difference between a 90th percentile peak-to-peak value and a 10th percentile peak-to-peak value of the cardiopulmonary pulse-related data for one of the one or more second time windows associated with that time period; a difference between a 90th percentile trough-to-trough value and a 10th percentile trough-to-trough value of the cardiopulmonary pulse-related data for one of the one or more second time windows associated with that time period; the power in a low-frequency band of a heart rate variability analysis of the cardiopulmonary pulse-related data for one of the one or more second time windows associated with that time period (in which the low-frequency band may be between 0.04 and 0.15 Hz); the power in a high-frequency band of a heart rate variability analysis of the cardiopulmonary pulse-related data for one of the one or more second time windows associated with that time period (in which the high-frequency band may be between 0.15 and 0.4 Hz); a ratio of the power in a low-frequency band of a heart rate variability analysis of the cardiopulmonary pulse-related data for one of the one or more second time windows associated with that time period to the power in a high-frequency band of the heart rate variability analysis of the cardiopulmonary pulse-related data for the one of the one or more second time windows associated with that time period (in which the low-frequency band may be between 0.04 and 0.15 Hz and the high-frequency band may be between 0.15 and 0.4 Hz); the total power in a low-frequency band of a heart rate variability analysis of the cardiopulmonary pulse-related data for one of the one or more second time windows associated with that time period as a percentage of the total power of the heart rate variability analysis of the cardiopulmonary pulse-related data for the one of the one or more second time windows associated with that time period (in which the high-frequency band may be between 0.04 and 0.15 Hz); or the total power in a high-frequency band of a heart rate variability analysis of the cardiopulmonary pulse-related data for one of the one or more second time windows associated with that time period as a percentage of the total power of the heart rate variability analysis of the cardiopulmonary pulse-related data for the one of the one or more second time windows associated with that time period (in which the high-frequency band may be between 0.15 and 0.4 Hz), in which the cardiopulmonary pulse-related data for the time periods of a sleep session may be normalized before those one or more pulse data features are extracted, and the cardiopulmonary pulse-related data may be normalized such that the mean peak-to-peak value or trough-to-trough value for the time periods, in aggregate, of the sleep session is equal to a to a predetermined value. In some additional such implementations, the predetermined value may be 1.

In some additional or alternative implementations, the one or more movement features for each time period may include one or more movement features such as a cumulative movement index extracted from the motion data for that time period, a first elapsed time between a first time within that time period and a second time before that time period when the cumulative movement index last exceeded a first threshold amount, a second elapsed time between a third time within that time period and a fourth time after that time period when the cumulative movement index first exceeded a second threshold amount, a third elapsed time between a fifth time within that time period and a closest time outside of that time period when the cumulative movement index first exceeded a third threshold amount, a first number of time windows before that time period since the cumulative movement index last exceeded a fourth threshold amount, and a second number of time windows after that time period until the cumulative movement index first exceeded a fifth threshold amount. In such implementations, the one or more pulse data features may include one or more pulse data features such as a variability, as assessed by sample entropy, of inter-beat intervals in the cardiopulmonary pulse-related data for one of the one or more second time windows associated with that time period; a variability, as assessed by sample entropy, of the cardiopulmonary pulse-related data for one of the one or more second time windows associated with that time period; a root mean square deviation of the inter-beat intervals for one of the one or more second time windows associated with that time period; a root mean square deviation of the cardiopulmonary pulse-related data for one of the one or more second time windows associated with that time period; a low-frequency spectral power of the inter-beat intervals for one of the one or more second time windows associated with that time period; a low-frequency spectral power of the inter-beat intervals for one of the one or more second time windows associated with that time period; a high-frequency spectral power of the inter-beat intervals for one of the one or more second time windows associated with that time period; a high-frequency spectral power of the cardiopulmonary pulse-related data for one of the one or more second time windows associated with that time period; a variability of an envelope of the cardiopulmonary pulse-related data for one of the one or more second time windows associated with that time period; a variability of an envelope of the inter-beat intervals for one of the one or more second time windows associated with that time period; a variability of a de-trended respiration rate extracted from the cardiopulmonary pulse-related data for one of the one or more second time windows associated with that time period; an inter-percentile spread of a heart rate extracted from the cardiopulmonary pulse-related data for one of the one or more second time windows associated with that time period or from the inter-beat intervals for one of the one or more second time windows associated with that time period; a normalized de-trended heart rate extracted from the cardiopulmonary pulse-related data for one of the one or more second time windows associated with that time period or from the inter-beat intervals for one of the one or more second time windows associated with that time period; or a cross-correlation of each pulse shape of one or more pulse shapes in the cardiopulmonary pulse-related data for one of the one or more second time windows associated with that time period with a previous pulse shape in the cardiopulmonary pulse-related data, in which the pulse shapes may be normalized to a common duration prior to the cross-correlation.

In some additional or alternative implementations, the one or more movement features may include at least one of: a time since a last movement, a time until next movement, and/or a time from nearest movement, and the one or more pulse data features may include at least one of: a variability of an inter-beat series assessed using sample entropy, a variability of a de-trended respiration rate extracted from the cardiopulmonary pulse-related data, and/or a cross-correlation of a pulse rate signals.

In some additional or alternative implementations, the computer-executable instructions that cause the one or more processors to classify each time period may include instructions that, when executed, cause the one or more processors to transmit the one or more movement features and the one or more pulse data features to a server system that executes a classifier that generates the sleep stage classification for each time period and provides that sleep stage classification to the one or more processors.

In some additional or alternative implementations, the computer-executable instructions may further cause, when executed, the one or more processors to fill in missing data points in the cardiopulmonary pulse-related data prior to causing the one or more processors to extract the one or more pulse data features from the motion data for the one or more first time windows.

These and other implementations are described in further detail with reference to the Figures and the detailed description below.

BRIEF DESCRIPTION OF THE DRAWINGS

The present disclosure is illustrated by way of example, and not limitation, in the figures of the accompanying drawings, in which like reference numerals indicate similar elements unless otherwise indicated.

DETAILED DESCRIPTION

Overview

Figure 1:
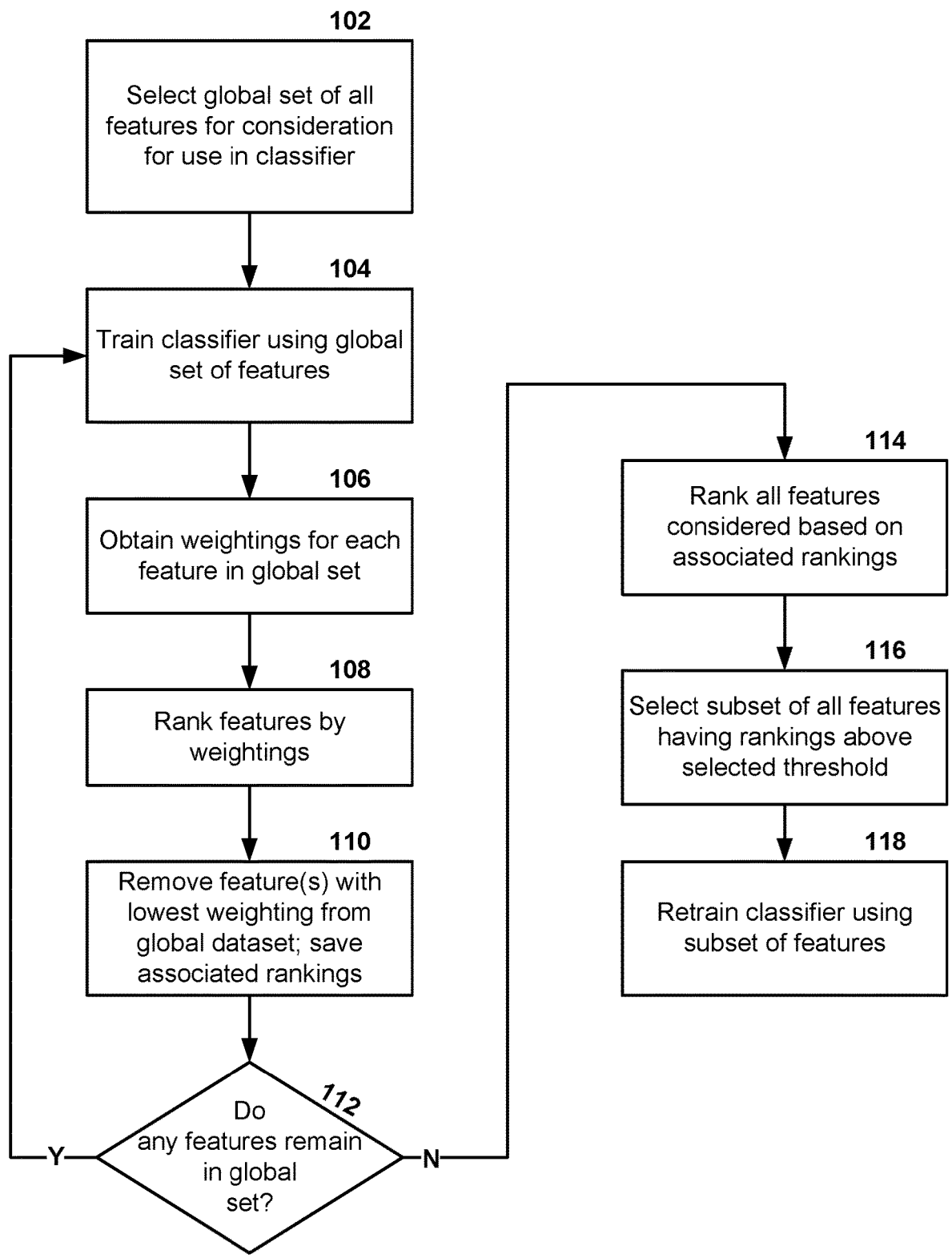
FIG. 1 depicts a high-level flow diagram for a sleep-classifier training technique.

During sleep, a person may pass through a number of different sleep states or stages that may be categorized in a number of different ways. In actual practice, a sleep session for a person's sleep may be divided into a number of intervals, which are often referred to as "epochs," and each such interval may be evaluated to determine what sleep state or stage the person was in during that interval. For example, the American Academy of Sleep Medicine Guidelines define four classes of sleep: W, N1-N2, N3, and random eye movement (REM), which may be viewed as corresponding to Wake (or Awake), Light Sleep (which may include both N1 and N2), Deep Sleep, and REM Sleep, respectively. Other approaches may include fewer or greater numbers of sleep stages. For example, an "artefact/off wrist" sleep stage may be used to classify time periods where the data indicates that the wearable device is not being worn or where the data from the wearable device defies classification as a "normal" sleep stage. Alternatively, time periods where the data indicates that the wearable device is not being worn or where the data from the wearable device defies classification as a "normal" sleep stage may be dealt with in other ways. For example, such time periods may simply be treated as gaps in the data record, may be assigned an "interpolated" sleep stage (for example, the average sleep stage of a plurality of time periods immediately before, immediately after, or including the time period having the missing sleep stage data), or may be assigned a "wild" sleep stage (for example, they may be treated as being equivalent to multiple different sleep stages).

Discussed herein are various techniques and systems for classifying the sleep states or stages of a subject based on data from a wearable electronic device, such as a wearable biometric monitoring device having, for example, a heart rate sensor and a motion sensor, as opposed to more traditional systems that utilize expert interpretation of the output of EEG devices. As used herein, a "wearable" biometric monitoring device is a device that is designed for comfortable and unobtrusive wear, such as a wrist-worn device like a Fitbit Charge HR, Fitbit Surge, Fitbit Blaze, etc. Devices such as EEG systems and electrocardiogram systems featuring a mesh of electrodes that must be adhered to different locations on a person's body and that are then connected with some form of external processing system are not unobtrusive and generally not viewed as comfortable, and are thus are not considered "wearable" biometric monitoring devices, as the term is used herein.

In the systems discussed herein, various data-driven features for a given time interval of a sleep session may be derived from optical heart rate sensor data and/or accelerometer sensor data that is obtained in association with that time interval. These features may then be provided to a classifier that classifies that time interval into one of several classes or stages of sleep based on the values of one or more of the data-driven features. The classifier may be trained based on the values of similar data-driven features that are collected during sleep sessions that are, for example, classified using more traditional techniques, such as manual scoring by professional sleep scorers, which may frequently be referred to as "polysomnographic technologists" or "polysomnographic technicians," using more sophisticated equipment. Thus, for example, a small population of sleepers may be monitored during sleep by both a wearable biometric monitoring device and more complicated instruments that are used by one or more sleep scorers to evaluate and classify intervals or epochs during a sleep session into the various sleep stages. Thus, each time interval or epoch collected during such training may have associated with it a) a sleep stage that has been assigned to it by one or more trained sleep scorers and b) a set of data-driven features collected by the wearable biometric monitoring device during a time period associated with that time interval or epoch.

The data-driven features collected by the wearable biometric monitoring system during such training sleep sessions, in conjunction with the sleep stage classifications provided by the sleep scorers, may then be used to train the classifier so that the classifier can classify intervals or epochs during a sleep session based only on the data from a wearable biometric monitoring device. Such classification may include, for example, labeling the time interval with an indicator indicating sleep stage classification based on how that interval of time is classified by the classifier. Thus, the trained classifier may be used to classify sleep for a much larger population of sleepers that only use a wearable biometric monitoring device to monitor their sleep, without the need for more in-depth sleep monitoring equipment or the direct involvement of individuals trained in sleep scoring. The classifications that are provided by such a classifier may be post-processed, in some embodiments, to address potential classification artifacts. For example, if a series of epochs or intervals during a sleep session exhibits a classification pattern that is seldom, if ever, seen during "scored" sleep sessions, then one or more of those epochs or intervals may be re-classified according to one or more heuristics or other rules.

There may be a very large number of data-driven features that may be used in a classifier. During the training process, some or many of these data-driven features may be eliminated from the classifier since they may contribute to the accuracy of the classifier in an insignificant or less impactful way. FIG. 1 depicts a high-level flow diagram for one technique for pruning out less useful features from a set of features that may be used to train a classifier.

In block 102, a global set of features being considered for use in a classifier may be selected. The number of such features may be relatively high, e.g., in the hundreds of features, in some cases. In block 104, the classifier may be trained using the training dataset, e.g., the features extracted from the data collected in association with known classifications. As part of the classifier training, each feature involved in the training may become associated with a weighting factor or other quantifier of the feature's importance in the classification determination. In block 106, the weighting factors (or other quantifier of importance) for each feature in the global set of features may be obtained, and the features may then be ranked by their weighting factors (or other quantifiers of importance) in block 108. The feature or features with the lowest weighting factor(s) or other quantifier(s) of importance may then be removed from the global set of features (in some cases, there may be multiple features with the lowest weighting factor, so multiple features may be removed). The ranking(s) of the features with the lowest weighting factor(s) or other quantifier(s) of importance may be preserved for later reference. In block 112, a determination may be made if there are any features remaining in the global set—if so, then the technique may return to block 104, and the operations of blocks 104 through 110 may be repeated for a smaller set of features. Eventually, all of the features will have been removed from the global set and had rankings assigned to them upon removal from the global set. From a practical standpoint, once the global set has only one feature left in it, the training of the classifier using that last feature and the formal removal of that last feature from the global set may be skipped and the remaining feature may simply be assigned the first ranked position. If it is determined in block 112 that there are no features left in the global set (or, alternatively, that all features have been assigned ranks per the operations in block 110 or an equivalent), then the technique may proceed to block 114, in which the features may be ranked by their associated rankings (as determined in block 110, for example). In block 116, a subset of the features may be selected based on having rankings above a selected threshold. The classifier may then be re-trained using the selected subset of features in block 118. This technique allows for the pruning out of features that contribute to classification in an insignificant way, thus allowing classification speed and computational efficiency to be kept high without significantly impacting classification accuracy in a negative manner. Various tools for training, validating, and testing classifiers of various types may be found, for example, in the documentation for scikit-learn, which is a module developed for the Python programming language (http://scikit-learn.sourceforge.net).

The intervals or epochs for a sleep session that have been classified may then be summarized and presented to a user in a variety of useful and informative ways via a graphical user interface.

In some embodiments, the data-driven features that are discussed above may be compressed and stored in particular ways to reduce the memory or bandwidth that may be needed in order to store or transmit such data-driven features.

These and other embodiments of the concepts discussed herein are described, by way of example, in further detail below.

Example Sleep Monitoring Platform or System

Figure 2:
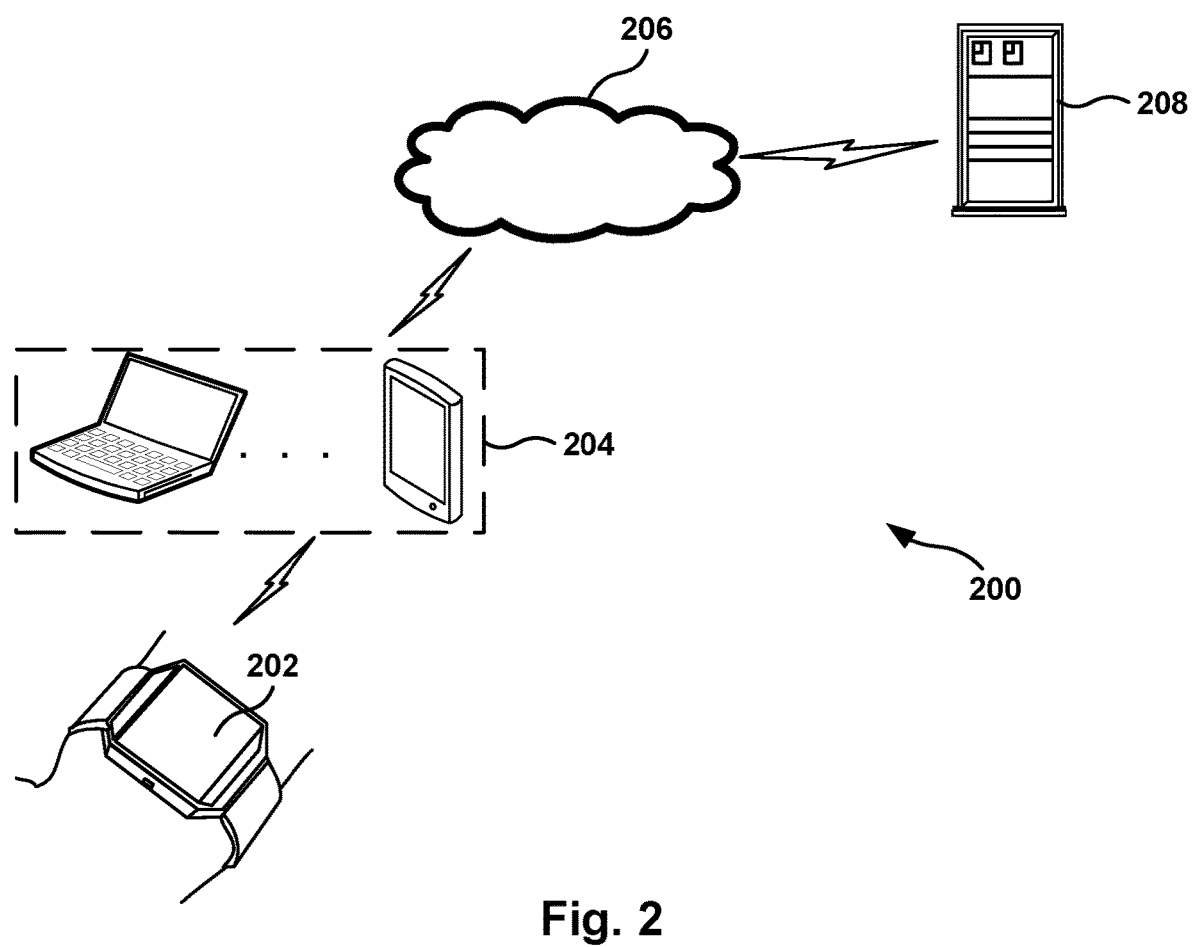
FIG. 2 illustrates an example of a sleep monitoring platform for implementing various example embodiments.

FIG. 2 illustrates an example of a sleep monitoring platform 200 for implementing various example embodiments. In some embodiments, the sleep monitoring platform 200 comprises a wearable device 202, a secondary device 204, a network 206, and a backend system 208. The components of the sleep monitoring platform 200 may be connected directly or over a network 206, which may be any suitable network. In various embodiments, one or more portions of the network 206 may include an ad hoc network, an intranet, an extranet, a virtual private network (VPN), a local area network (LAN), a wireless LAN (WLAN), a wide area network (WAN), a wireless WAN (WWAN), a metropolitan area network (MAN), a portion of the Internet, a portion of the Public Switched Telephone Network (PSTN), a cellular telephone network, or any other type of network, or a combination of two or more such networks.

Although FIG. 2 illustrates a particular example of the arrangement of the wearable device 202, the secondary device 204, the network 206, and the backend system 208, any suitable arrangement or configuration of the wearable device 202, the secondary device 204, the network 206, and the backend system 208 may be contemplated.

The wearable device 202 may be a wearable device configured to be attached to the wearer's body, such as a wrist-worn band, watch, finger clip, ear-clip, chest-strap, ankle strap, or any other suitable device.

The secondary device 204 may be any suitable computing device, such as a smart phone, a personal digital assistant, a mobile phone, a personal computer, a laptop, a computing tablet, or any other device suitable for connecting with one or more of the wearable device 204 or the backend system 208.

The wearable device 202 may access the secondary device 204 or the backend system 208 directly, via the network 206, or via a third-party system. For example, the wearable device 204 may access the backend system 208 via the secondary device 204.

The backend system 208 may include a network-addressable computing system (or systems), e.g., a server or servers, that can host and process sensor data for one or more users. The backend system 208 may generate, store, receive, and transmit sleep-related data, such as, for example, sleep duration, bed-time, awake-time, restless-time, sleep states (e.g., sleep stages, restless, etc.), or any other sleep-related statistics. The backend system 208 may be accessed by the other components of the sleep monitoring platform 200 either directly or via the network 206. The user 202 may use the wearable device 204 to access, send data to, and/or receive data from the secondary device 204 and/or the backend system 208.

Figure 3:
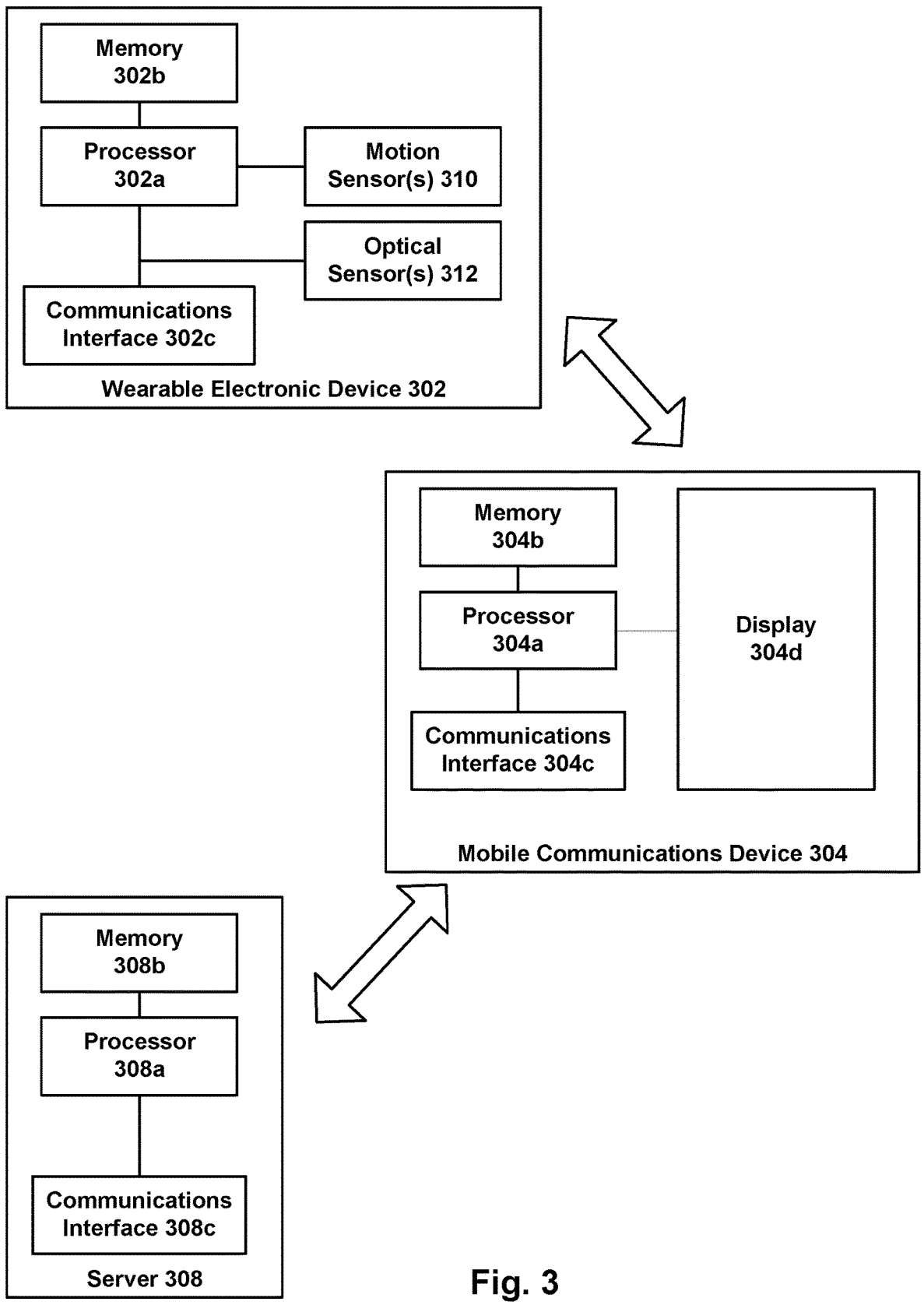
FIG. 3 depicts a more detailed block diagram of various components that may be used in a sleep monitoring platform such as that illustrated in FIG. 2.

FIG. 3 depicts a more detailed block diagram of various components that may be used in a sleep monitoring platform such as that illustrated in FIG. 2. In FIG. 3, a wearable device 302, a secondary device 304, and a backend system 308 are shown. The wearable device 302, which may also be referred to herein as a "wearable biometric monitoring device," "wearable biometric tracking device," or just "biometric tracking device" or "biometric monitoring device," may include one or more processors 302a, a memory 302b, and a communications interface 302c. The communications interface 302c may, for example, include a wireless communications system, such as a Bluetooth interface, for communicating wirelessly with other components, such as the secondary device 304. The memory 302b may store computer-executable instructions for controlling the one or more processors 302a to perform various functions discussed herein, including, for example, instructions for causing the one or more processors 302a to obtain motion data from one or more motion sensors 310 and pulse-related data from one or more optical sensors 312.

The secondary device 304, which may, as discussed herein, be a cell phone, smartphone, laptop, or other device, may similarly include one or more processors 304a, a memory 304b, and a communications interface 304c. The secondary device 304 may also include a display 304d (the wearable device 302, as well as the backend system 308, may also include displays, but the secondary device 304 may be the most likely device through which a user may interact with the data collected by the wearable device 302, so the display 304d is explicitly indicated since the avenue through which such interaction may occur). The memory 304b may store computer-executable instructions for controlling the one or more processors 304a perform various functions discussed herein and to send and receive data or instructions via the communications interface 304c, e.g., to or from either or both of the wearable device 302 and backend system 308.

The backend device 308, which may, for example, be one or more servers or other backend processing systems, may include one or more processors 308a, a memory 308b, and a communications interface 308c. The memory 308b may store computer-executable instructions for controlling the one or more processors 308a to provide various functionalities described herein.

Figure 4:
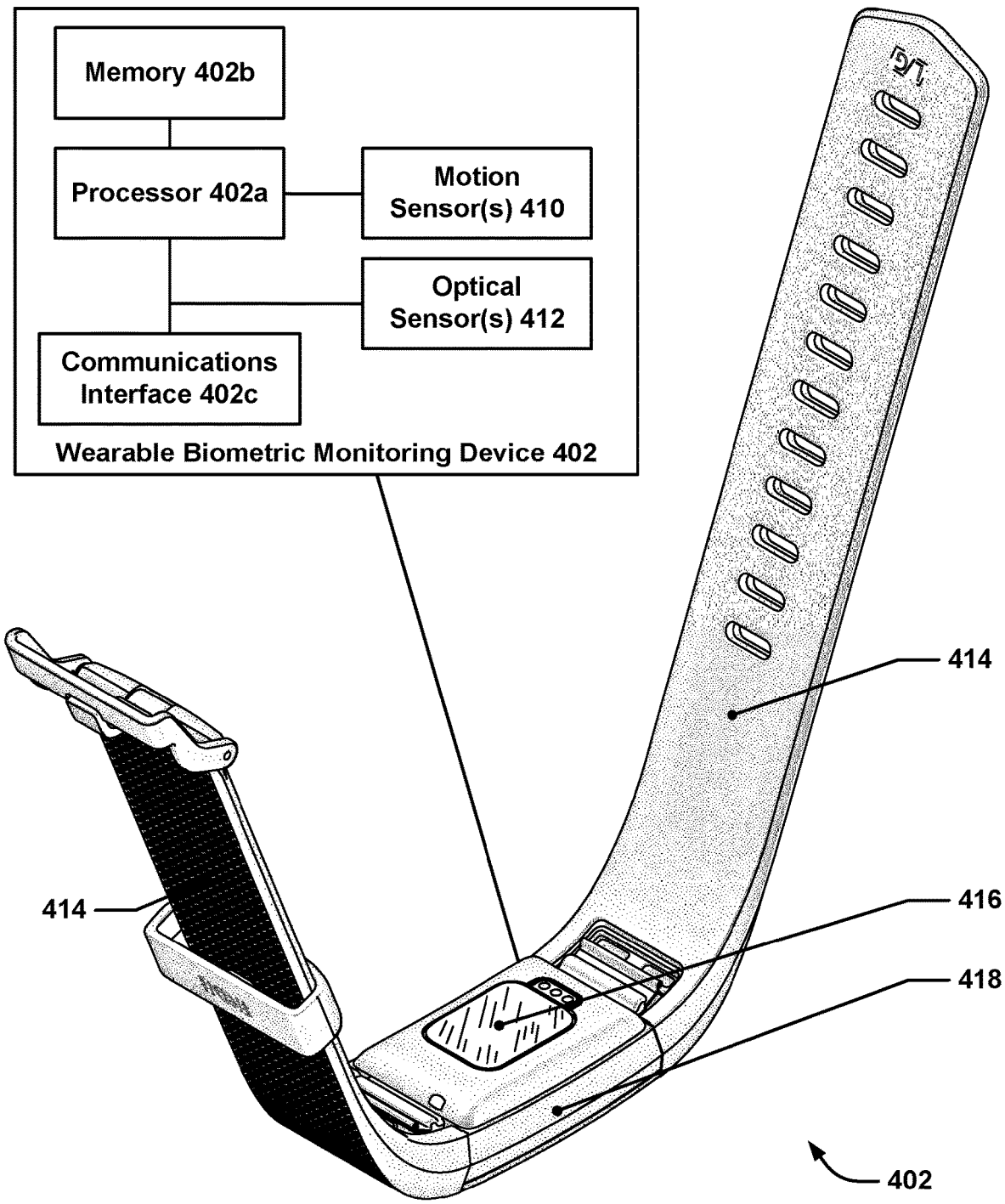
FIG. 4 depicts an isometric view of a wearable device that may be used collect pulse-related data and motion data during a sleep session for use in the techniques and systems discussed herein.

FIG. 4 depicts an isometric view of a wearable device—in this case, a Fitbit Charge 2™—that may be used collect pulse-related data and motion data during a sleep session for use in the techniques and systems discussed herein. The wearable device 402 may include a housing 418 that is connected to straps 414 that may be fastened together to attach the wearable device 402 to a person's wrist. The housing 418 may include a window 416 that allows optical sensors 412 to measure pulse-related physiological phenomena of the wearer. The wearable device 402 may, as discussed earlier, include one or more processors 402a, a memory 402b, and a communications interface 402c, in addition to the one or more optical sensors 412 and one or more motion sensors 410. The memory 402b may store computer-executable instructions for controlling the one or more processors to obtain the motion data from the one or more motion sensors 410, obtain the pulse-related data from the one or more optical sensors 412, and to then transmit such data to other devices in the sleep monitoring platform. The one or more optical sensors may, for example, include one or more light sources and one or more photodetectors that are placed adjacent to a person's skin. The light source(s) and photodetector(s) are typically arranged so that light from the light source(s) cannot reach the photodetector(s) directly. However, when such an optical sensor is placed adjacent to a person's skin, light from the light source(s) may diffuse into the person's flesh and then be emitted back out of the person's flesh such that the photodetector(s) can detect it. The amount of such light that is emitted from the person's flesh may vary as a function of heart rate, since the amount of blood present in the flesh varies as a function of heart rate and the amount of light that is emitted from the person's flesh, in turn, varies as a function of the amount of blood present. Depending on the wavelengths of light used, different measurements of a person's circulatory system may be obtained. For example, green light is particularly well-suited for measuring heart rate, whereas a combination of red light and infrared light is particularly well-suited for measuring blood oxygenation levels.

Figure 5:
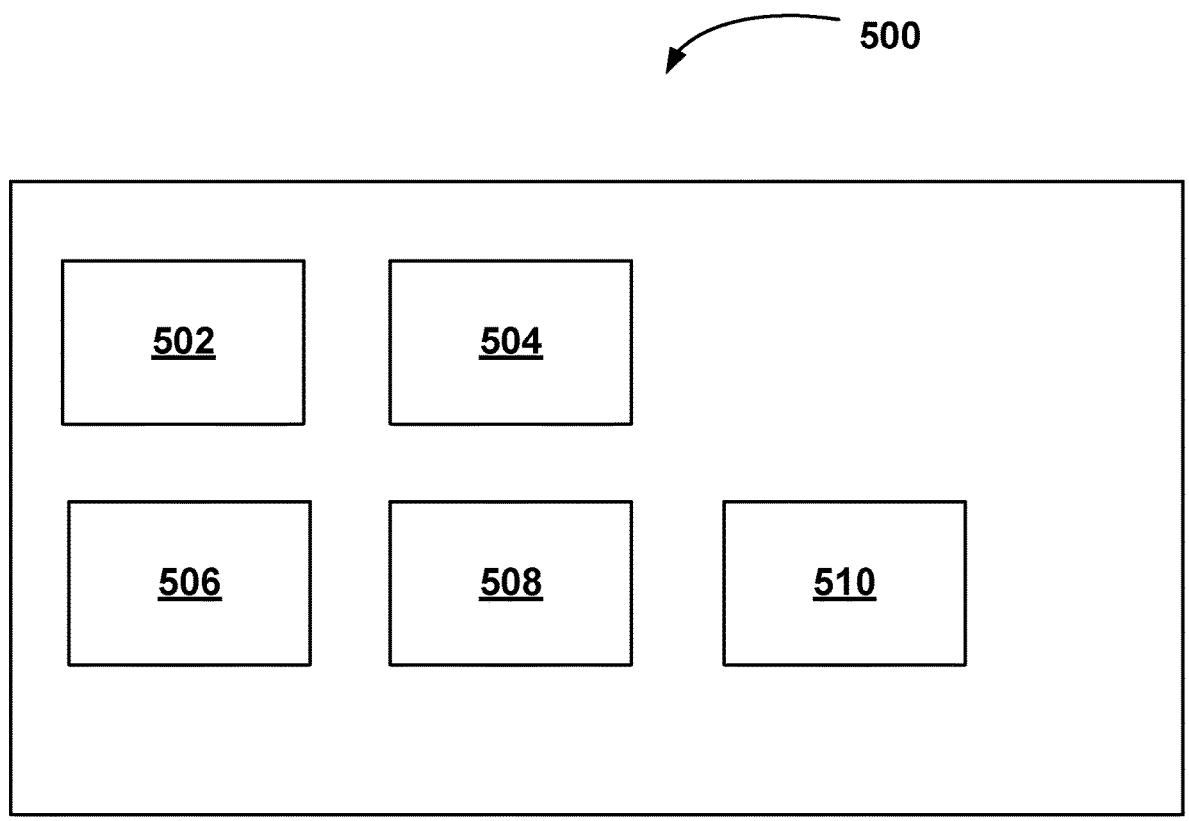
FIG. 5 is a block diagram depicting various modules, in accordance with example embodiments, that may be included in a processing system.

FIG. 5 is a block diagram depicting various modules, in accordance with example embodiments, that may be included in a processing system 500. It should be appreciated that the processing system 500 may be deployed in the form of, for example, a wearable device, a server computer, a client computer, a personal computer, a laptop computer, a mobile phone, a personal digital assistant, and other processing systems, or combinations thereof. For example, in one embodiment, the processing system 500 may be embodied as the backend system 208 of the sleep monitoring platform 200 depicted in FIG. 2. In an alternate embodiment, the processing system 500 may be embodied as the wearable device 202 of the sleep monitoring platform 200. As a further example, the processing system 500 may be embodied as a combination of the backend system 208 and the wearable device 202 or the secondary device 204 of the sleep monitoring platform 200 depicted in FIG. 2, or a combination of the wearable device 202, the secondary device 204, and the backend system 208. Referring to FIG. 5, in various embodiments, the processing system 500 may be used to implement computer programs, logic, applications, methods, processes, or software to label sleep states and provide other functionality, as is described in more detail below.

As FIG. 5 shows, the processing system 500 may include a set of one or more motion sensors 502, a set of one or more optical sensors 504, a feature generation module 506, a sleep stage classifier module 508, and a rule engine 510. The set of one or more motion sensors 502 may be a module configured to generate motion data that characterizes the movement experienced by the wearable device 202. In some cases, the set of one or more motion sensors 502 may be one or more accelerometers, e.g., a tri-axial accelerometer, and the motion data may be data that characterizes the acceleration experienced by the wearable device 202, including acceleration due to gravity. Other examples of motion sensors include gyroscopes or magnetometers. In some cases, the motion data may be pre- or post-processed to remove noise or otherwise facilitate the characterization of the movement experienced by the wearable device.

The data that is obtained from the motion sensors may generally take the form of one or more time series that represents acceleration, or other motion-related parameter (e.g., rotation or movement relative to the Earth's magnetic field), along one or more axes. Such data may be pre- or post-processed in order to remove artifacts, fill in missing data points (via interpolation, for example), smooth out or reduce noise, etc. prior to feature extraction. In some implementations, some post-processing may actually be part of the feature extraction process that is discussed in more detail below. For example, motion data may be quantified into a movement measure or movement index over a given time period. Thus, a movement measure or index, as used herein, may refer to some quantification of movement over a time period. The movement measure may quantify the movement along a single axis or multiple axes (e.g., an X axis, a Y axis, and/or a Z axis. Examples of movement measures are described in greater detail in U.S. patent application Ser. No. 14/859,192, filed Sep. 18, 2015, which is hereby incorporated by reference herein.

The set of one or more optical sensors 504 may be a module configured to generate heart rate data, e.g., the one or more optical sensors 504 may serve as a heart rate sensor of the wearable device 202. The heart rate data may be referred to herein as "pulse-related data" since it characterizes physiological phenomena that are driven by pulsatile behavior in a person's circulatory system.

By way of example and not limitation, the set of one or more optical sensors may be a set of one or more photoplethysmographic sensors that generate one or more time series data of pulse-related data. The pulse-related data may take the form of a waveform of detected light that varies in response to the blood volume pulsating within the skin of a wearer of the wearable device due to the wearer's heartbeat. Similar to the motion data generated at operation 302, the pulse-related data may be pre- or post-processed to remove noise or artifacts, smooth out the data, or to otherwise enhance the data in some way. For example, in some cases, the pulse-related data may be pre-processed to remove noise or motion artifacts. Additionally or alternatively, in some cases the pulse-related data may be post-processed to extract pulse-to-pulse intervals, optical-data amplitude data, or some combination thereof, e.g., as part of the feature extraction processes discussed in more detail below.

Feature Extraction & Sleep Stage Classifier

The feature generation module 506 may be a module, e.g., computer-executable instructions stored on a non-transitory, machine-readable medium, such as a disk drive, configured cause one or more processors to derive a set of one or more data-driven features from the motion data and the pulse-related data for a given time window or time windows associated with a particular time period. Examples of such features may include a cumulative movement index extracted from the motion data, a time elapsed since a significant movement extracted from the motion data, a time to a next significant movement extracted from the motion data, a time to a nearest significant movement extracted from the motion data, a variability, as assessed by sample entropy, of inter-beat intervals extracted from the pulse-related data or of the amplitude of the pulse-related data, a root mean square deviation of the pulse-related data, a root mean square of the inter-beat intervals, a low-frequency spectral power or spectral power density of the inter-beat intervals extracted from the pulse-related data or of the pulse-related data, a high-frequency spectral power or spectral power density of the inter-beat intervals extracted from the pulse-related data or of the pulse-related data, a variability of an envelope of the pulse-related data, a variability of an envelope of the inter-beat intervals, a variability of a de-trended respiration rate extracted from the pulse-related data, an inter-percentile spread of a heart rate extracted from the pulse-related data or from the inter-beat intervals, a normalized de-trended heart rate extracted from the pulse-related data or from the inter-beat intervals, and a cross-correlation of each pulse shape of one or more pulse shapes in the pulse-related data with a previous pulse shape in the pulse-related data (in which case the pulse shapes may be normalized to a common duration prior to the cross-correlation). Additionally or alternatively, similar features may also be extracted from the amplitudes of the pulse-related data (or the motion data) in a similar manner, e.g., instead of a series of inter-beat intervals, a series of amplitudes may be analyzed and features extracted therefrom. Each amplitude in the series may, for example, correspond to an amplitude metric for an individual heartbeat pulse. For example, in some embodiments, the peak amplitude in the PPG signal during a heartbeat may be used as the amplitude metric for feature extraction purposes. Alternatively, the average amplitude in the PPG signal during a heartbeat may be used as the amplitude metric for feature extraction purposes. Various specific examples of features that may be extracted from motion data and pulse-related data are discussed below in more detail.

For example, a cumulative movement index may be obtained by integrating the acceleration signal or other signal indicative of movement (which may optionally be smoothed and/or rectified before integration) from an accelerometer or accelerometers or other motion sensors over a given time window to obtain the area associated with the accelerometer signal—this area may then be mapped to a motion index, e.g., if the integrated signal is less than a first threshold, then the cumulative movement index may be 0; if the integrated signal is greater than or equal to the first threshold but less than a second threshold, then the cumulative movement index may be 1; if the integrated signal is greater than or equal to the second threshold, but less than a third threshold, then the cumulative movement index may be 2, and so forth. The integrated signal for an epoch can be called an "activity count". The total number of counts produced by the motion sensor(s) during the time period may be used to obtain a measure of how active the subject was. For example, the more active the person is, the more movement and acceleration will be detected, which may increase the total counts produced by the motion sensor(s) during that time period. In a sense, the total counts of a plurality of time periods may be proportionate to the integrated signals for those time periods. In another embodiment, another cumulative movement index may be determined by evaluating the percentage of an epoch during which the magnitude of the motion data was above a pre-set threshold. There are multiple ways in which the counts produced by a motion sensor over a time period may be used. For example, an activity count based on an acceleration signal for a 30 second epoch may be obtained by counting the number of times the acceleration signal crosses a pre-determined threshold in a positive-going direction. Alternatively, count may be evaluated by counting the number of times the signal in question crosses the x-axis, i.e., zero-crossings, in an epoch. These are just some of the examples of ways that an activity count may be generated and used to produce a cumulative movement index, and it is to be understood that the present disclosure is not to be limited to only these examples.

If multi-axis accelerometers are used, then the acceleration that is used to generate the motion feature may be the absolute combined magnitude of the multiple axes, e.g., the total acceleration magnitude rather than multiple component magnitudes.

The cumulative movement index may then be used, for example, as a benchmark for determining if a significant movement has occurred. For example, one feature that may be extracted from the motion data is how long it has been, either in absolute time or in terms of the number of time windows or time periods over which each cumulative movement index is calculated, since the last time window or time period that the cumulative movement reached or exceeded a particular value. For example, a time window or time period is deemed to have had a significant movement if it had a cumulative movement index of 3 or more, then the amount of time since the last significant movement may be evaluated by determining how much time has elapsed or, alternatively, how many time periods have elapsed, between the time period for which features are being extracted and the last time period or time window that occurred which had a cumulative movement index greater than or equal to 3. This same technique may also be forward-looking, e.g., the number of time periods or time windows between the time period or time window for which features are currently being determined or extracted and the next time window or time period that has a cumulative movement index greater than or equal to 3. Such analysis may be performed because the feature extraction may be performed well after the data from which the features are extract has been collected, thereby allowing features to be extracted for time periods or time windows based on data from the time period or time window in question and/or time periods or time windows both before and after the time period or time window for which features are being determined.

Figure 6:
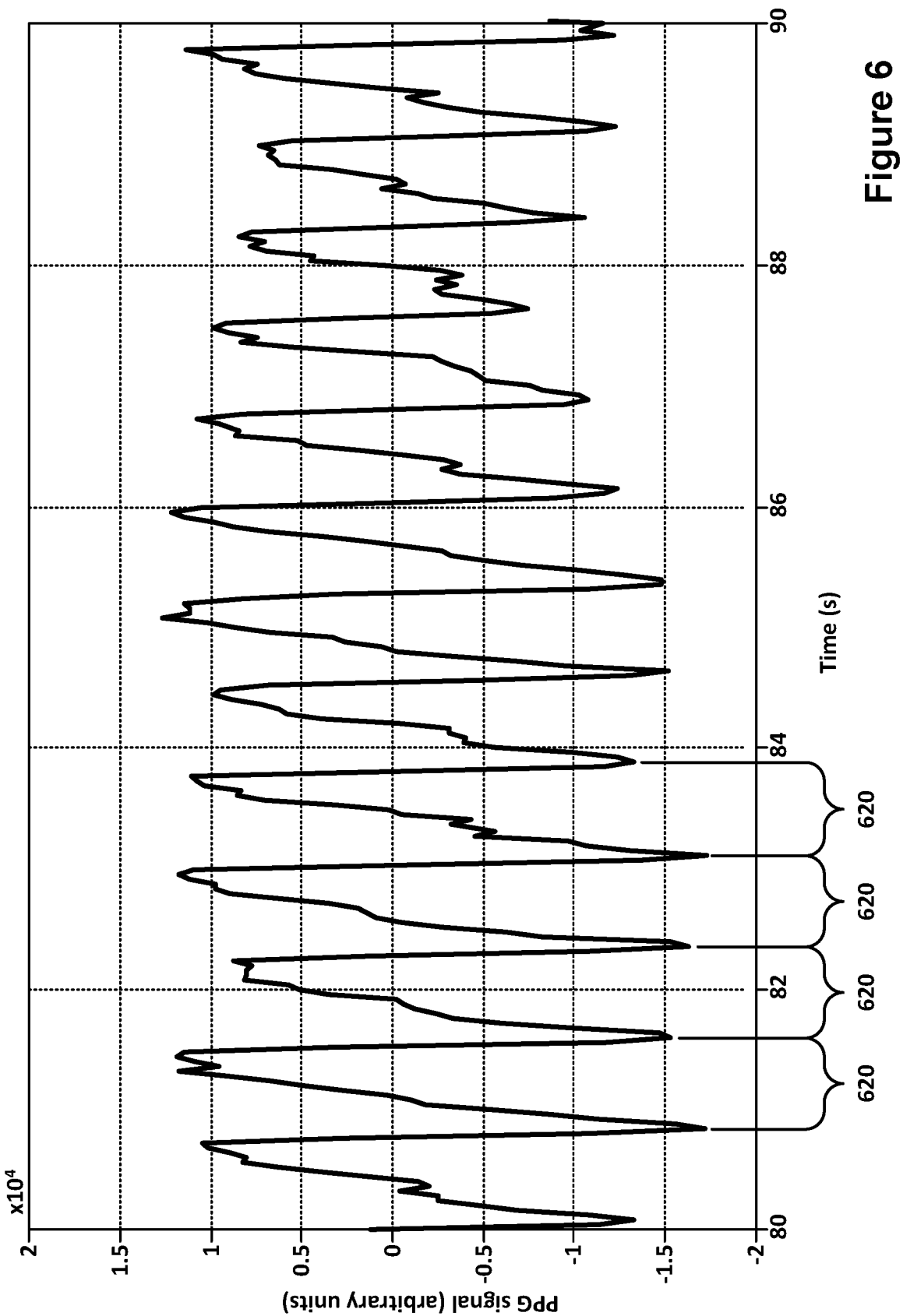
FIG. 6 depicts an example photoplethysmogram (PPG) signal.

A number of features may be extracted from the pulse-related data as well; features extracted from pulse-related data may be referred to herein as "pulse data features." A typical photoplethysmographic (PPG) signal, such as may be output by an optical heart rate sensor such as those discussed herein, may provide a periodic signal that indicates heart rate. The PPG signal is typically the voltage measured by an optical heart rate sensor and reflects the volume changes of blood passing through blood vessels in the tissue under the sensor. As the heart beats, the volume of blood in the blood vessels changes with each beat. Thus, the peak/trough pattern seen in the raw PPG signal reflects the underlying heartbeats of the person. By detecting the peaks (or, alternatively, the troughs) of the PPG signal, the person's cardiac activity can be determined. FIG. 6 depicts such a PPG signal. Such a signal is typically analyzed to determine how many peaks in the signal occur within a given interval, e.g., if 70 peaks occur within a 1-minute interval, then this indicates a heart rate of 70 beats per minute; this is one example of an extracted feature from the pulse-related data. A peak-counting algorithm may be used to determine the locations of the peaks, e.g., the data may be analyzed to find maximum or minimum values within specified windows of time. For example, a window of time may be defined between every time the PPG signal exceeds a certain level and then subsequently falls below another level—the maximum value within that window of time may be identified as a "peak." The identified peaks may also be checked to ensure that they are "physiologically reasonable," i.e., they are not too far apart or close together that they would be physiologically impossible. There are many techniques for identifying peaks, and the present disclosure is not limited to any particular such technique.

Figure 7:
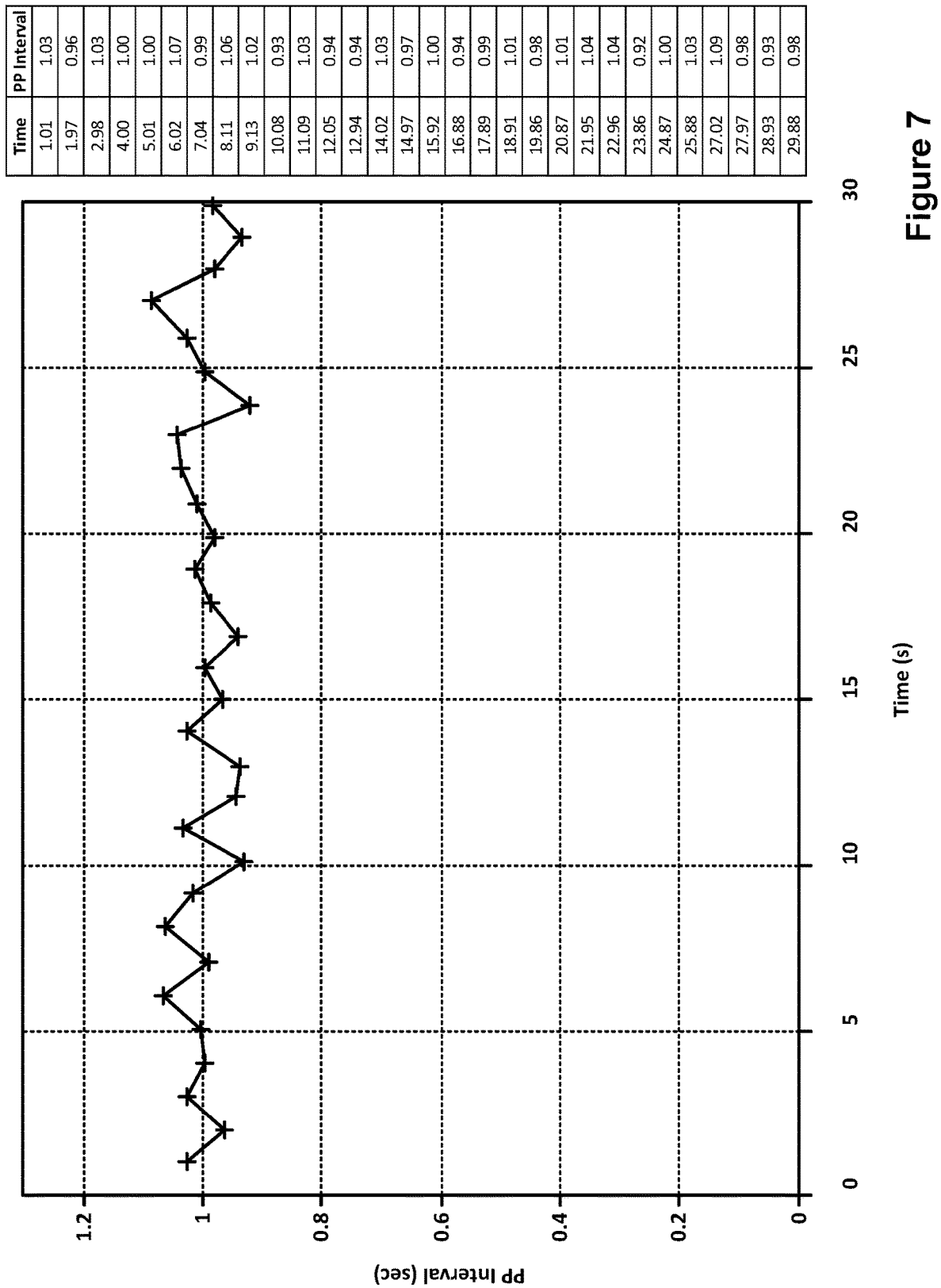
FIG. 7 depicts a plot of example inter-beat interval duration over time.

Another feature that may be extracted is a series of inter-beat intervals, i.e., the times between each adjacent pair of peaks; the inter-beat intervals may also be referred to as "PP intervals". For context, these PP intervals derived from the photoplethysmogram may be considered equivalent to the "RR interval," which is the time between QRS complexes in an electrocardiogram. The QRS complex is a term of art used to refer to a combination of three specific and successive signal behaviors that are seen in a typical electrocardiogram. The only minor difference between the PP interval and the RR interval is when there is slight modulation of the pulse transit time (PTT), which can occur to a small extent. However, to a good approximation the PP interval series is equivalent to the RR interval series, and may thus be used as a substitute for electrocardiogram measurements. In FIG. 6, there are four inter-beat intervals 620 indicated, although each pair of adjacent peaks would have its own associated inter-beat interval. Thus, for example, if there are 70 heart beats in a minute, there may be 69 inter-beat intervals that are within that 1-minute period. The inter-beat intervals may be another source of features. For example, the variation in the inter-beat intervals for a given time period or time window may be evaluated using any of a number of different techniques, in order to obtain various features for that time period or time window. FIG. 7 depicts a plot of inter-beat interval duration over time; as can be seen, the inter-beat interval durations in this example time period vary from 0.92 seconds to 1.09 seconds.

The main influences on the PP interval are the parasympathetic nervous system (the activation of which tends to slow the heart rate and hence lengthen PPG pulses), and the sympathetic nervous system (the activation of which tends to speed up the heart and shorten the PP interval), which together make up the autonomic nervous system. The parasympathetic and sympathetic nervous systems can operate on slightly different timescales (specifically, the parasympathetic nervous system can operate on a very short time scale and produce effects on the next heartbeat after the parasympathetic nervous system is activated, whereas the sympathetic system is mediated through acetylcholine and it takes multiple heartbeats before heartrate changes triggered by the activation of the sympathetic nervous system take effect). One way to capture this difference is to take the spectral density of the PP interval series using a technique called Heart Rate Variability (HRV) analysis. The higher frequency, e.g., between 0.15 and 0.4 Hz, components of the spectrum may reflect the parasympathetic activation since they correspond to short time scales, while the lower frequency, e.g., 0.04 to 0.15 Hz, components may reflect both parasympathetic and sympathetic nervous system effects. Thus, power in the HF band may be ascribed to parasympathetic activation and power in the LF band may be ascribed to a mixture of sympathetic and parasympathetic nervous system activation.

One aspect of this technique is that the sleep stage of the person is reflected in the degree of activation of their sympathetic and parasympathetic nervous systems. Thus, the HRV parameters may reflect information about the sleep stage that may be used by the classifier to differentiate between different potential sleep stages.

As mentioned earlier, at least two general categories of information can be extracted from the pulse-related data. Firstly, features related to heart rate variability (HRV) may be extracted by identifying the RR intervals (an RR interval is measured in seconds and is the time between the successive peaks of the PPG signal), as is discussed above. The HRV may vary depending on the stage of sleep, e.g., in deep sleep the heart rate slows, and the degree of respiratory sinus arrhythmia will increase (respiratory sinus arrhythmia is a naturally occurring variation in heart rate that occurs throughout a breathing cycle). These physiological effects can be measured quantitatively, for example, by measuring the heart rate and measuring the high-frequency component of the HRV parameters, e.g., in the 0.15 to 0.4 Hz frequency range.

Figure 8:
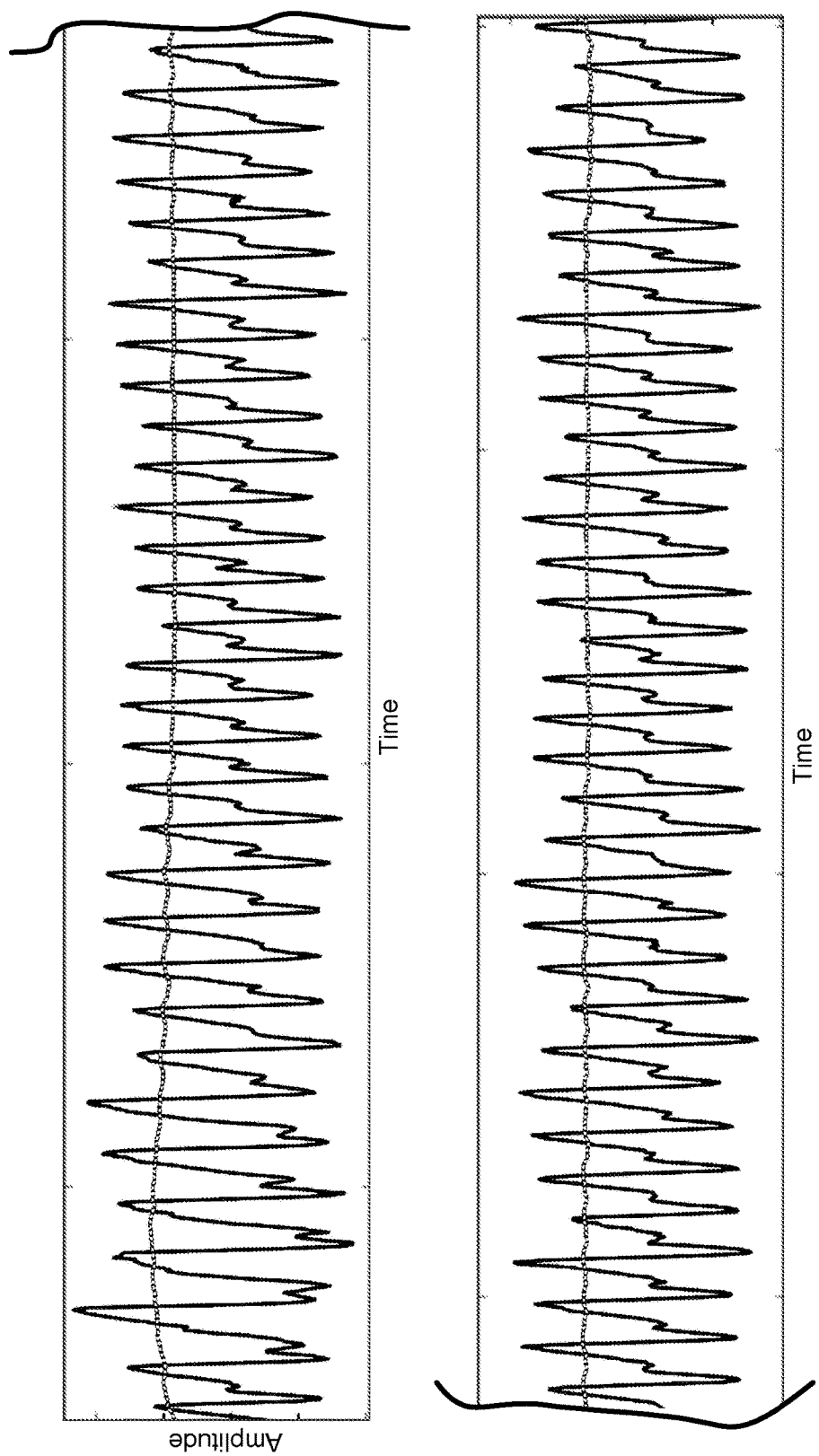
FIG. 8 depicts an example PPG signal plot and signal envelope.

Secondly, the changes in the envelope and shape of the PPG AC amplitude may be extracted. As noted earlier, the amount of light that is diffusively reflected out of a person's skin and detected by a PPG sensor varies in time with the person's pulse or heart rate; the time-varying aspect of such a signal is referred to as the "AC" component, and the "constant" portion of such a signal is referred to as the "DC" component. The AC amplitude may be determined by subtracting the DC component from the overall amplitude of the signal, and is often colloquially referred to as the "PPG amplitude." The PPG amplitude is determined by the volume of blood in the tissue under the optical sensors, which is, in turn, determined by the compliance of the arteries in the tissue. This arterial compliance is under the active control of the sympathetic and parasympathetic nervous system, which are ultimately under the control of the autonomic nervous system, so the amplitude of the PPG reflects the activity of the central nervous system (CNS), which, in turn, is associated with sleep stage. In general, there is no parasympathetic nervous system activation of blood vessels (except in some special locations), but sympathetic activation of the blood vessels does occur and has the effect of making the vessels constricted. This can be seen in a photoplethysmogram signal, as shown in FIG. 8, where there is modulation of the amplitude of a PPG signal over the approximately 60 seconds shown in the diagram. The amount and variability of this modulation is associated with sleep stage, and therefore may provide a useful feature for use with the classifier. In FIG. 8, the envelope of the power of the signal has been extracted by calculating the root mean square power of the signal over a window of approximately 5 seconds, and displaying that as the dotted line (the underlying PPG signal is a solid black line). There are multiple alternate ways to calculate the envelope of the signal, e.g., taking the Hilbert transform of the signal, or using a peak sample and hold approach, followed by low pass filtering. Regardless of method, the raw PPG signal can then yield a new signal called PPGE where PPGE denotes PPG envelope. Features, such as the standard deviation of the PPGE signal, can then be extracted from the PPGE signal for each epoch.

Various examples of features that may be extracted from the pulse-related data are discussed below, although this is not an exhaustive discussion, and additional features may be extracted for use with the classifier as well. In some embodiments, sample entropy may be used to assess the variability in inter-beat intervals to provide another feature that may potentially be used by a classifier to classify a given time period or time interval's sleep stage.

Another pulse data feature that may be used is the root mean square deviation of the pulse related data or of the inter-beat intervals. A further pulse data feature that may be used for classification purposes is the spectral power of the series of inter-beat intervals for a time period or time window for which features are being determined. The spectral power may be determined over a range of frequencies, e.g., over a low frequency range (0.04 Hz to 0.15 Hz, for example, may be considered "low" frequency for the purposes of heart rate data analysis) or over a high frequency range (0.15 Hz to 0.4 Hz, for example, may be considered to be "high" frequency for the purposes of heart rate data analysis). Thus, high-frequency spectral power of the inter-beat intervals may be determined by integrating the spectral power density of the inter-beat intervals over a frequency range spanning between 0.15 Hz and 0.4 Hz.

Further examples of pulse data features include features based on respiration-related phenomena. For example, a PPG signal may incorporate dominant periodic elements that are attributable to both heart-rate-related physiological phenomena and to respiratory-related phenomena. Thus, for example, if a PPG signal exhibits a large frequency component in the 60 Hz to 90 Hz domain, this frequency component is likely to be indicative of heart rate and the periodicity of such a component may be used to determine inter-beat intervals. However, that same PPG signal may also have a large frequency component that is more in the range of 6 Hz to 15 Hz, which may be indicative of respiratory rate. Thus, a PPG signal may be used to estimate both heart-rate-related parameters and respiratory-rate related parameters.

Figure 9:
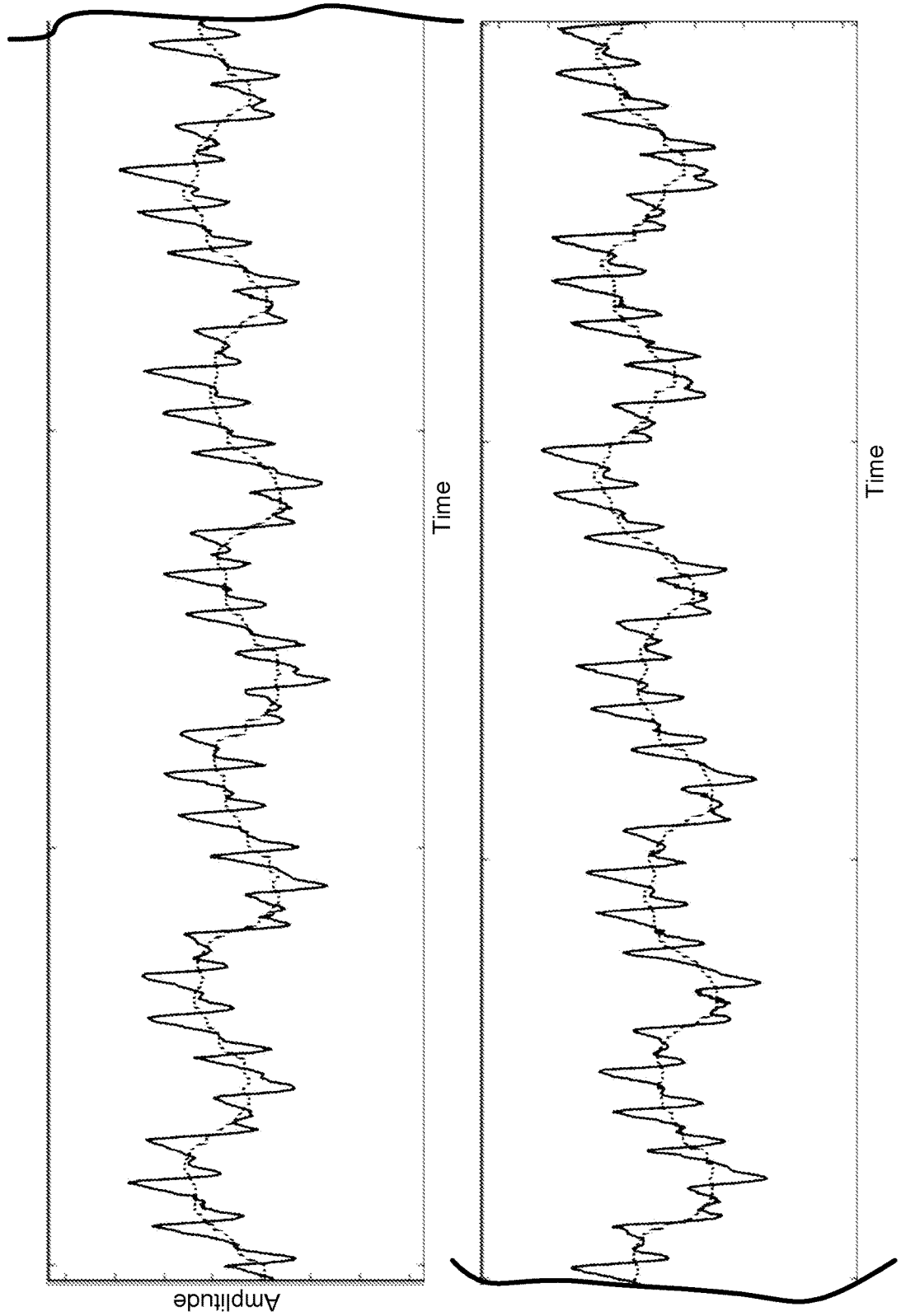
FIG. 9 depicts an example PPG signal plot with a heart-rate-related component and a respiratory rate component shown.

For example, FIG. 9 depicts pulse-related data from a PPG sensor over approximately a sixty-second time window. As can be seen, there is a higher-frequency heart rate signal (solid black line) that is riding on top of a lower-frequency respiration rate signal (dotted line); in this example, the heart rate over this interval is 62 beats per minute, whereas the respiration rate is 13 breaths per minute. Respiration rate (and features extracted therefrom) may serve as a useful discriminant for a sleep stage classifier, as the variability and absolute value of the respiration rate may be related to sleep stage. In deep sleep, respiration rate is very stable and hardly varies (e.g., may stay within 0.5 breaths per minute). In REM sleep, conversely, respiration rate can be quite variable. Thus, the variability of the respiratory rate may prove to be a valuable feature for use in a sleep stage classifier.

Other features that may be determined or extracted by the feature extractor may include, for example, inter-percentile spreads of various parameters. For example, the spread between the $10^{th}$ percentile inter-beat interval duration and the $90^{th}$ percentile inter-beat interval duration during a given time period or time window may be used as a feature. Another feature that may be extracted is the amount of cross-correlation between optical pulse rate signal shapes in a series of data pulses, i.e., a quantification of how similar each pulse shape is compared to the previous pulse shape in a series of pulse shapes. In determining such a feature, the feature extractor may first normalize each pulse shape to have the same duration to allow for a more accurate correlation based on shape.

Returning back to the processing system 500, the classifier module 508 may be a module configured to classify or otherwise label periods of time with a given sleep state based on the one or more features derived from the motion data and the heart rate data. The classifier module 508 may, for example, apply any of several classifier techniques to the features for a given time period or time window in order to determine a sleep stage classification for that time period or time window. Example classifier techniques that may be used may include, for example, nearest neighbor classifier, random forest classifier, support vector machine, decision tree, neural networks, and linear discriminant classifiers. Various classifiers identified and discussed, for example, in "Comparison of 14 different families of classification algorithms on 115 binary datasets" by Jacques Wainer (Computing Institute, University of Campinas, Campinas, S P, 13083-852, Brazil, Jun. 6, 2016) may be used as classifiers in the context of this disclosure. The present inventors have found that such classifiers may be trained, as discussed earlier, using features extracted from motion and pulse-related data collected during sleep sessions that are conducted under the oversight of professional or trained sleep scorers using specialized equipment and in-depth analysis of each time interval being evaluated—such data may be referred to herein as "benchmark" motion data and/or pulse-related data. Thus, for example, the features extracted from motion and pulse-related data collected during time periods or time windows that have been assigned, by a sleep scorer, a sleep stage of "deep sleep" may be used to train the classifier to assign a "deep sleep" classification to time windows or time periods having features that match the criteria of the classifier developed during such training. The classifier is initially built and tested on benchmark data using cross validation techniques such as k-fold cross validation and leave-one-out cross validation.

Figure 10:
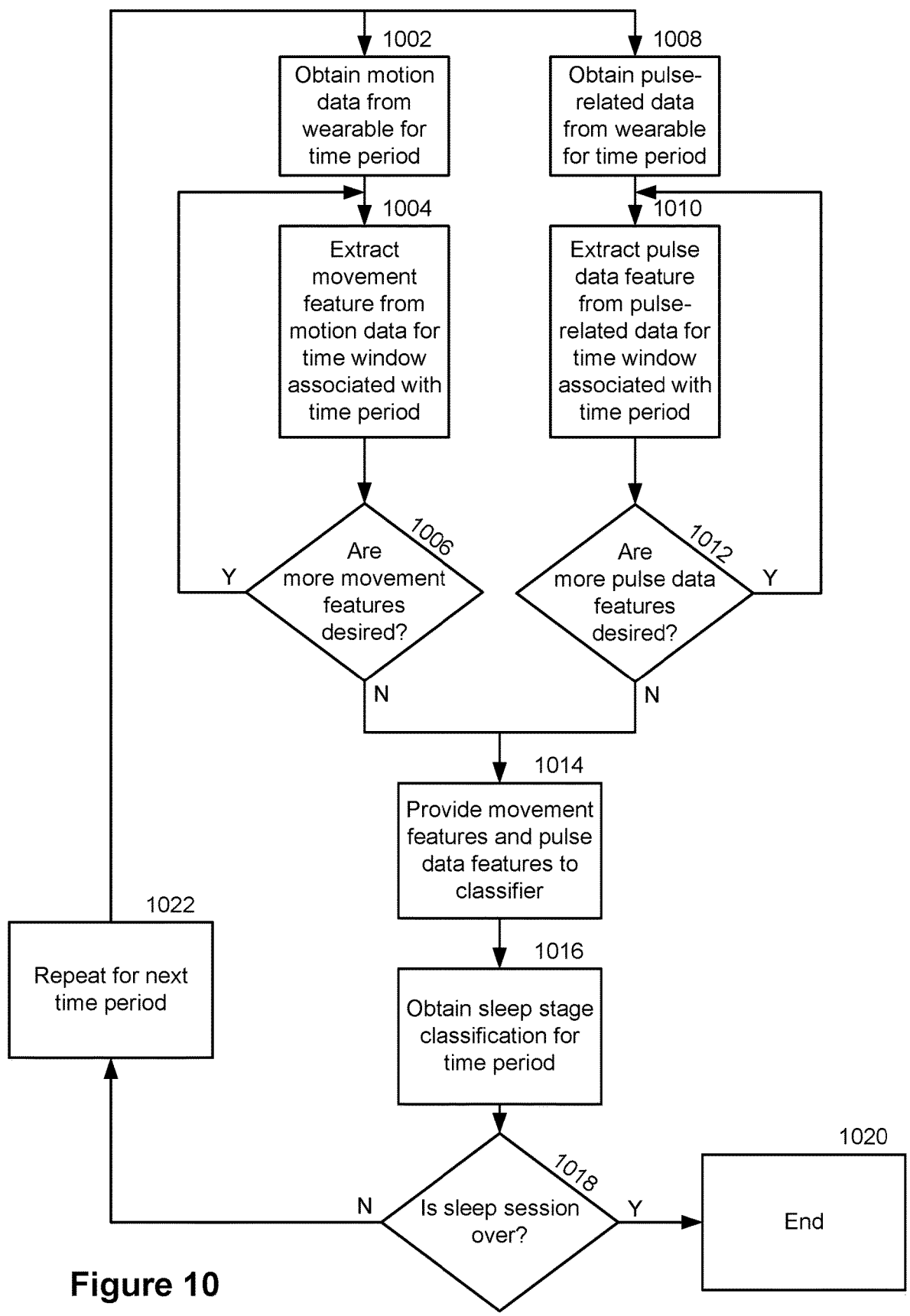
FIG. 10 depicts a flow diagram of a technique for classifying the sleep stages of time periods.

FIG. 10 depicts a flow diagram of a technique for classifying the sleep stages of time periods, e.g., 30-second or 60-second epochs (the epochs may be selected to be of any desired duration, although 30-second epochs are commonly used). In block 1002, motion data for a given time period may be obtained, e.g., from an accelerometer or other motion sensor. In block 1004, a movement feature for that time period may be extracted from the motion data for a time window associated with that time period. For some features, the time window may be coextensive with, i.e., the same as, the time period, but for other features, the time window may be larger than the time period and may or may not overlap with the time period. For example, a "time until last significant movement" feature may, in many cases, involve motion data from a time window that spans multiple time periods. In such cases, the motion data that is obtained in block 1002 may be obtained for all of the time periods that are within the time window. The movement feature that is extracted may be determined, for example, as set forth with respect to the movement features discussed above, or using other techniques. The technique may then proceed to block 1006, in which a determination may be made as to whether further movement features are to be determined for the time period for which features are being extracted. If so, then the technique may return to block 1004, where another movement feature may be extracted. If all movement features have been extracted, then the technique may proceed from block 1006 to block 1014.

The technique may also include, in block 1008, obtaining pulse-related data from the heart rate sensor for the time period in question. In block 1010, a pulse data feature for the time period may be extracted from the pulse-related data for a time window that is associated with that time period. As with the extraction of the movement features, the time window in question may be coextensive with the time period, or may, for some pulse data features, span multiple time periods and may or may not overlap with the time period for which the feature is being extracted. For example, heart rate variability (HRV) for a time period may be determined using the pulse-related data for a time window that includes the time period in question as well as the two time periods immediately preceding that time period and the two time periods immediately following that time period, i.e., five time periods. Thus, the pulse-related data that is obtained in block 1008 may be obtained for multiple time periods if the time window in block 1010 spans multiple time periods. Once the pulse data feature has been obtained in block 1010, e.g., such as is discussed earlier herein, the technique may proceed to block 1012, in which a determination may be made as to whether further pulse data features are required. If it is determined in block 1012 that further pulse data features are required, then the technique may return to block 1010 for further pulse data feature extraction. If it is determined in block 1012 that no further pulse data features are required, then the technique may proceed to block 1014.

It is to be appreciated that operations 1002 and 1008 may be executed substantially in parallel. Such may be the case where the set of one or more motion sensors and the set of one or more optical sensors are active during the same time period to generate sensor data (e.g., motion data and pulse-related data) that characterizes that time period. It is to be appreciated that, in some cases, a microprocessor may interleave or time slice execution of processing (e.g., using threads if an embedded operating system is executing on the microprocessor or a series of interrupt handlers if the sensor data processing executes on bare metal) the samples generated by the set of one or more motion sensors 502 and the set of one or more optical sensors 504. Thus, in some cases, although the sensors may be concurrently active, the microprocessor (in a single-core or multi-core embodiment) may interleave execution of the processing of the sensor data. Such processing of the sensor data may include storing the samples in a corresponding data structure, cleaning up the signal, transforming the data into a different format (e.g., encoding the data into a comparatively smaller data representation), or any other suitable process. It is also to be understood that other operations discussed with respect to the techniques presented herein may also be performed in parallel with each other as well, e.g., feature extraction may be performed for multiple different features simultaneously.

The determination of whether further features need to be extracted in blocks 1006 and 1012 may be made on a situational basis or based on a predetermined definition of which features are deemed necessary in order to perform classification. For example, a random forest classifier may compare certain features against particular criteria at each branch of a decision tree to determine which feature to compare against a criterion in the next branch. Depending on the branches taken in the classifier, certain features may not be required in order to reach a final determination—only the features needed in the branch nodes of the classifier that are used in a classification determination may be determined for a given time period. As a result, feature extraction may be performed on an as-needed basis, if desired, to avoid unnecessary feature extraction, which may conserve CPU resources and power. Alternatively, there may be a predetermined set of movement and pulse data features that may be determined for every time period that is classified by the classifier.

One challenge that may be encountered during classification by the classifier using the extracted features is that some features may exhibit significant variation from person to person, e.g., average heart rate may vary wildly within a population. This may make it difficult for the classifier to provide accurate results. In order to address such variability, some of the extracted features may be normalized (both during training and during classification). In particular, such features may include features extracted from heart-rate-related data, e.g., heart rate, the standard deviation of the heart rate over the epoch, the average value of the PP interval or inter-beat intervals over the epoch, the standard deviation of the PP interval or inter-beat intervals over the epoch, the difference between the $90^{th}$ percentile value and the $10^{th}$ percentile value of the PP interval or inter-beat interval during the epoch, the power in the low-frequency and/or high-frequency bands of an HRV analysis performed on the epoch and some additional adjacent epochs, the ratio of the low frequency power to the high frequency power for the epoch, the percentage of the low-frequency power and/or the high frequency power with respect to the total HRV power. In order to normalize such features, the PP intervals or inter-beat intervals may be normalized or scaled such that over the entire sleep session being analyzed, the average PP interval or inter-beat interval has the same value as the average PP interval or inter-beat interval for the other sleep sessions that are used to train the classifier (the same applies to the data for the sleep sessions used to train the classifier). Thus, for example, the PP intervals or inter-beat intervals may be normalized so that the average PP interval value for a given sleep session is equal to 1. By normalizing the inter-beat interval series, the other features that are extracted based on the normalized inter-beat interval series will also be normalized.

Figure 11:
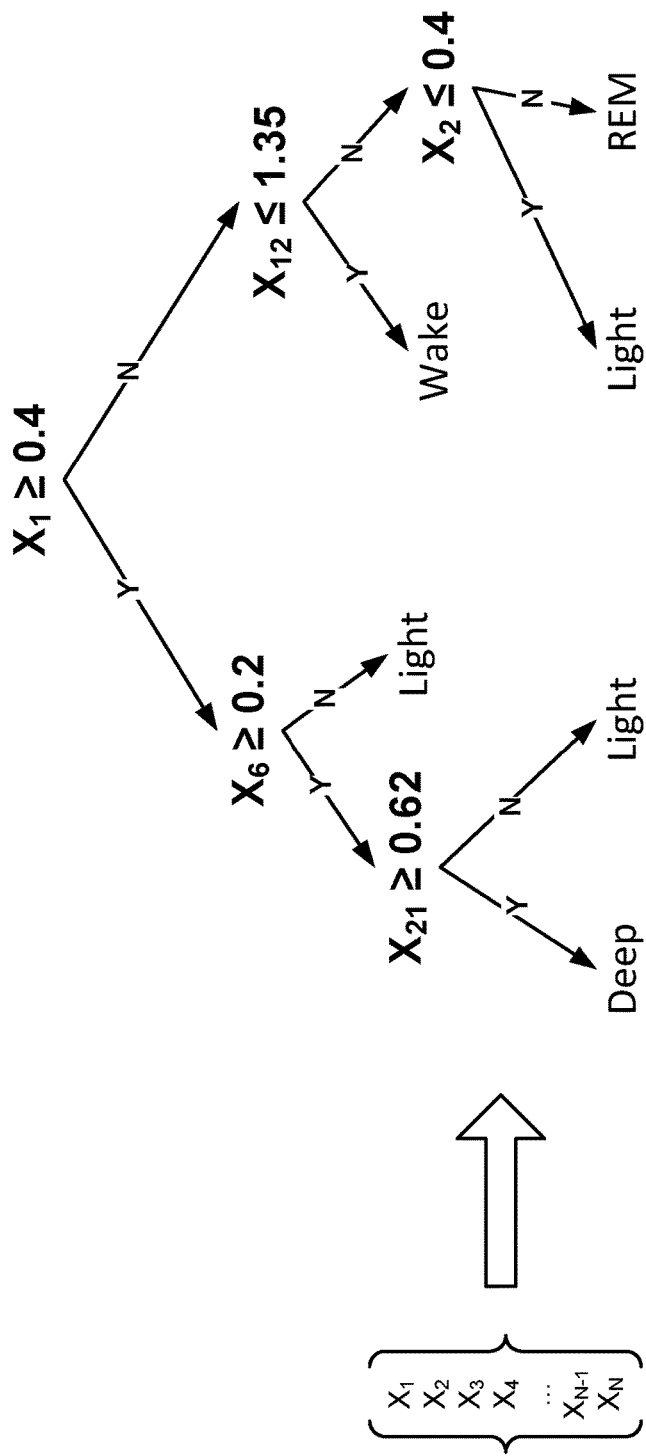
FIG. 11 is a notional example of a random forest decision tree classifier.

Once sufficient movement and pulse data features have been extracted in blocks 1004 and 1010, such features may be passed to the classifier in block 1014. The classifier 1014 may select various features from the pool of movement features and pulse data features for the time period and compare them against various criteria in order to assign a sleep stage classification for that time period in block 1016. FIG. 11 is a notional example of a decision tree classifier in which different features selected from a set of features $\{X_1, X_2, X_3, X_4, \ldots X_{N-1}, \text{ and } X_N,\}$ are evaluated at different levels of a branching decision tree in order to determine which branches to take next and, ultimately, which sleep stage classification to assign.

As discussed earlier, classifiers such as decision trees may be "trained" using empirical data. For example, a sleep stage classifier may be trained by having a set of labeled data available, labels for epochs as being Wake, Light, Deep or REM (or whatever sleep stages are desired, e.g., there may be different labels or additional labels, such as artefact and/or off-wrist labels). Each epoch may have a set of attribute values or features associated with it (labeled $X_1$, $X_2$, $X_3$ etc.). The decision tree can be "trained" by splitting the source set of labels into subsets based on an attribute value test on one of the features. For example, if one were to start with 1000 labeled epochs, it might be determined that using the rule $X_1>0.4$ divides the original set of labeled epochs into a subset with 250 epochs in one branch, and 750 epochs in another, but that the set of 250 contains most of the Deep sleep epochs. This would mean that the rule $X_1>0.4$ is generally useful for recognizing deep sleep epochs. The choice of the threshold value (0.4 in this example) may be optimized by maximizing the overall accuracy of the decision rule for classifying deep epochs versus non-deep epochs in this example split. The subset of 250 epochs could then be further refined into a more accurate classification (e.g., $X_6>0.2$ recognizes most of the Light sleep epochs in the subset of 250 epochs that contains most of the Deep sleep epochs. This process may be repeated on each derived subset in a recursive manner called recursive partitioning. The choice of which feature to use at any split in the tree during training may be done randomly, and the choice of the threshold value may be chosen to maximize the classification accuracy of the chosen subset. An optimal decision tree may therefore be arrived at by multiple random iterations of the chosen feature partitions (a feature partition, in this case, may be thought of as a logical test that involves a particular feature or attribute and a threshold value). The recursive partitioning may be stopped when there is no improvement (or improvement that is below a desired minimum amount of improvement) in classification accuracy resulting from further recursion. Once feature partitions have been identified that provide a desired degree of classification accuracy relative to the training dataset (1000 labeled epochs in the above example), a decision tree using the same feature partitions may be used to classify sleep stages for epochs from other datasets.

Decision trees are effective classifiers, but may suffer from "overtraining" in which they provide rules that are too heavily dependent on the training data used to define them. A classifier technique which builds on decision trees is called a random forest classifier. A random forest classifier is formed by generating multiple decision tress randomly as described above. These decision trees can then be combined to form an overall weighted set of decisions using majority voting or the like.

The simple decision tree classifier or random forest classifier may be executed by the wearable device or may, in some embodiments, be executed by the secondary device or by the backend system. In such latter cases, the extracted features may be transmitted from the wearable device to the secondary device or the backend system, or from the secondary device to the backend system.

For a system in which a random forest classifier has been trained as described above, an example set of features for use in the classifier that may provide good classification performance may include: time elapsed since last movement above a pre-set threshold (e.g., time since last epoch with a movement index above the pre-set threshold), time until a next movement above a similar or different pre-set threshold (e.g., time until next epoch with a movement index above that pre-set threshold), a very low frequency component of a breathing-derived spectrum, the autocorrelation of successive RR intervals (or inter-beat intervals), the kurtosis of the successive differences of the RR intervals (or inter-beat intervals), the difference between the current breathing rate and the breathing rate calculated over a one-hour window, and the $90^{th}$ percentile of the heart rate and/or the RR intervals (or inter-beat intervals).

The very low frequency component of a breathing-derived spectrum may, for example, be derived by first filtering the pulse-related data collected by a PPG sensor, for example, using a bandpass filter that is configured to pass through data that occurs at frequencies typically associated with respiratory behavior; the breathing-derived spectrum may then be obtained from the resulting band-pass signal. A very-low-frequency component of such a spectrum may be in the 0.015 to 0.04 Hz range.

The autocorrelation of successive RR intervals (or inter-beat intervals) may be obtained by taking the indexed series of inter-beat intervals (or RR intervals) for the epoch in question and then taking the autocorrelation of that the sequence of intervals.

The kurtosis of the successive differences of the RR intervals (or inter-beat intervals) may be obtained by taking the kurtosis of the series formed by taking the differences in duration for each pair of adjacent inter-beat intervals in the series.

The difference between the current breathing rate and the breathing rate calculated over a one-hour window may be determined by taking the respiratory rate (for example, as determined using a band pass filter) for the epoch in question and then subtracting from it the average respiratory rate over a one-hour period. Time periods other than an hour may be used as well, e.g., 55 minutes, 65 minutes, etc.

The $90^{th}$ percentile of the heart rate and/or the RR intervals (or inter-beat intervals) may be determined by determining the heart rate and/or the inter-beat interval for which 90% of the heart rates and/or RR intervals (or inter-beat intervals) for the epoch in question are below.

In some embodiments, the classifier may output a confidence score for each of the sleep stages for a given interval, and the classifier may assign the sleep stage with the highest-value confidence score to the given interval. In the case of the linear discriminant classifier, for example, classes are separated by hyperplanes in the feature space. These hyperplanes define class boundaries, and the distance of data points to these boundaries determine confidence scores. For example, a data point very close to the boundary may be less confidently classified compared to a data point far from the boundary and well into one specific class region.

In block 1018, a determination may be made as to whether the sleep session being analyzed is over, i.e., have all of the time periods within the sleep session been classified. If not, then the technique may proceed to block 1022, in which the next time period to be classified may be selected, before returning to blocks 1002 and 1008. If all of the time periods for the sleep session have been classified, then the technique may end in block 1020.

The rule engine 510 may be a module configured to analyze and update the sleep stage classifications assigned to time periods by the classifier according to a set of sleep stage rules, which may also be referred to herein as "update rules" or "post-classification rules." The sleep stage rules may include data or logic that defines patterns of sleep stages that are permissible or, alternatively or additionally, permitted or prohibited sleep stage transitions, e.g., sleep stage pattern constraints. Such rules may be useful since the classifier, which classifies epochs or time periods on a per-epoch basis may not fully account for the temporal structure of the data. In particular, for human sleep, certain patterns of sleep stages are more likely than others, e.g., it is unusual to go straight from a deep sleep stage to an awake sleep stage—it is more usual to transition from a deep sleep stage to a light sleep stage. It is also unusual to have isolated epochs associated with the REM sleep stage in the middle of a sequence of epochs associated with the deep sleep stage. To account for these scenarios, the rule engine 510 may implement rules which correct for highly unlikely sleep stage sequences.

For example, the rule engine 510 may use the sleep stage rules to correct a sleep stage pattern from DWD (deep-awake-deep) for three consecutive time periods to DDD (deep-deep-deep), as the sleep stage rules may specify that sleep state W may be prohibited from transitioning to sleep state D. In another example, the rule engine may correct patterns in which a chain of multiple consecutive epochs associated with the deep sleep stage are interrupted by one or more epochs associated with the REM sleep stage. A further example is to use knowledge of physiologically normal behavior to correct patterns of behavior. As a specific example, it is physiologically unlikely that REM will precede deep sleep in a normal night's sleep, so the rule engine can penalize the probability of detecting REM in periods prior to detection of deep sleep. For example, if one or more epochs are classified as being associated with the REM sleep stage but there are no epochs (or less than a given number of epochs or a given consecutive number of epochs) classified as being associated with a "deep sleep stage" prior to the epoch(s) that are classified as being associated with a "REM sleep stage," then the epoch(s) in question may be changed from being associated with the REM sleep stage to some other sleep stage, e.g., the sleep stage of an adjoining, non-REM sleep stage epoch.

Another example of a sleep stage rule is a majority rules analysis. In a majority rules analysis, the sleep stage of the middle time interval of a series of multiple time intervals may be changed to the predominant sleep stage for the series of multiple time intervals. Other physiologically based rules may be time-based. For example, REM sleep is unlikely soon after sleep onset, so one sleep stage rule may be that epochs that are within a given time interval from the start of a sleep session may not be permitted to be associated with the REM sleep stage. Such a time interval may be based on an actual time duration or on a number of epochs—for example, if the rule is that in the first 42 minutes of sleep, a REM sleep stage is not permitted, then any 30-second epoch of the first 84 epochs of the sleep session that is classified as a REM sleep stage may have its sleep stage classification changed, for example, to the sleep stage of an adjacent, non-REM sleep stage epoch.

Figure 12:
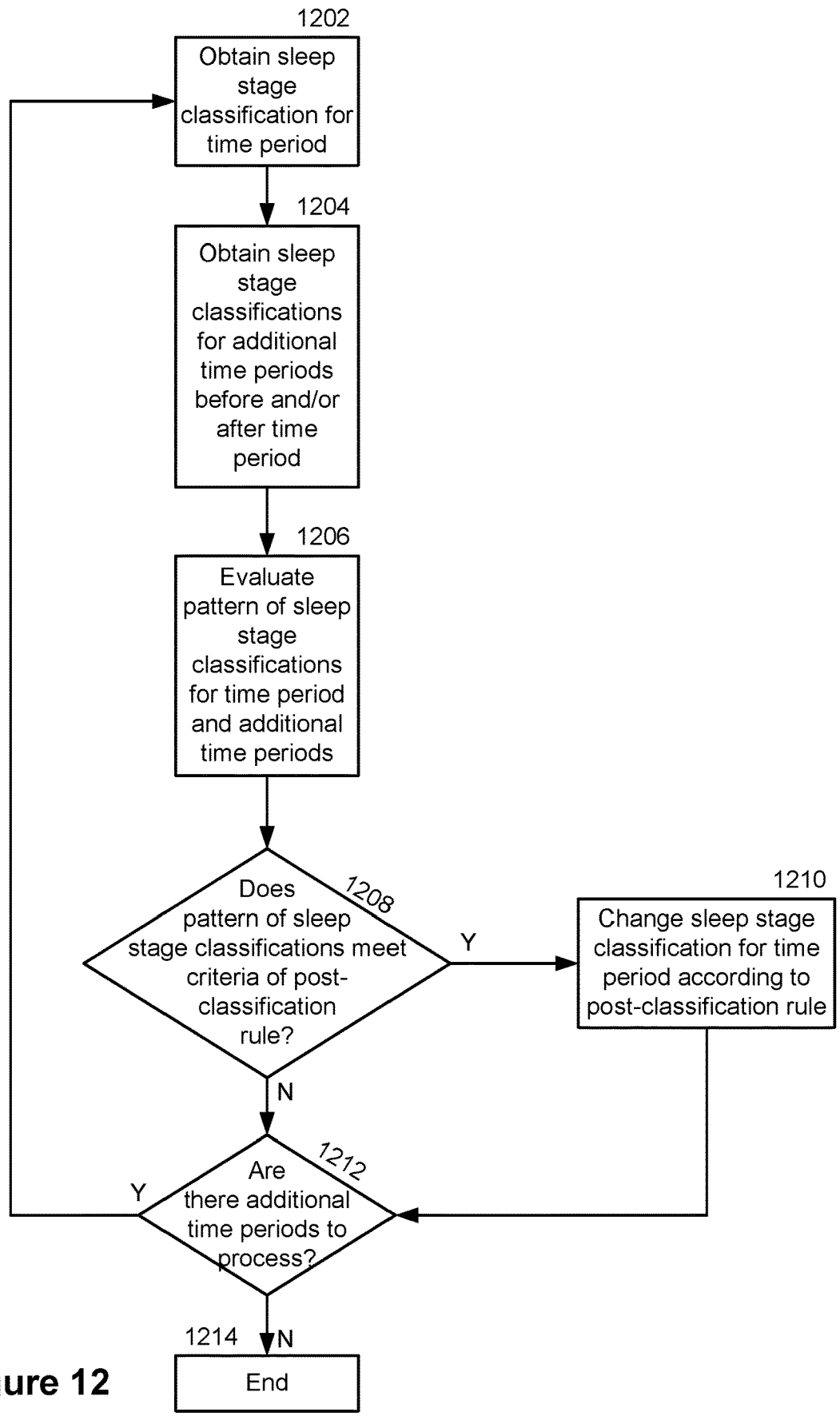
FIG. 12 is a flow chart of a technique that may be used to update the sleep stage classification, if needed, of a time period after the sleep stage classifications for time periods have been initially assigned by the classifier.

FIG. 12 is a flow chart of a technique that may be used to update the sleep stage classification, if needed, of a time period after the sleep stage classifications for time periods have been initially assigned by the classifier. The technique may begin in block 1202, in which the sleep stage for a given time period may be obtained. In block 1204, sleep stage classifications assigned to other consecutive time periods that are immediately before, immediately after, or both immediately before and immediately after the given time period may be obtained. The resulting pattern of sleep stage classifications for these multiple time periods may be determined in block 1206 and then compared against one or more criteria associated with a post-classification rule in block 1208. For example, a given post-classification rule may be that any time period that is preceded and followed by contiguous blocks of at least 3 time periods that all have sleep stage classifications that are the same but also different from that of the given time period should be re-classified to have the same sleep stage classification as the sleep stage classification of the time periods in the contiguous, adjacent blocks. If the conditions or criteria of the post-classification rule evaluated in block 1208 are met, then the technique may proceed to block 1210, in which the sleep stage classification of the given time period may be updated according to the post-classification rule, before proceeding to block 1212, where a decision may be made as to whether there are further time periods that should be subjected to post-classification rules. If it is determined in block 1208 that the post-classification rule is not met, then the technique may proceed to block 1212. If it is determined in block 1212 that further time periods are to be subjected to post-classification rules, then the technique may return to block 1202 for analysis of an additional time period. If it is determined in block 1212 that no further time periods require post-classification rule testing, then the technique may proceed to block 1214, where the technique may end.

It will be understood that the methods of FIGS. 10 and 12 may be implemented using the sleep monitoring platforms discussed earlier, e.g., the sleep monitoring platform described with reference to FIG. 2 or 3. For example, a wearable device with a motion sensor and an optical heart rate sensor, e.g., such as the wearable device 202, may be used to obtain motion and pulse-related data. The wearable device 202 may also perform some or all of the feature extraction and may, in some instances, also perform the classification functionality discussed above, as well as provide a platform for running the post-classification rules. For example, a backend system 208 may provide the parameters and classifier definition for a classifier to the wearable device 202; this may include criteria used by the classifier during classification that are learned by the classifier during training. The training may be done at the backend system, and the resulting trained classifier may then be distributed to wearable devices 202 for use by the wearable devices 202. Alternatively, some or all of the feature extraction and/or classification may be performed in a secondary device, such as the secondary device 204 or even at the backend system 208.

By way of further example, the processing system 500 may include fewer, more, or different modules apart from those shown in FIG. 5. For example, in an alternate embodiment, the classifier module 508 and the rule engine 510 may be combined into one module. In another embodiment, the classifier module 508 can be separate from and executed or processed in parallel with the rule engine 510.

It is to be appreciated that labelling a time period with a sleep state based on features derived from a set of motion sensors and optical sensors provides a comparatively useful technique to monitor sleep for a user of the wearable. Such is the case because such sensors are typically low-powered and provide comparatively comfortable tracking by a wearable device that may, for example, be strapped to the user's wrist (e.g., in the form of a watch or band).

User Interface

Once a person's sleep session has been characterized using the sleep monitoring platform and its classifier, the resulting data set for the sleep session may be broken down into various formats or analyzed and the presented to the person in order to assist them in better understanding their sleep patterns. For example, the resulting data set that is output from the sleep monitoring platform may include a start time of the sleep session in question, an end time of the sleep session in question, and the start and stop times of various intervals that have been assigned various sleep stages throughout the sleep session by the sleep stage classifier. Alternatively, the sleep session may be broken down into a standardized format, e.g., into 30-second long intervals (which may, as noted earlier, be called "epochs"), and the data set may simply list epoch numbers in which the sleep stage changed from one value to another (along with what the new value of the sleep stage is). This data may then be analyzed to produce various meta-statistics about the sleep session in question, e.g., by counting the number of deep sleep epochs, the person's total deep sleep time can be determined. The percentile breakdown of sleep stages in a sleep session is another—the total amount of time spent in each sleep stage may be divided by the total amount of time spent in all of the sleep stages (including the "awake" sleep stage) to produce such a percentile breakdown. In another example, by measuring the time from the onset of a sleep session record to the first epoch or time period classified as having a light sleep stage, a "time to sleep" or "sleep onset latency" meta-statistic may be determined. These meta-statistics may then be presented to the user via a GUI (some examples of such meta-statistic presentation are included in the example GUIs herein).

Figure 13:
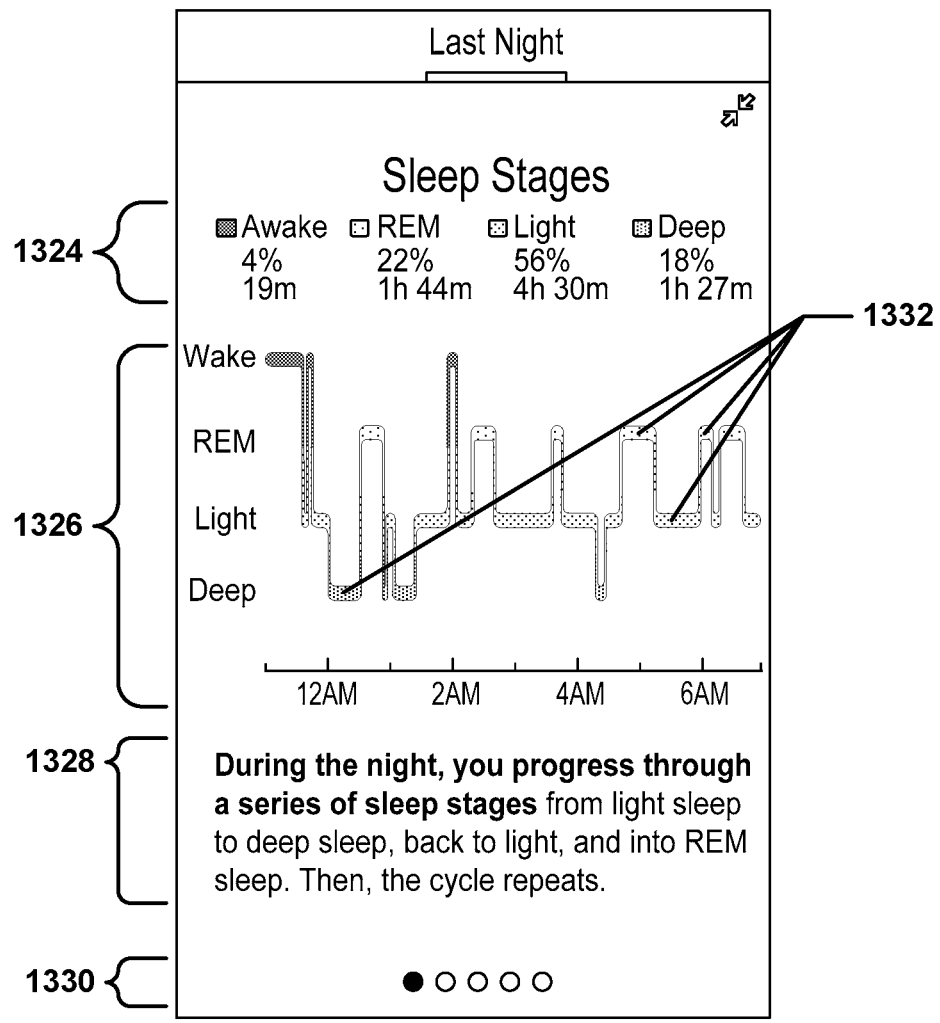
FIG. 13 depicts an example of a graphical user interface that may be used to present sleep stage data for a sleep session.

FIG. 13 depicts an example of a graphical user interface that may be used to present sleep stage data for a sleep session. In FIG. 13, a percentile breakdown 1324 of time spent in each of the various sleep stages tracked during a sleep session is presented. In this example, the classifier that was used classified each interval or epoch into one of four sleep stages: awake, REM, light, and deep. It is to be understood that "sleep stages," as the term is used herein, may be used to refer to the "awake" sleep stage or the like as well as to sleep stages in which the person is actually asleep. The percentile breakdown 1324 may provide a high-level overview or snapshot of the person's overall sleep behavior during the sleep session being reviewed.

Figure 14:
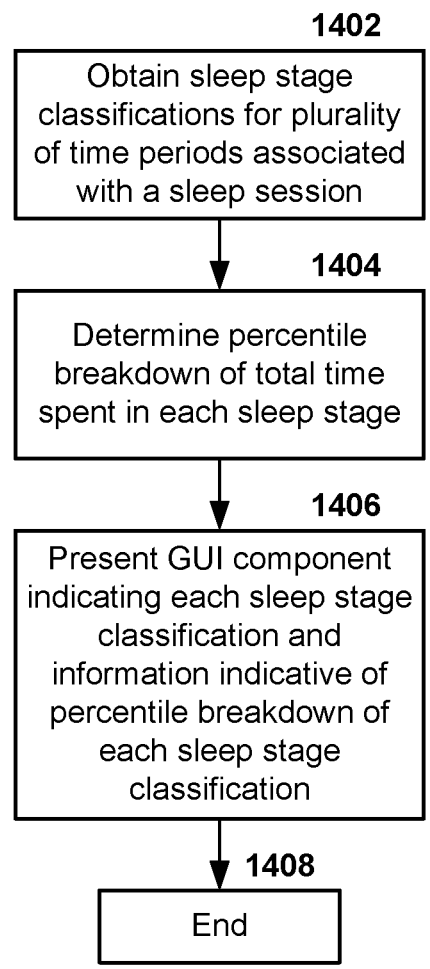
FIG. 14 depicts a flow diagram of a technique associated with presenting summary data.

FIG. 14 depicts a flow diagram of a technique associated with such summary data. In block 1402, sleep stage classifications for a plurality of time periods associated with a sleep session may be obtained. In block 1404, the total amount of time spent in each sleep stage during the sleep session may be determined and then divided by the total amount of time spent in all of the different sleep stages to determine a percentile breakdown of the total time spent in each sleep stage during the sleep session. In block 1406, a GUI component indicating each sleep stage classification and information indicative of the percentile breakdown of the amount of time during the sleep session spent in each sleep stage may be presented. Such a GUI component may, for example, include a textual breakdown, e.g., "4% Awake," "22% REM," "56% Light," and "18% Deep," and/or a graphical representation, e.g., a vertically or horizontally oriented histogram or a pie chart. The technique may end in block 1408.

A more detailed presentation of the sleep data may be provided by way of a hypnogram 1326, which is a type of timeline in which time intervals during the timeline corresponding with particular sleep stages are indicated with horizontal lines or segments 1332 spanning those time intervals (with respect to the horizontal axis) at different elevations, each elevation corresponding to a different one of the sleep stages into which the time intervals have been classified. In the hypnogram 1326, the time intervals assigned an "awake" sleep stage are plotted at the highest elevation, the time intervals assigned the "REM" sleep stage are plotted at the next highest elevation, the time intervals assigned the "light" sleep stage are plotted at the next highest elevation, and the time intervals assigned the "deep" sleep stage are plotted at the lowest elevation. While hypnograms are known in the art, various variations on the hypnogram discussed herein represent improvements to how hypnograms may be utilized in order to provide more effective and meaningful feedback to a person seeking to monitor their sleep.

The GUI of FIG. 13 also includes textual content 1328, which may be content that is selected based on the type of information being presented or based on one or more aspects of the sleep session data that is being presented. In FIG. 13, the textual content simply explains the progressions through the various sleep stages during a typical sleep session, which may be informative to a person unfamiliar with the subject of sleep monitoring. A user interface feature or input 1332 may allow a person to scroll or page through multiple different versions of the GUI of FIG. 13, as is discussed in more detail below.

Figure 15:
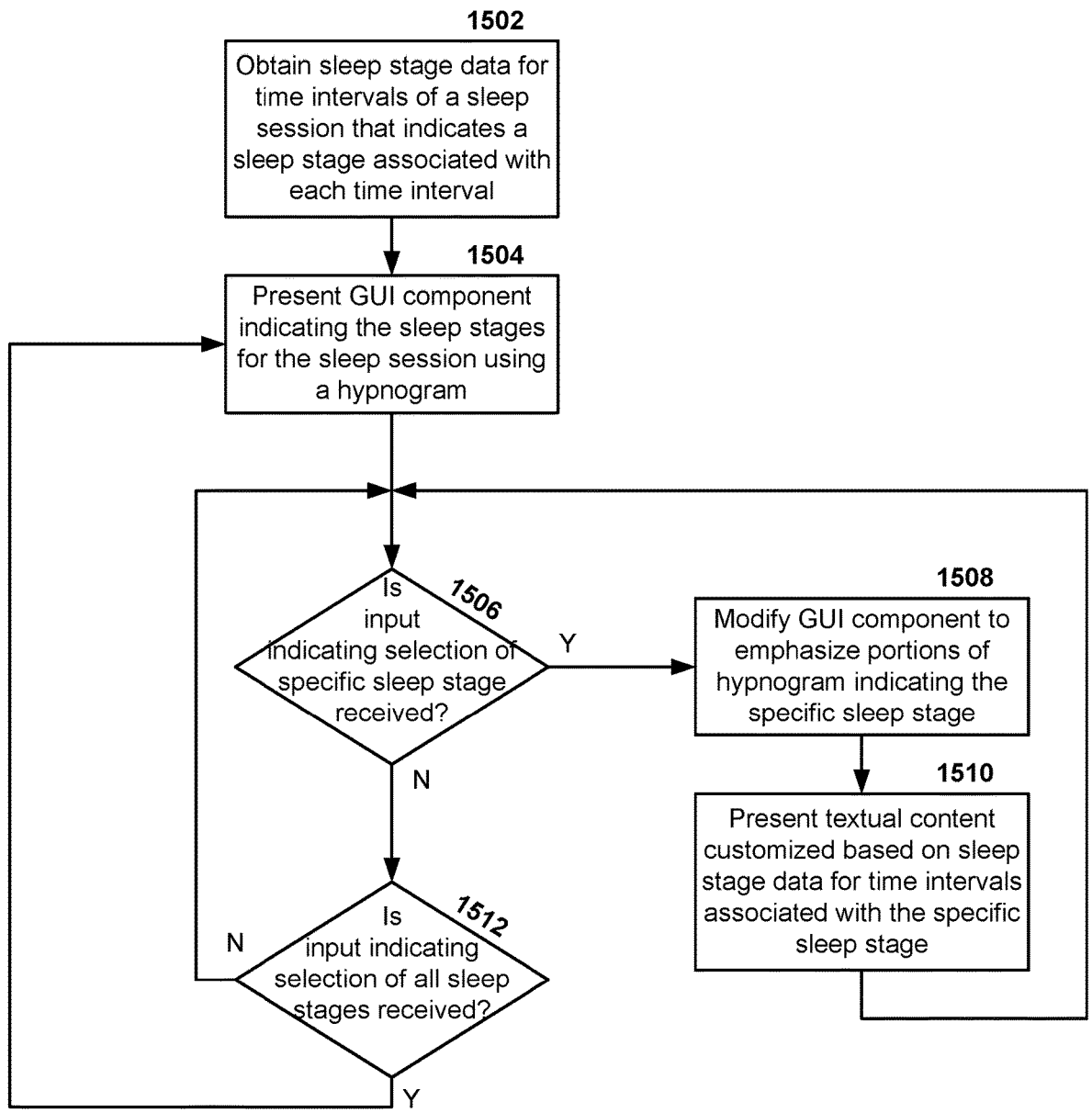
FIG. 15 depicts a flow diagram of another technique for presenting sleep stage data.

FIG. 15 depicts a flow diagram of another technique for presenting sleep stage data. In block 1502, sleep stage data for time intervals of a sleep session may be obtained. Each time interval may be associated with a particular sleep stage according to a classifier, as discussed earlier herein. In block 1504, a GUI component including a hypnogram may be presented that indicates the obtained time intervals and their associated sleep stages. This GUI component may, for example, be similar to the hypnogram 1326 in FIG. 13.

In block 1506, a determination may be made as to whether an input has been received, e.g., via the user input region 1330 of the GUI of FIG. 13, indicating a selection of a specific one of the sleep stages represented in the hypnogram. If it is determined in block 1506 that a specific one of the sleep stages has been selected by a user, then the technique may proceed to block 1508, in which the GUI component, i.e., the hypnogram, may be modified to emphasize or accentuate the portions of the hypnogram corresponding with the selected sleep stage. For example, the horizontally-extending elements of the hypnogram that represent the time intervals associated with the selected sleep stage may be bolded, caused to pulse in brightness or color, and/or presented with a more vivid color than in the initial hypnogram. Alternatively or additionally, the horizontally-extending elements of the hypnogram that represent the time intervals associated with the other sleep stages may be de-emphasized, e.g., by muting their colors, displaying them with a reduced color intensity, fading them out, or even hiding them altogether. Thus, the accentuated time intervals of the hypnogram may be caused to have a different graphical appearance than the other time intervals of the hypnogram.

In block 1510, the textual content that is displayed for the modified GUI may be updated or changed to include information that has been customized based on the selected sleep stage and/or the actual data associated with the selected sleep stage for the sleep session being reviewed. Examples of the modifications that may be performed in blocks 1508 and 1510 are discussed in more depth below with respect to FIGS. 16 through 19. After the GUI has been modified, the technique may return to block 1506 for further monitoring of whether an input indicating a selection of a different specific sleep stage is received.

If it is determined in block 1506 that no selection of a specific sleep stage of the sleep stages has been made, then the technique may proceed to block 1512, in which another determination may be made as to whether an input indicating selection of all sleep stages has been received. If it is determined in block 1514 that an input indicating a selection of all sleep stages has been received, then the technique may return to block 1504. If it is determined in block 1514 that no input indicating a selection of all sleep stages has been received, then the GUI may be left in whatever state it currently is and the technique may return to block 1506. Such a technique may allow for presentation of summary sleep stage data using the GUI but may also allow the user to switch between summary output that does not focus on any particular sleep stage data and more specific summary output that focuses in on a particular one of the sleep stages. Examples of GUIs that focus on specific sleep stages follow.

For example, five circles can be seen at the bottom of FIG. 13—each circle may correspond to a different version of the GUI that is depicted. The first version, which is depicted in Figure NN, may present summary information for the entire sleep session in question. However, the remaining four versions of the GUI may each focus on data associated with a different sleep stage.

Figure 16:
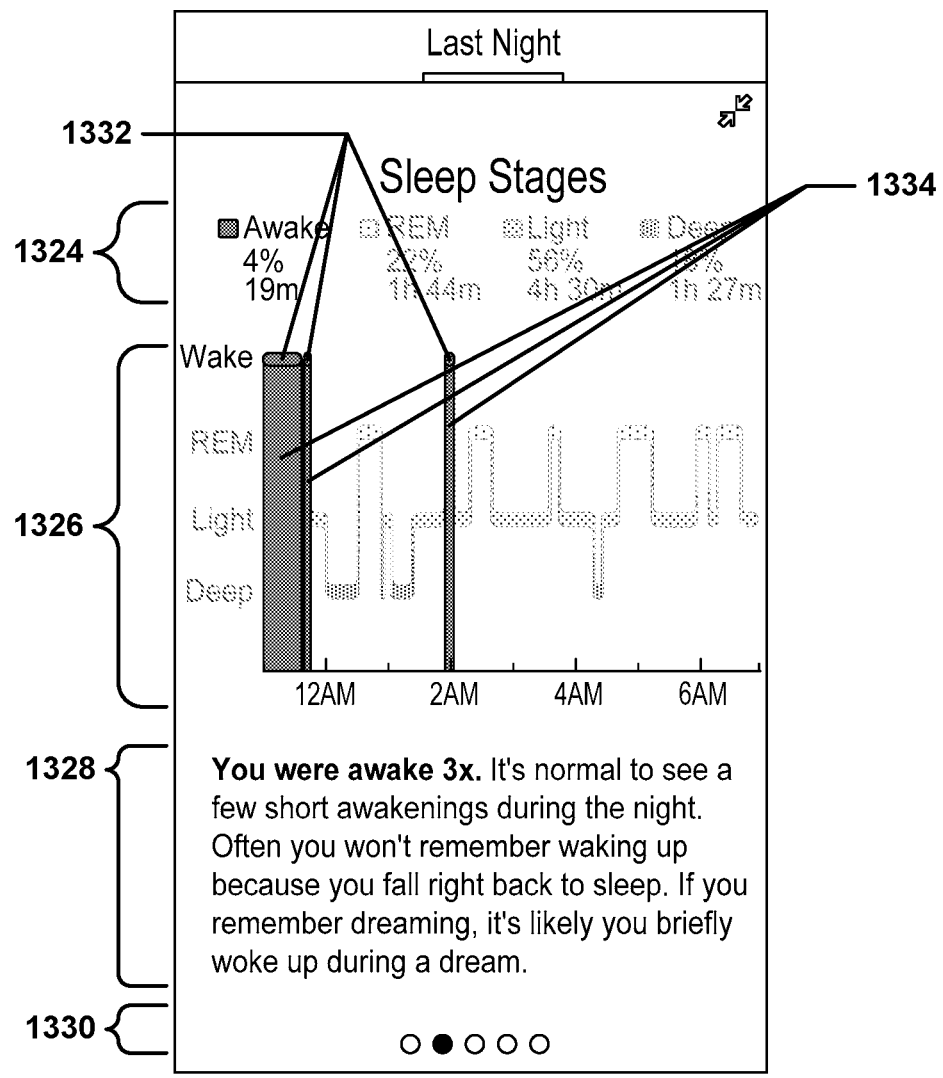
FIGS. 16 through 19 depict the GUI of FIG. 13, but modified such that the percentile breakdown associated with a different sleep stage is emphasized in each Figure by greying or fading out the remaining percentile breakdowns.

For example, FIG. 16 depicts the GUI of FIG. 13, but modified such that the percentile breakdown 1324 associated with the "awake" sleep stage, e.g., the top-most sleep stage in this example hypnogram, is emphasized by greying or fading out the remaining percentile breakdowns 1324 associated with the other sleep stages. Furthermore, the hypnogram 1326 may be emphasized in the same way and/or augmented with additional indicators to emphasize the "awake" sleep stage intervals. For example, in FIG. 00, the portions of the hypnogram 1326 that are associated with sleep stages other than the "awake" stage are greyed or faded out, similar to the percentile breakdowns 1324 for those sleep stages. In contrast, the portions of the hypnogram 1326 associated with the "awake" sleep stage may be presented in their normal color palette or even emphasized with new colors or formatting. In particular, in some embodiments, vertical bars 1334 spanning the width of the horizontal segments 1332 indicating the time periods associated with the awake sleep stage may be added to the hypnogram 1326 in order to allow the person reviewing the data to more easily discern where the time intervals stop and start on the timeline at the bottom of the hypnogram 1326. These vertical bars 1334 may span between the horizontal segments 1332 and the horizontal axis of the hypnogram 1326. Thus, the regions marked by vertical bars may provide a different graphical appearance as compared with the regions under or over the horizontal segments for the other the time intervals of the hypnogram, thereby further accentuating the time intervals associated with the selected sleep stage.

In addition to the changes to the percentile breakdowns 1324 and the hypnogram 1326, the textual content 1328 may also be changed based on the sleep stage data that has been collected for a sleep session. For example, in FIG. 16, the textual content has been customized by summarizing the number of time intervals in which the person was awake, e.g., three time intervals in this case. Alternatively, the total duration spent in the awake sleep stage may be presented in the textual content, or some other quantity associated with or driven by the sleep stage data for the awake sleep stage. In addition to the quantity-based information that may be presented in the textual content 1328, the textual content 1328 may also include other types of customized information. For example, explanatory text may be provided, depending on the frequency and/or duration of times that the person spent in the awake stage, that provides the person with some insight as to whether their sleep stage data for the awake stage is "normal." In this particular example, the person using the device is reassured that the number of time intervals in which the person was "awake" during the sleep session is a normal amount of such intervals.

Figure 17:
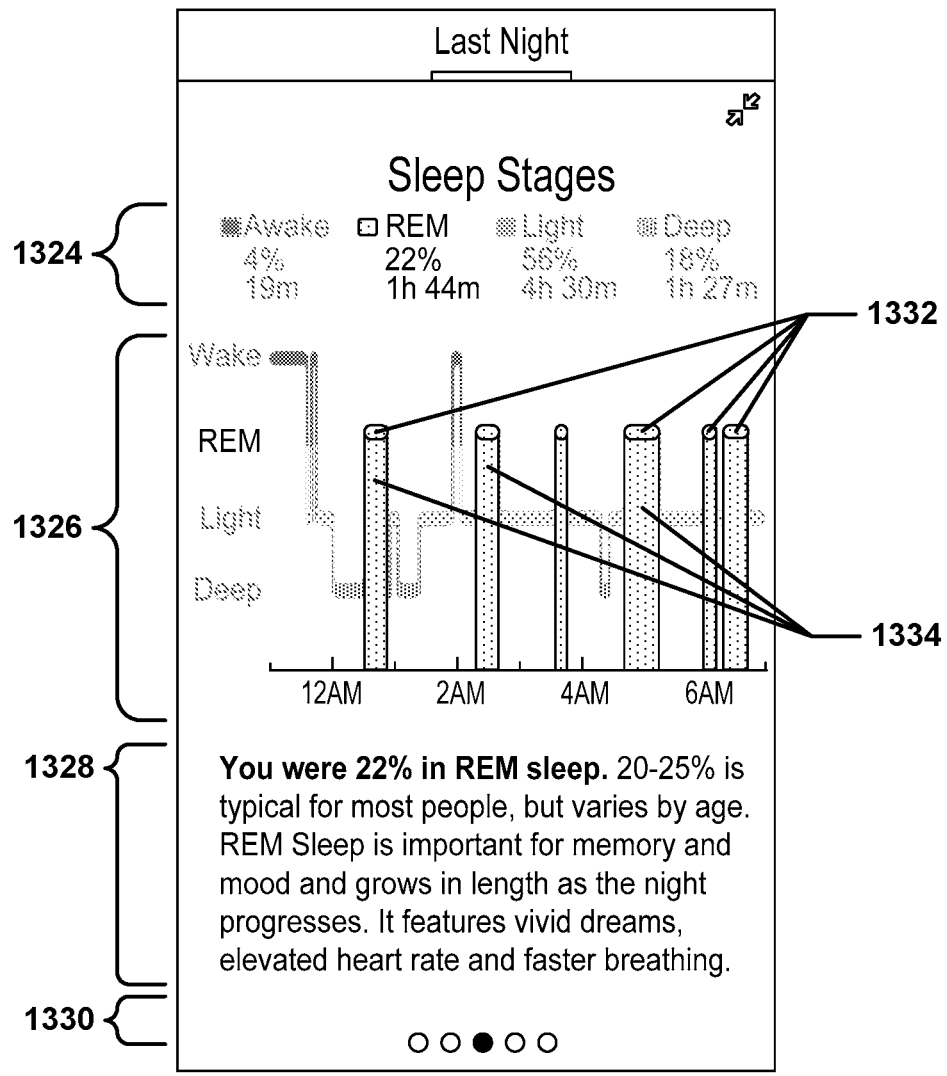

FIG. 17 depicts the user interface of FIG. 13 but modified to emphasize the intervals or epochs that have been classified as being associated with the REM sleep stage. For example, vertical bars 1334 have been added to connect the horizontal segments 1332 associated with the REM sleep stage to the horizontal axis. Moreover, the horizontal bars for the remaining sleep stages have been greyed out or faded out. The textual content 1330 has also been changed to display information that is pertinent to the REM sleep stage and the person's REM sleep stage data. In this example, the textual content recaps the percentage of the sleep session that the person spent in the REM sleep stage. To give context to this number, the textual content 1330 may include information regarding typical percentages of time that an average person spends in the REM sleep stage. Such typical percentages may be selected, for example, so as to be particularly relevant to the user. For example, if the user's age and/or gender are known, then the typical percentage of time that is spent in the REM sleep stage that is presented to the user may be drawn from a more relevant population of individuals, e.g., the user may be presented with a range of average REM sleep stages percentages based on the typical sleep behavior people of a similar demographic. In addition to such comparative information, the textual content 1330 may also include physiological information that is related to the REM sleep stage. For example, the textual content 1330 may include information that informs the user what the physiological characteristics of REM sleep are, such as elevated heart rate, vivid dreams, faster breathing, increased movement, etc.

Figure 18:
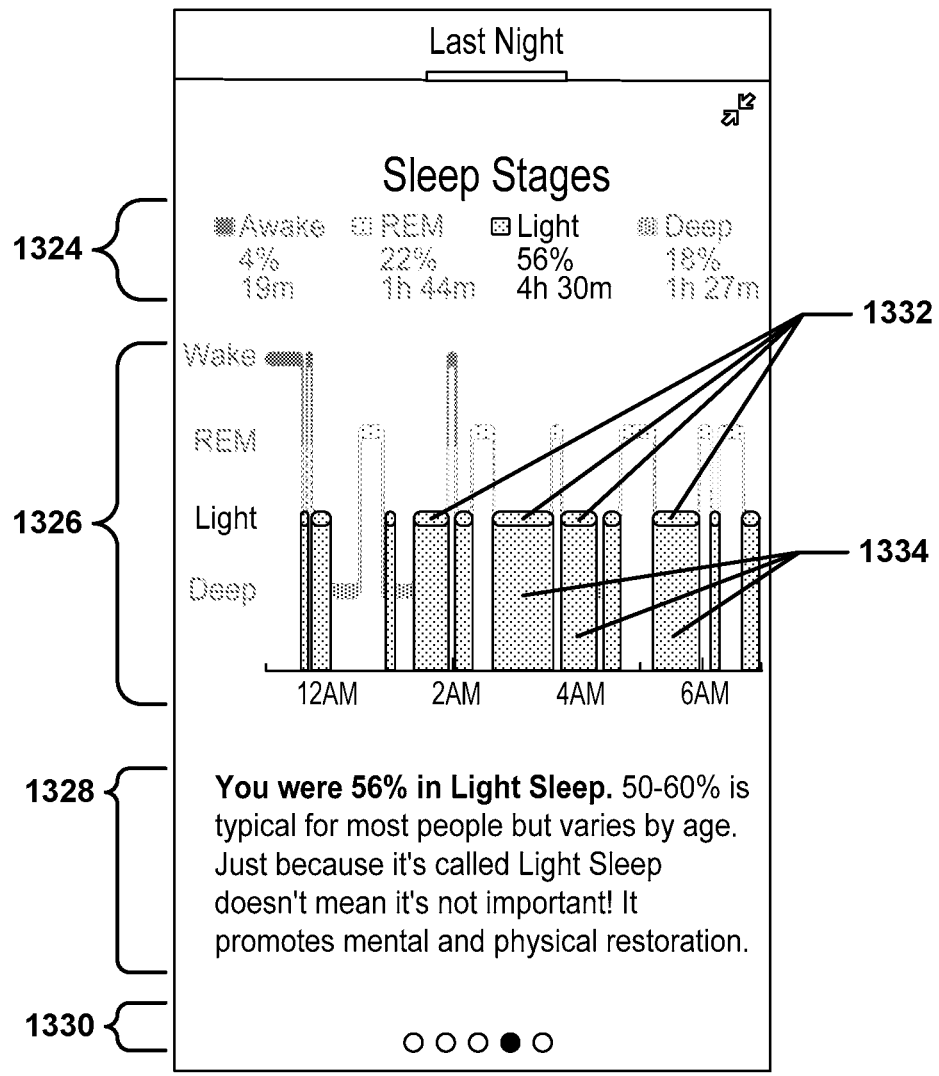

FIG. 18 depicts the user interface of FIG. 13 but modified to emphasize the intervals or epochs that have been classified as being associated with the light sleep stage. As with the modified interface shown in FIG. 17, the textual content 1330 has been modified to show the percentage of the sleep session that was spent in the sleep stage of interest, in this case, the light sleep stage.

Figure 19:
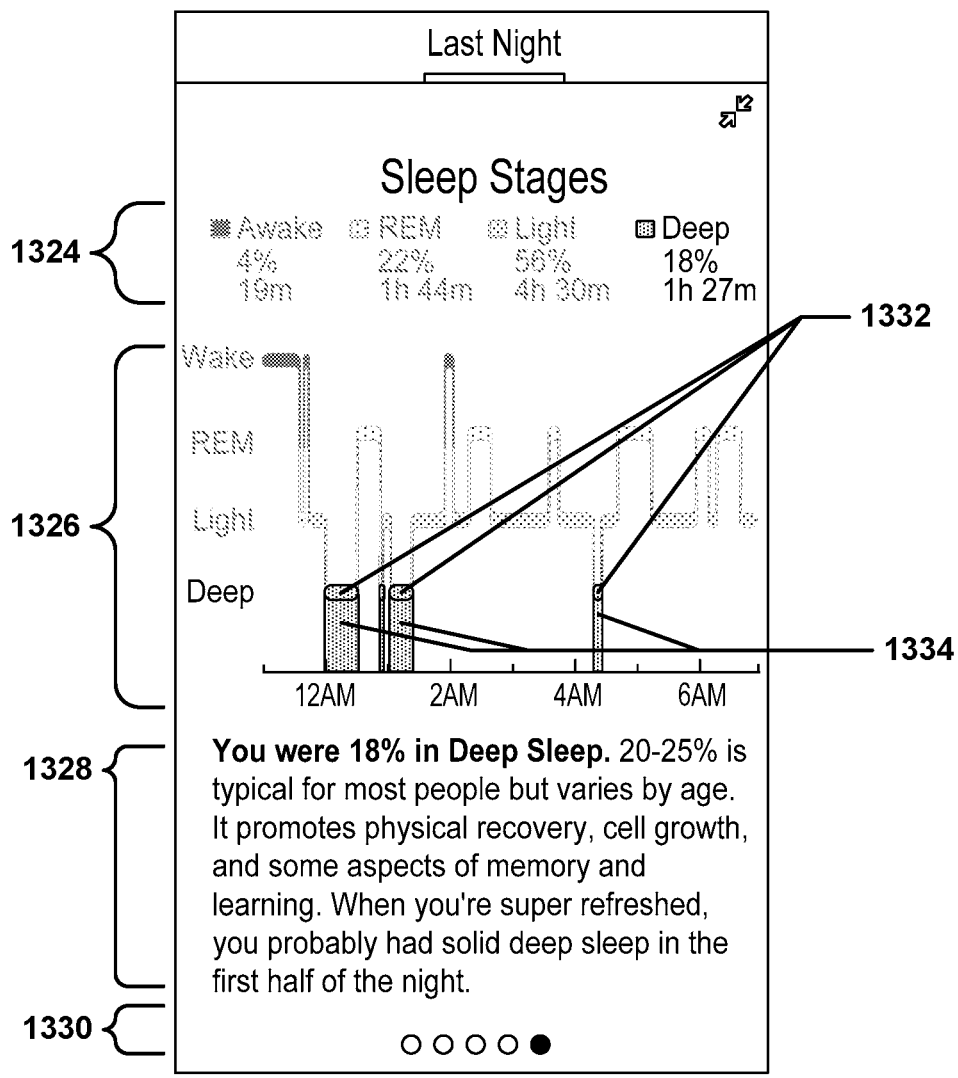

FIG. 19 depicts the user interface of FIG. 13 but further modified to emphasize intervals or epochs that have been classified as being associated with the deep sleep stage. As with the previous modified user interfaces, this user interface has textual content that has been customized based on the user's actual sleep data, e.g., an indication of the percentage of the sleep session spent in the deep sleep stage, as well as information regarding the physiological effects of deep sleep and how much deep sleep is typical for most people.

The user may use the user input 1330 to navigate between the summary screen (see FIG. 13) and any of the sleep-stage-specific modified user interfaces (see FIGS. 16 through 19) by swiping to the left or right. Of course, other input systems may be used as well to navigate between the different user interfaces or modifications thereof.

Figure 20:
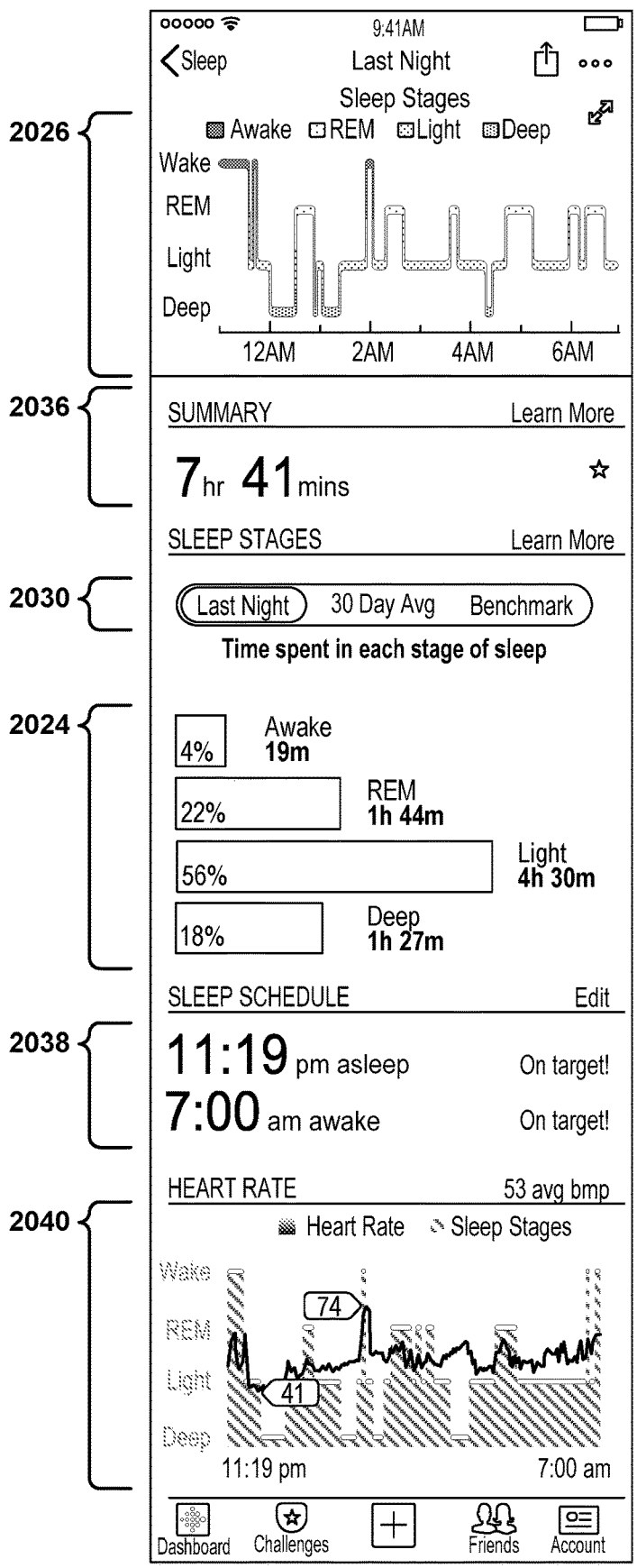
FIG. 20 depicts a more comprehensive user interface that may be used to provide information regarding various aspects of a person's sleep session.

FIG. 20 depicts a more comprehensive user interface that may be used to provide information regarding various aspects of a person's sleep session. The user interface in FIG. 20 is designed for use with a mobile phone or other device having a portrait-mode display. The user interface may not be completely visible within the display and may be configured to be slid up or down, as desired, to make different portions of the user interface visible. Of course, other layouts are also possible, including layouts that may not require partial display of the user interface.

In the user interface depicted in FIG. 20, a hypnogram 2026 may be displayed that is similar to the hypnograms 1326 discussed earlier. A summary 2036 of the total time slept in the sleep session may be provided as well; this summary 2036 may, as is the case here, exclude time spent in the awake sleep stage. A user input area 2030 may be provided to allow the user to navigate between different user interfaces or to modify the current user interface to display different comparative data, as will be explained with respect to later figures. In this case, the user input area 2030 includes three user-selectable options: last night, 30-day average, and benchmark. These are explained in more detail later.

The user interface of FIG. 20 may also include a percentile breakdown 2024 that is similar to that discussed earlier with respect to FIGS. 13 through 19. Further sleep session data, such as the start and end of sleep in the sleep session may be displayed in a sleep session schedule section 2038. It is to be understood that some reported characteristics of a sleep session, such as duration of the sleep session, start of sleep, end of sleep, etc., may be evaluated based on when a person actually falls asleep and when the person later permanently (at least for the day) wakes up, whereas other aspects of a sleep session may include activity that occurs prior to falling asleep. For example, a sleep session may be started when it is detected that the person is attempting to fall asleep, e.g., by adopting a horizontal position (which may be sensed by, for example, the motion sensor in the wearable device or may be inferred from the time of day or even explicitly communicated by the user, e.g., by pushing a particular button on the wearable device or providing input to a secondary device that is in communication with the wearable device. The period of time between the "start" of the sleep session and when the person actually falls asleep may include intervals during which the person is in the "awake" sleep stage.

The user interface may also, optionally, include a graphical element that depicts heart rate over time, e.g., such as heart rate display 2040. In this example, the heart rate display 2040 is overlaid on a reproduction of the hypnogram 2026 to allow the user to observe correlations between heart rate and sleep stages (the hypnograms shown for 2026 and 2040 are different in this example, but it is to be understood that this is for illustrative purposes only; in actual practice, the hypnograms may be based on the same dataset and would be identical in such cases). The heart rate display 2040 may optionally highlight the peak heart rate 2044 and the lowest heart rate 2046 experienced during a sleep session, e.g., by including an indicator pointing to the location of each such maximum or minimum, possibly with textual information indicating the actual value of those maxima/minima.

Figure 21:
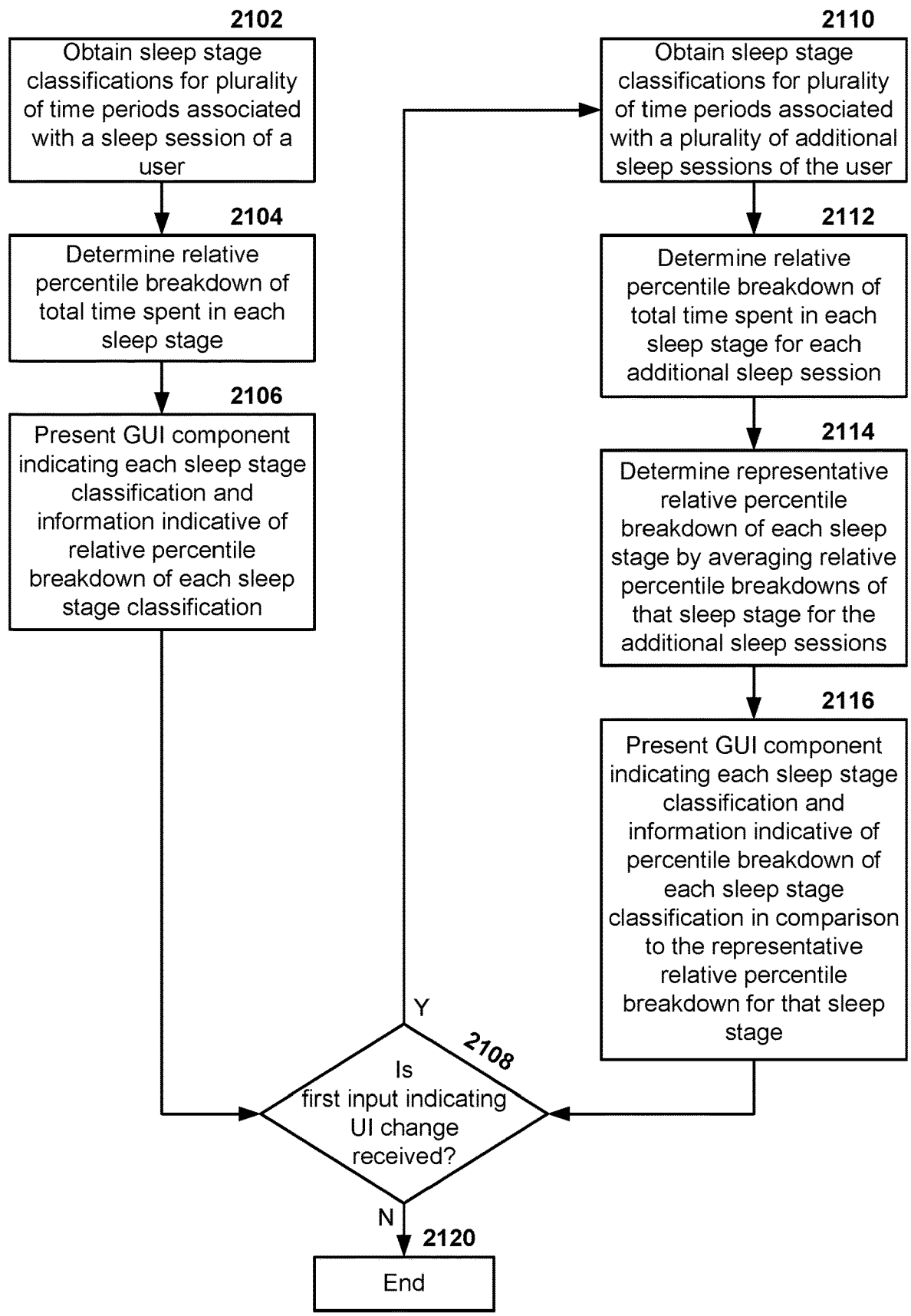
FIG. 21 depicts a flow diagram of a technique for displaying a GUI that allows for comparison of sleep stage data against historical sleep stage data.

A GUI such as that depicted in FIG. 20 may be modified according to a technique that is discussed below with respect to FIG. 21 in order to compare sleep session sleep stage data against historical sleep stage data for a user. In FIG. 21, blocks 2102, 2104, and 2106 may correspond with operations similar to those in blocks 1402, 1404, and 1406, discussed above with respect to FIG. 14. For example, block 2106 may cause the display of a GUI component such as the percentile breakdown 2024 to be displayed. In block 2108, a determination may be made as to whether a user input has been received indicating a desire on the part of a user to modify the GUI to display a comparison of the sleep session sleep stage data against historical sleep stage data for that user. If it is determined in block 2108 that no user input has been received indicating a desire to modify the GUI, then the technique may end in block 2118. Alternatively, the block 2108 may repeat periodically during the presentation of the GUI component from block 2106 in order to monitor for such potential user inputs over time.

If it is determined in block 2108 that a user input has been received indicating a desire to modify the GUI, then the technique may proceed to block 2110, in which sleep stage classifications for a plurality of additional sleep sessions of the user may be obtained; this information may be referred to as "representative personal sleep stage data." This may be similar to the operations performed in block 2102, except for multiple, previous sleep sessions instead of the sleep session that is the focus of block 2102. The number of multiple previous sleep sessions may, for example, span a period of 1 week prior to the time when the GUI is presented, 4 weeks prior to when the GUI is presented, 15 days prior to when the GUI is presented, or 30 days prior to when the GUI is presented. Alternatively, such time intervals may be evaluated with respect to the time when the sleep session in question was recorded (instead of when the GUI presenting that sleep session's data is presented).

In block 2112, the relative percentile breakdown of total time spent in each sleep stage for each additional sleep session may be determined, e.g., by dividing the total amount of time spent in each of the sleep stages for each sleep session by the total duration of that sleep session. In block 2114, the average of the relative percentile breakdowns for each sleep stage over all of the additional sleep sessions that were obtained in block 2110 may be determined to produce representative relative percentile breakdowns for the sleep stages. Alternatively, the total amount of time spent in each sleep stage over all of the additional sleep sessions that are obtained in block 2110 may be divided by the total duration of all of those additional sleep sessions in order to arrive at the representative relative percentile breakdowns. In block 2116, the GUI component, e.g., the percentile breakdown 2024, may be modified to indicate each sleep stage classification and information that is indicative of the percentile breakdown of each sleep stage for the sleep session from block 2102 as well as information that is indicative of the representative relative percentile breakdowns for the sleep stages. This information may be presented such that the sleep stage percentile breakdowns for the sleep session in question may be easily compared against the corresponding representative relative percentile breakdowns.

Figure 22:
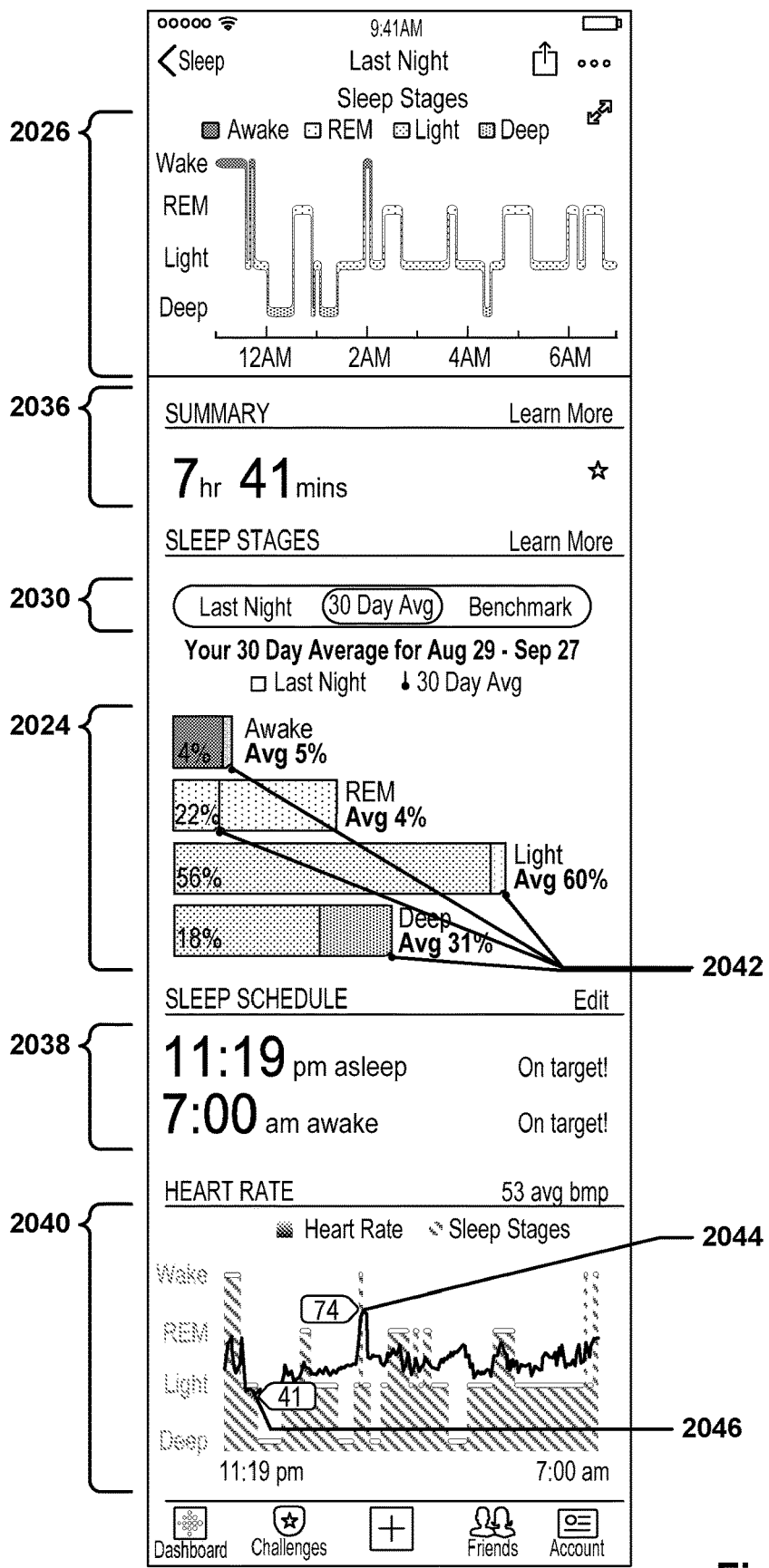
FIG. 22 depicts the user interface of FIG. 20, except that it has been modified to include comparative data in the percentile breakdown.

For example, FIG. 22 depicts the user interface of FIG. 20, except that it has been modified to include comparative data in the percentile breakdown 2024 responsive to the user selection of "30 day average" in user input area 2030. In response to this selection, representative relative percentile breakdowns 2042 have been added to the percentile breakdown display 2024. These representative relative percentile breakdowns 2042, in this case, are average percentage breakdowns for the person for sleep sessions over the previous 30 days. This allows the user to easily see if the previous night's sleep was an anomaly compared to recent sleep sessions. For example, if a person wakes up feeling very tired as compared with recent sleep sessions, such a comparison may allow them to rapidly see that they spent a larger (or much smaller) amount of time in a particular sleep stage in the most recent sleep session as compared with a larger population of recent sleep sessions.

Figure 23:
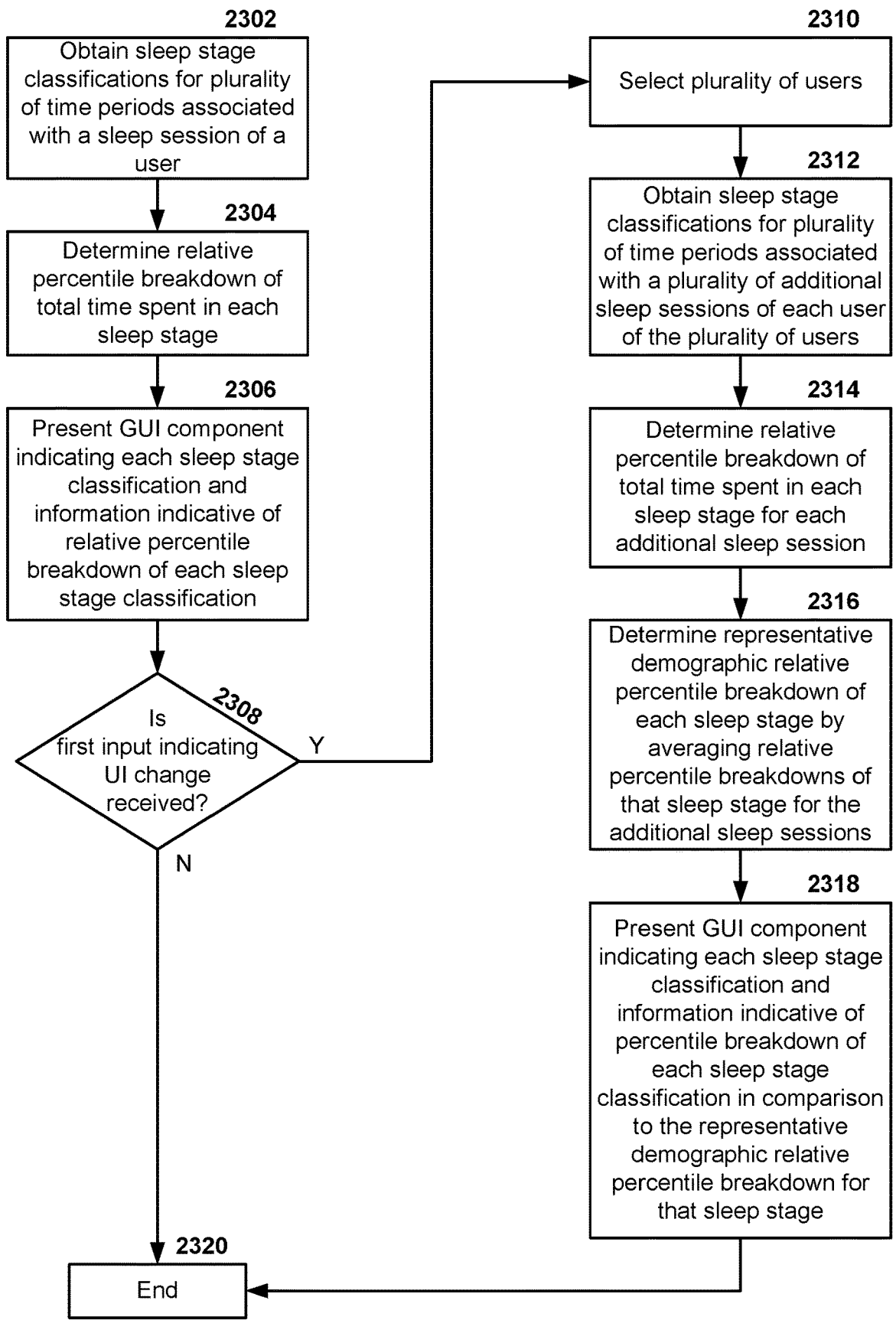
FIG. 23 depicts a flow diagram of a technique for displaying a GUI that allows for comparison of sleep stage data against demographic sleep stage data.

A GUI such as that depicted in FIG. 20 may also be modified according to a technique that is discussed below with respect to FIG. 23 in order to compare sleep session sleep stage data against sleep stage data for a plurality of users; the sleep stage data of the plurality of users may be selected based on the demographics of the users with which it is associated, as is discussed in more detail below. In FIG. 23, blocks 2302, 2304, and 2306 may correspond with operations similar to those in blocks 1402, 1404, and 1406, discussed above with respect to FIG. 14. For example, block 2306 may cause the display of a GUI component such as the percentile breakdown 2024 to be displayed. In block 2308, a determination may be made as to whether a user input has been received indicating a desire on the part of a user to modify the GUI to display a comparison of the sleep session sleep stage data against sleep stage data for a plurality of users. If it is determined in block 2308 that no user input has been received indicating a desire to modify the GUI, then the technique may end in block 2320. Alternatively, the block 2308 may repeat periodically during the presentation of the GUI component from block 2306 in order to monitor for such potential user inputs over time.

If it is determined in block 2308 that a user input has been received indicating a desire to modify the GUI, then the technique may proceed to block 2310, in which a plurality of users may be selected. Such users may be selected so as to match one or more demographic criteria matching (or being within a predefined range of) various demographic parameters of the user who is reviewing their sleep stage data. For example, if the user in question is a 42 year old male, then a plurality of users may be selected that are male and between the ages of 40 and 45. It is to be understood that in some embodiments, the plurality of users may be selected regardless of demographic details. It is also to be understood that the plurality of users may be selected based on any number of potential demographic parameters, including, for example, approximate locational latitude, time zone, age, gender, work schedule, fitness level, average daily activity level, and so forth. Once a suitable plurality of users is selected, the technique may proceed to block 2312, in which sleep stage classifications for a plurality of time periods associated with a plurality of additional sleep sessions for the plurality of users may be obtained. This may be similar to the operations performed in block 2302, except for multiple, previous sleep sessions for multiple users instead of the sleep session that is the focus of block 2302.

In block 23142, the relative percentile breakdown of total time spent in each sleep stage for each additional sleep session may be determined, e.g., by dividing the total amount of time spent in each of the sleep stages for each sleep session by the total duration of that sleep session. In block 2316, the average of the relative percentile breakdowns for each sleep stage over all of the additional sleep sessions that were obtained in block 2312 may be determined to produce representative demographic relative percentile breakdowns for the sleep stages. Alternatively, the total amount of time spent in each sleep stage over all of the additional sleep sessions that are obtained in block 2312 may be divided by the total duration of all of those additional sleep sessions in order to arrive at the demographic relative percentile breakdowns. In block 2318, the GUI component, e.g., the percentile breakdown 2024, may be modified to indicate each sleep stage classification and information that is indicative of the percentile breakdown of each sleep stage for the sleep session from block 2302 as well as information that is indicative of the demographic relative percentile breakdowns for the sleep stages. This information may be presented such that the sleep stage percentile breakdowns for the sleep session in question may be easily compared against the corresponding demographic relative percentile breakdowns.

Figure 24:
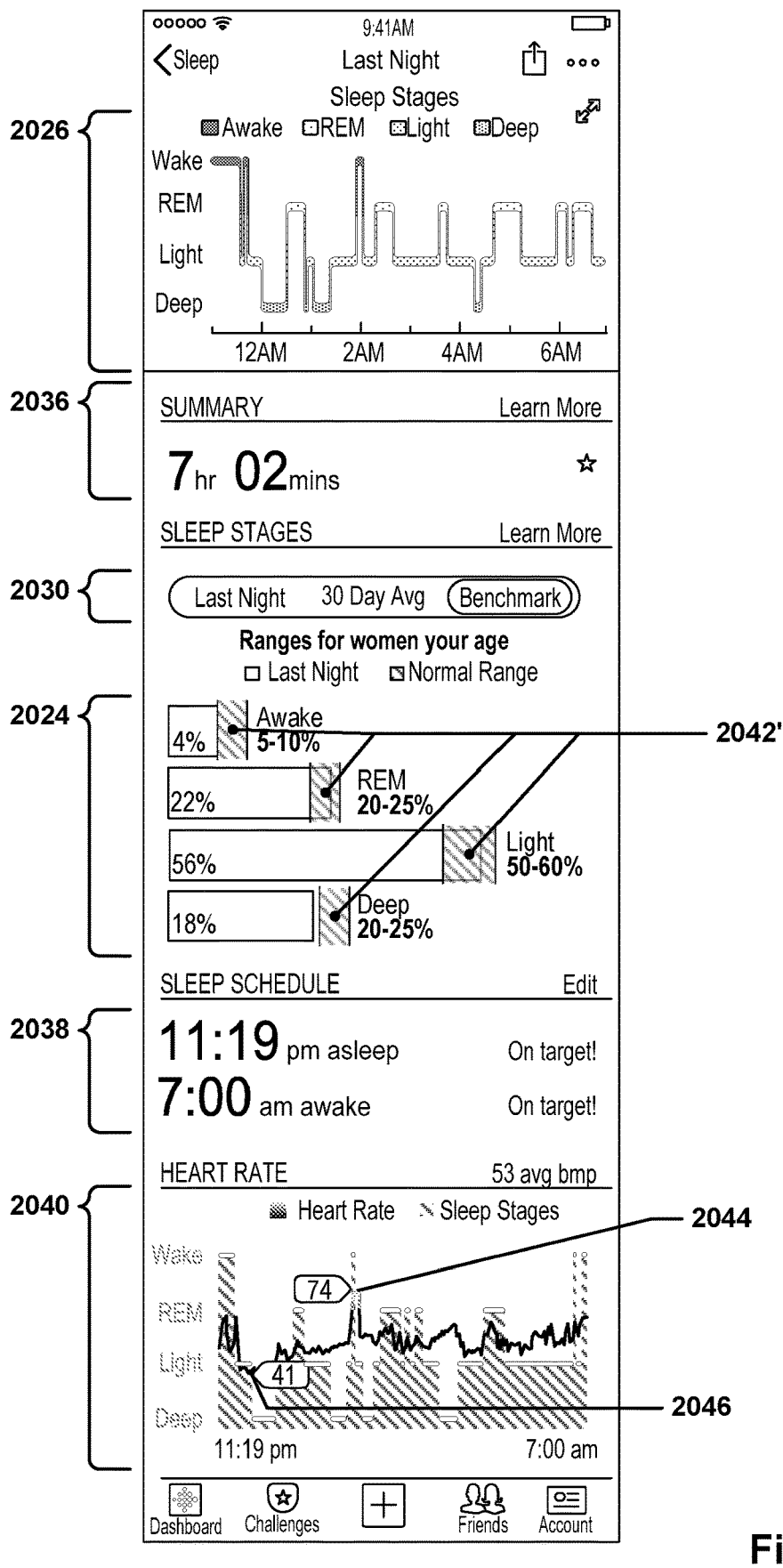
FIG. 24 depicts the user interface of FIG. 20, except that it has been further modified to include comparative data in the percentile breakdown.

For example, FIG. 24 depicts the user interface of FIG. 20, except that it has been further modified to include comparative data in the percentile breakdown 2024 that indicates representative demographic relative percentile breakdown ranges 2042', which may be drawn from a larger population of users. Such representative demographic relative percentile breakdowns may be determined based on data from other users and may be filtered or downselected in order to be more closely attuned to the user's demographic. For example, if the user is female and in her 20's, then the representative demographic relative percentile breakdowns may be determined based on data from other female users in the age range of 20 to 29. Conversely, if the user is male and in his 60's, then the representative demographic relative percentile breakdowns presented may be for males over 60.

It is to be understood that the representative relative percentile breakdowns or the representative demographic relative percentile breakdowns may be expressed as single values, as is shown in FIG. 22, or as ranges, as is shown in FIG. 24.

Figure 25:
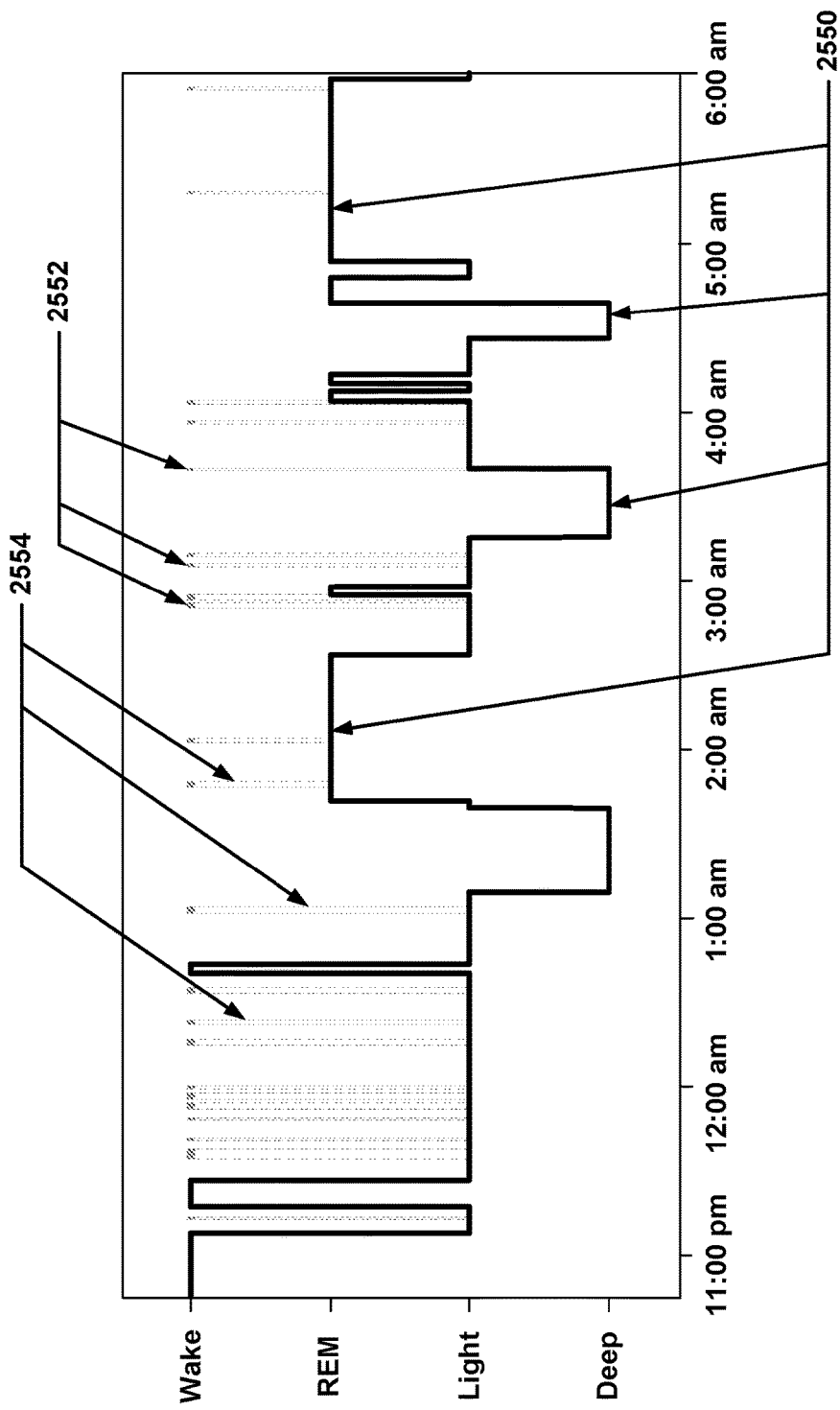
FIG. 25 depicts a hypnogram that displays, for some time intervals, dual sleep stage indications.

The hypnogram displays that are included in parts of the GUIs discussed above may, in some embodiments, be modified to provide for enhanced readability and understanding on the part of the viewer. FIG. 25 depicts a hypnogram that displays, for some time intervals, dual sleep stage indications. In particular, time intervals that are classified as being associated with an "awake" sleep stage may, if of a sufficiently short duration, also be displayed as being associated with a non-awake sleep stage of one or both adjoining time intervals in addition to being displayed as a time interval associated with the "awake" sleep stage. In such embodiments, the display of the time interval as being in the "awake" sleep stage may be muted or otherwise de-emphasized with respect to the display of the same time interval as being in the non-awake sleep stage. This may prove useful to the user since it may help de-clutter the hypnogram, which may, even when presenting perfectly normal sleep data, include a large number of very short-duration intervals associated with the "awake" sleep stage. In some sense, this is another way of implementing a post-classification rule, as discussed earlier herein, except that the original sleep stage classification of the time intervals in question are retained even after the time intervals are re-classified. In FIG. 25, the solid, heavy black line represents a hypnogram of a sleep session of a user. Various first graphical elements 2550, e.g., horizontal line segments or other graphical elements extending along the horizontal axis, may be used to indicate display time intervals (which are discussed in more detail below with respect to FIG. 26) corresponding to various sleep stages. Light-grey second graphical elements 2552 indicate time intervals that are associated with an awake sleep stage but that are less than a first threshold in duration, e.g., less than or equal to 3 minutes—these time intervals are still shown as being associated with the "awake" sleep stage (by virtue of being located at the elevation corresponding to the "awake" sleep stage), but in a de-emphasized manner as compared with the display time intervals. In some embodiments, the second graphical elements 2552 may be joined to the first graphical elements 2550 by vertical extension lines 2554, which may be dashed or dotted (or otherwise of a different format) to prevent them from being confused with the solid vertical lines that join each pair of adjacent first graphical elements 2550 that are used in the primary hypnogram display.

Figure 26:
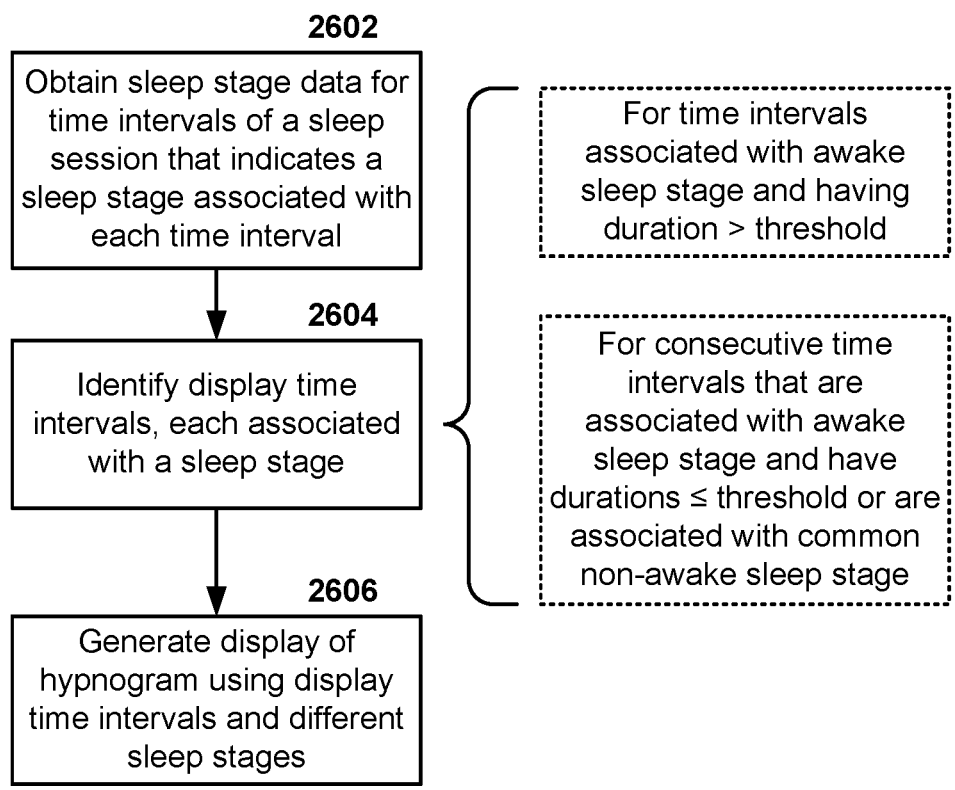
FIG. 26 depicts a flow diagram of one technique for providing an enhanced hypnogram display such as is depicted in FIG. 25.

FIG. 26 depicts a flow diagram of one technique for providing such an enhanced hypnogram display. In block 2602, sleep stage data for time intervals of a sleep session may be obtained. The sleep stage data may indicate a sleep stage associated with each such time interval. In block 2604, display time intervals may be identified, each of which may be associated with one of the sleep stages and may span one or more of the time intervals of the sleep stage data. The display time intervals associated with the "awake" sleep stage may each be coextensive with a corresponding time interval associated with the "awake" sleep stage and have a duration longer than a designated first threshold amount. The display time intervals associated with the non-awake sleep stages may each be coextensive with one or more consecutive time intervals that are each a) associated with the sleep stage with which that display time interval is associated or b) associated with the "awake" sleep stage and less than or equal to the first threshold amount. It is to be understood that time intervals classified as being associated with an "artefact" or "off-wrist" sleep stage may, in various implementations, be treated in such an enhanced hypnogram as intervals associated with the "awake" sleep stage (such as the "awake" sleep stages represented by items 2552 in FIG. 25) or, in other implementations, as intervals associated with one of the non-awake sleep stages. In the latter case, these artefact or off-wrist sleep stage intervals may be re-classified, at least for the purposes of displaying the enhanced hypnogram, as having one of the non-awake sleep stages, e.g., the non-awake sleep stage of an adjacent interval. In some implementations, the artefact or off-wrist sleep stage intervals may be re-classified, at least for the purposes of displaying the enhanced hypnogram, as having the sleep stage (awake or non-awake) of an adjacent time interval. In yet further implementations, the artefact and/or off-wrist sleep stages may have their own elevation level(s) in the enhanced hypnogram to allow them to be differentiated from the other sleep stages that may be presented. In such cases, the artefact and/or off-wrist sleep stages may be portrayed in a manner similar to that used to portray "awake" sleep intervals, e.g., with muted or de-emphasized indicators and with the sleep intervals bracketing those sleep intervals shown as continuous in a non-deemphasized manner (as done with the non-awake sleep stage intervals in the enhanced hypnogram example that is depicted). Alternatively, the artefact and/or off-wrist sleep stages may be portrayed in the same manner as non-awake sleep intervals are.

It is to be understood that the phrase "one or more consecutive time intervals," as used herein, is not only inclusive of instances in which there are multiple time intervals, but is also inclusive of instances in which there is a single time interval (and thus technically no other time interval that would be considered to be "consecutive" with that single time interval). Put another way, the phrase "one or more consecutive time intervals" should be understood to mean "a single time interval or two or more consecutive time intervals." Similarly, the phrase "for each <item> of the one or more <items>," if used herein, should be understood to be inclusive of both a single-item group and multiple-item groups, i.e., the phrase "for . . . each" is used in the sense that it is used in programming languages to refer to each item of whatever population of items is referenced. For example, if the population of items referenced is a single item, then "each" would refer to only that single item (despite the fact that dictionary definitions of "each" frequently define the term to refer to "every one of two or more things") and would not imply that there must be at least two of those items.

For example, if the designated threshold is 3 minutes, and a series of 10 time intervals as laid out in the table below are analyzed, a first display time interval "A" may be defined to include interval 1, with a duration of 4 minutes, and may be associated with an "awake" sleep stage. A second display time interval "B" may be defined to include intervals 2-6, as time intervals 2, 4, and 6 are all associated with the "light" sleep stage and are separated from one another only by time intervals 3 and 5, which are both associated with the "awake" sleep stage and have durations of less than the first threshold. A third display time interval "C" may be defined to include time interval 7, which is associated with the "awake" sleep stage and has a duration greater than the first threshold; the third display time interval "C" is associated with the "awake" sleep stage. Finally, a fourth display time interval "D" may be defined to include the time intervals 8-10. The time intervals 8 and 10 are associated with the "light" sleep stage, and are separated by time interval 9, which has a duration less than the first threshold and is associated with the "awake" sleep stage.

| Time Interval | Duration (minutes) | Sleep Stage | Display Time Interval | Display Time Interval Sleep Stage |
|---|---|---|---|---|
| 1 | 4.0 | Awake | A | Wake |
| 2 | 11.0 | Light | B | Light |
| 3 | 1.0 | Awake | | |
| 4 | 4.0 | Light | | |
| 5 | 0.5 | Awake | | |
| 6 | 16.0 | Light | | |
| 7 | 4.0 | Awake | C | Wake |
| 8 | 6.0 | Light | D | Light |
| 9 | 2.5 | Awake | | |
| 10 | 12.0 | Light | | |

In block 2606, a hypnogram may be caused to be generated on a display. The hypnogram may display horizontally extending graphical elements that correspond to the display time intervals, as shown in FIG. 25. In some embodiments, each of the horizontally extending graphical elements may be linked to neighboring horizontally extending graphical elements by vertical lines or risers. In additional to the graphical elements corresponding to the display time intervals, the hypnogram may also display horizontally extending graphical elements corresponding to the time intervals having an "awake" sleep stage and a duration less than the first threshold. These additional graphical elements may be displayed in a less noticeable manner, e.g., a lighter color or faded out, as compared with the graphical elements used to represent the display time intervals.

Figure 27:
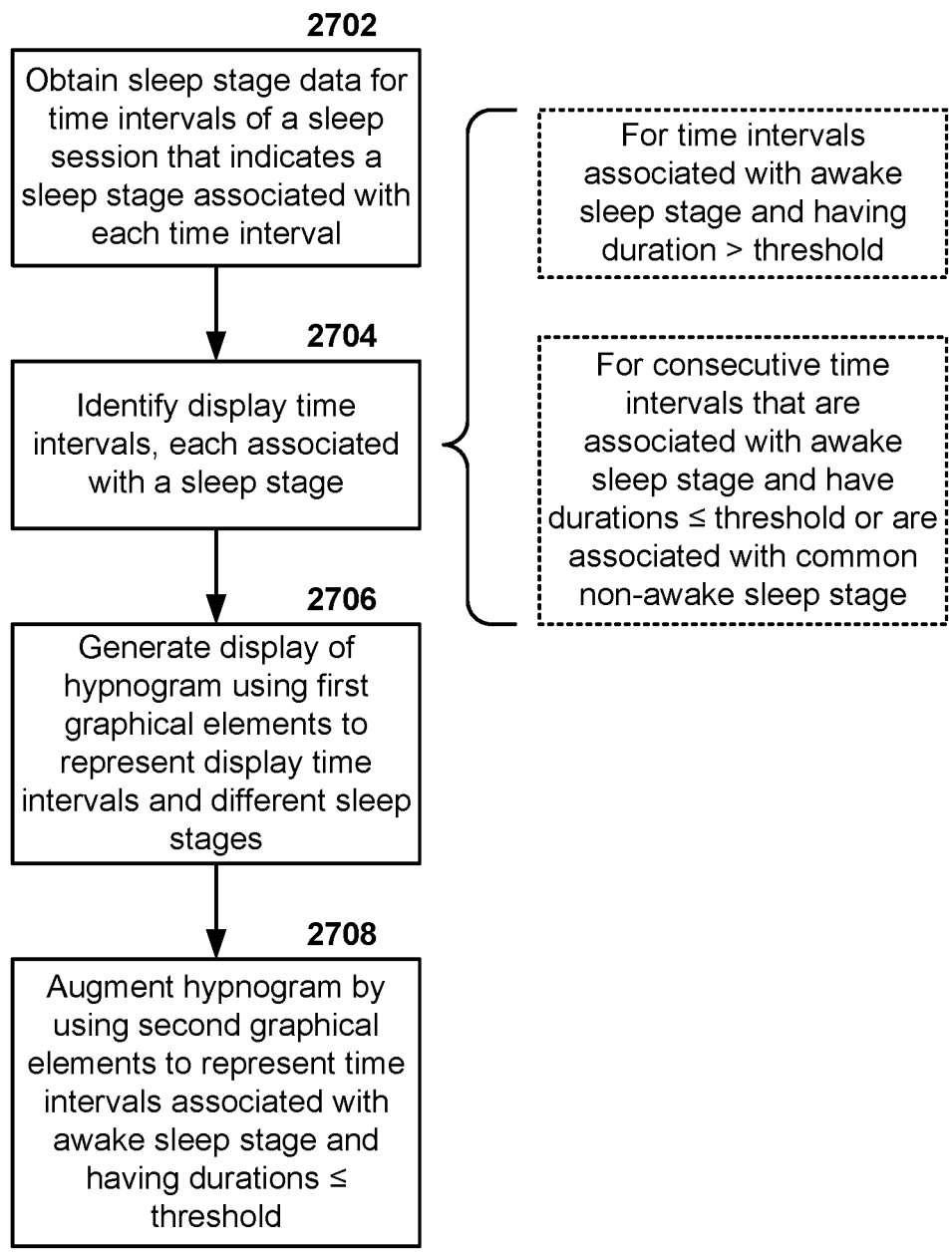
FIG. 27 depicts another technique for producing an enhanced hypnogram.

FIG. 27 depicts another technique for producing an enhanced hypnogram. Blocks 2702-2706 correspond with blocks 2602-2606, and the discussion above for blocks 2602-2606 may be referred to for details of these operations. In the technique of FIG. 27, however, the graphical elements representing the time intervals associated with the "awake" sleep stage and having a duration less than the first threshold may have vertical extension lines that span between the ends of these graphical elements and the graphical element(s) representing the display time intervals and located directly beneath (or above, if the hypnogram has the "awake" sleep stage located beneath the other sleep stages) these ends of the graphical elements representing the time intervals.

As is readily apparent from the above discussion, the sleep stage data for a person's sleep session, such as each time interval during the sleep session when the person was in a particular sleep stage, may be presented to the user using a number of graphical user interfaces. While the user interfaces in question have been described using examples that are formatted for display on a secondary device like a smart phone, such user interfaces may also be arranged for display on a computer monitor or, in some embodiments, on the display of the wearable device (if the wearable device includes a display). The various graphical elements used in the user interfaces may, in some embodiments, be separated from one another and shown on different user interface display pages, e.g., if the user interface is presented on a wearable device, there may be one user interface display page that shows a percentile breakdown, such as the percentile breakdown 2024 in FIG. 20, and another user interface display page that shows a hypnogram, such as the hypnogram 2026. In such cases, the user may navigate between the two pages, but the user interface may not be configured to show both elements on the same user interface display page. However, as discussed earlier, in other embodiments, such elements may be presented on the same user interface display page, and the user interface display page may be scrollable so that only a portion is visible at any one time.

The data and processing that are used to customize and populate the user interfaces discussed herein may, as discussed earlier herein, occur at a variety of different locations. In general, the starting point of such data processing will always be the wearable device, as it is the source of the sensor data that will be used by the classifier to classify time intervals during a sleep session. However, once such sensor data is collected, then the remaining processing may be performed at any of a variety of different locations, e.g., by the wearable device, by a secondary device, by a backend system, etc. For example, the wearable device may perform data collection and some or all of the feature extraction, the secondary device or the backend system may provide the classifier functionality, and the secondary device may present the graphical user interface and perform various operations associated therewith. Other permutations are possible as well.

Data Compression

Many of the features that are extracted from the pulse-related data for use with the classifier may be based on the inter-beat interval durations for each time interval that is to be classified. In many embodiments, these inter-beat interval durations must be stored for some period of time in the wearable device in order to later analyze the inter-beat interval durations to extract further pulse data features. Such later analysis may be performed by the wearable device, but may alternatively be performed by the secondary device or the backend system. Regardless, a significant amount of inter-beat interval duration information may need to be stored by the wearable device. This can present storage and data transmission complications in such devices, as they may have limited memory and/or communications bandwidth. Moreover, battery life may be negatively impacted if the wearable device transmits the inter-beat interval information in uncompressed form. In order to address such concerns, some embodiments may apply one or more data compression techniques, as discussed in more detail below, to the inter-beat interval data prior to storage and/or transmission. While the techniques discussed below are presented with respect to compressing inter-beat interval information, these same techniques may also be generally applied to any time-series data generated based on sensor data from the wearable device, such as motion data, respiration rate data, etc.

Figure 28:
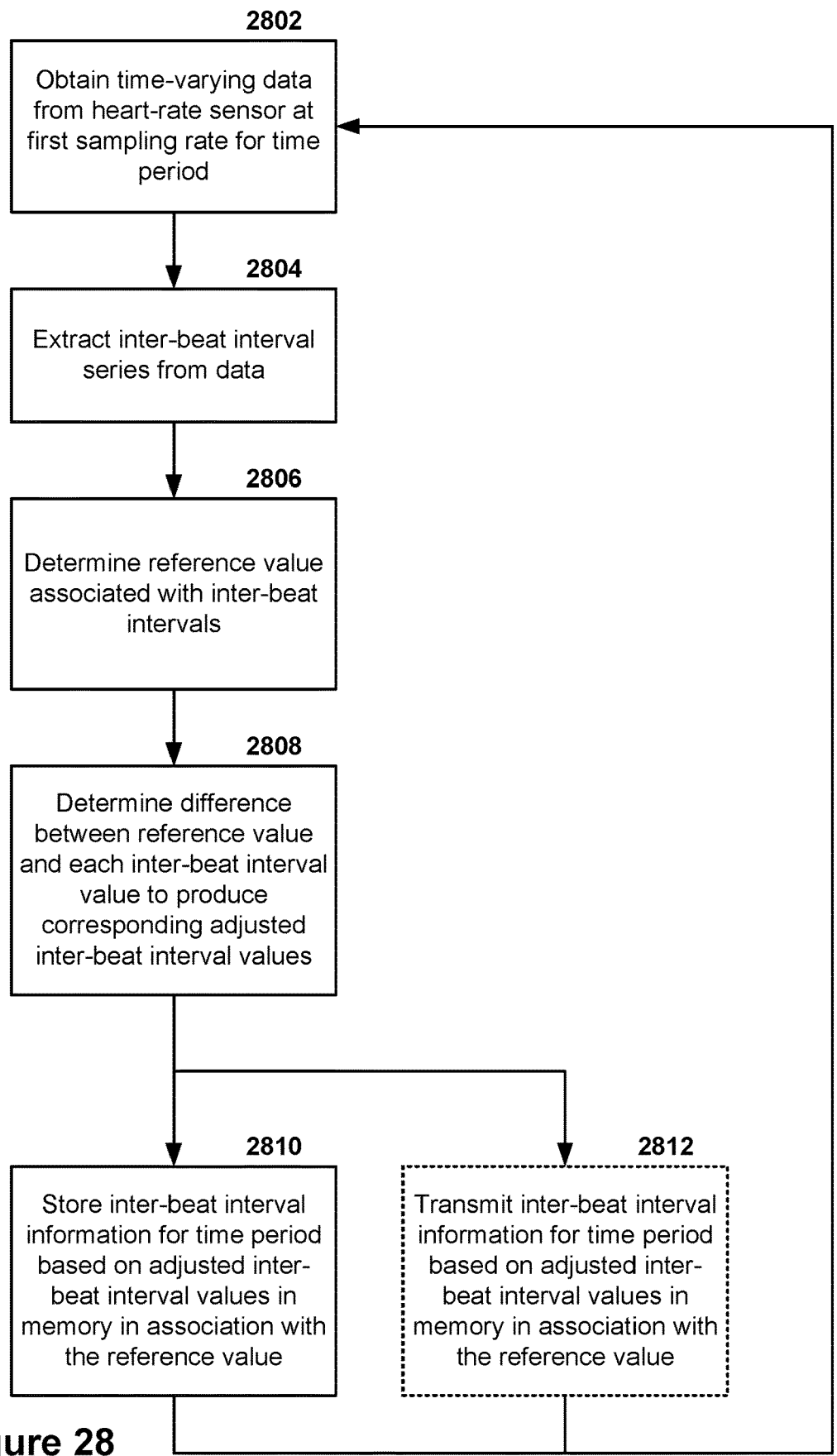
FIG. 28 depicts a flow diagram of a technique for compressing inter-beat interval data.

FIG. 28 depicts a flow diagram of a technique for compressing inter-beat interval data. In block 2802, time-varying data from a heart-rate sensor may be obtained at a first sampling rate for a time period. The first sampling rate, for example, may be on the order of approximately 1 kHz, although other sampling rates are possible as well. In block 2804, the time-varying data may be analyzed to identify inter-beat intervals, e.g., by identifying peaks in the time-varying data and measuring the distance between each pair of neighboring peaks. The resulting inter-beat interval values may then be stored as an inter-beat interval series. Inter-beat intervals can be assumed to be limited in range—a typical human resting heart rate (as would generally be observed during sleep monitoring) is between 60 and 100 beats per minute, although heart rates as low as 40 beats per minute may be observed in some athletes due to their peak physical condition. Thus, the inter-beat intervals that may be expected for typical subjects when extracting the inter-beat interval series may generally be between 1.5 seconds and 0.6 seconds. However, in order to capture outliers or atypically slow heart rates, it may be desirable to store inter-beat interval durations as high as 2 seconds. Under such assumptions, and using a 1 kHz sampling rate, the inter-beat interval durations may be represented, in their raw form, as 11-bit values (2 seconds at 1 kHz sampling rate=2000 counts 2048 bits=$2^{11}$). It is to be understood that lower sampling rates may be used as well, e.g., sampling rates as low as 100 Hz or even 25 Hz may be interpolated to a higher count resolution with reasonable confidence due to the band-limited nature of a heartbeat signal—this interpolated count value may then be the value that is stored, in addition to or in place of the raw signal count from the sensor. Thus, storing the raw inter-beat interval series may require reserving a large number of 11-bit memory blocks, which may consume limited memory resources (especially if the inter-beat interval series for every time interval during one or more sleep sessions is stored—this would require an 11-bit value to be stored for every heartbeat that occurred during each sleep session; an average sleep session might have on the order of 30,000 such data points). Moreover, as discussed above, transmitting such data to a secondary device may, due to the size of the data being transmitted, contribute significantly to battery charge depletion.

In order to decrease the memory and/or transmission footprint of the inter-beat interval series, the inter-beat interval series data may be analyzed in block 2806 in order to determine a reference value that is associated with the inter-beat interval values for the time period in question. The reference value may be determined in a number of ways, although perhaps the most useful approach is to use the average inter-beat interval value as the reference value, i.e., the arithmetic mean of the inter-beat interval values for the time period. Other possibilities include other measures of central tendency (in addition to the arithmetic mean), such as the median inter-beat interval value or the mode of the inter-beat interval values, or, generally speaking, any value between the minimum and maximum inter-beat interval values. The average, however, is perhaps easiest to calculate and, as will be seen in a later-discussed example, provides some additional benefits as compared with other types of reference values.

Once the reference value for the time period has been determined, then the difference between each inter-beat interval value in the time period and the reference value may be determined and used to create a new series of adjusted inter-beat interval values. Thus, for example, if the reference value is 1 second (or 1000 counts) and an example inter-beat interval is 1.042 seconds (or 1042 counts) in length, then the difference between them would be 0.042 seconds (or 42 counts). An example table for a series of five inter-beat intervals is provided below—as can be seen, the adjusted inter-beat interval values require a much smaller bit size in order to be stored or transmitted.

| Inter-beat Interval Value (s) | Counts | Reference Value (counts) | Adjusted Inter-beat Interval Value (counts) |
|---|---|---|---|
| 1.042 | 1042 | 1000 | 42 |
| 0.971 | 971 | 1000 | −29 |
| 1.085 | 1085 | 1000 | 15 |
| 1.013 | 1013 | 1000 | 13 |
| 0.999 | 999 | 1000 | −1 |

In block 2810, the adjusted inter-beat interval series for the time period, as well as the reference value for the time period, may be stored for later reference. Additionally or alternatively, in block 2812, the same information may be transmitted to a remote device, e.g., a secondary device, for storage and/or analysis by the remote device. The technique may then return to block 2802 for processing of additional time periods.

The technique of FIG. 28 generally allows for lossless (or near-lossless) compression of the inter-beat interval series since a person's heart rate generally has limited variability, e.g., the heart rate will generally not fluctuate beyond a certain level with respect to the person's average heart rate. For example, a person's heart rate may fluctuate as much as ±30% of their average heart rate, but fluctuations beyond that range may be rare or even non-existent. The raw inter-beat interval series, therefore, may include leading bit values that would, in practice, almost never fluctuate due to the limited range of fluctuation in the inter-beat interval values. These leading bit values would, however, be repeated for every inter-beat interval value that was stored. The reference value, in effect, removes this repeating element from the stored data and allows it to be stored once, separately from the adjusted inter-beat interval values. The adjusted inter-beat interval values may later be converted back into their original values by adding them to the reference value. In some embodiments, the adjusted inter-beat interval series may be stored as a representation having a pre-defined bit size, e.g., a 9-bit representation. In such cases, adjusted inter-beat intervals that exceed the available, pre-defined bit size may be capped at the maximum or minimum value supported by the pre-defined bit size. For example, if a 9-bit representation is used, this may allow for adjusted inter-beat intervals of between −256 and +255; if an adjusted inter-beat interval value of 260 is encountered, then it may be stored simply as the maximum value permitted by the 9-bit representation, i.e., 255. In such cases, there will be some loss of resolution in the outlying data due to this truncation when the adjusted inter-beat intervals are transformed back into the actual inter-beat interval values using the reference value. However, such loss may be minimal and not have a significant effect on the overall usefulness of the inter-beat interval series being stored.

The technique of FIG. 28 may be used to significantly reduce the data storage or transmission needs associated with handling inter-beat interval series—for example, an 11-bit representation may be replaced by a 9-bit representation, which is a nearly 20% improvement in data storage or transmission efficiency.

Figure 29:
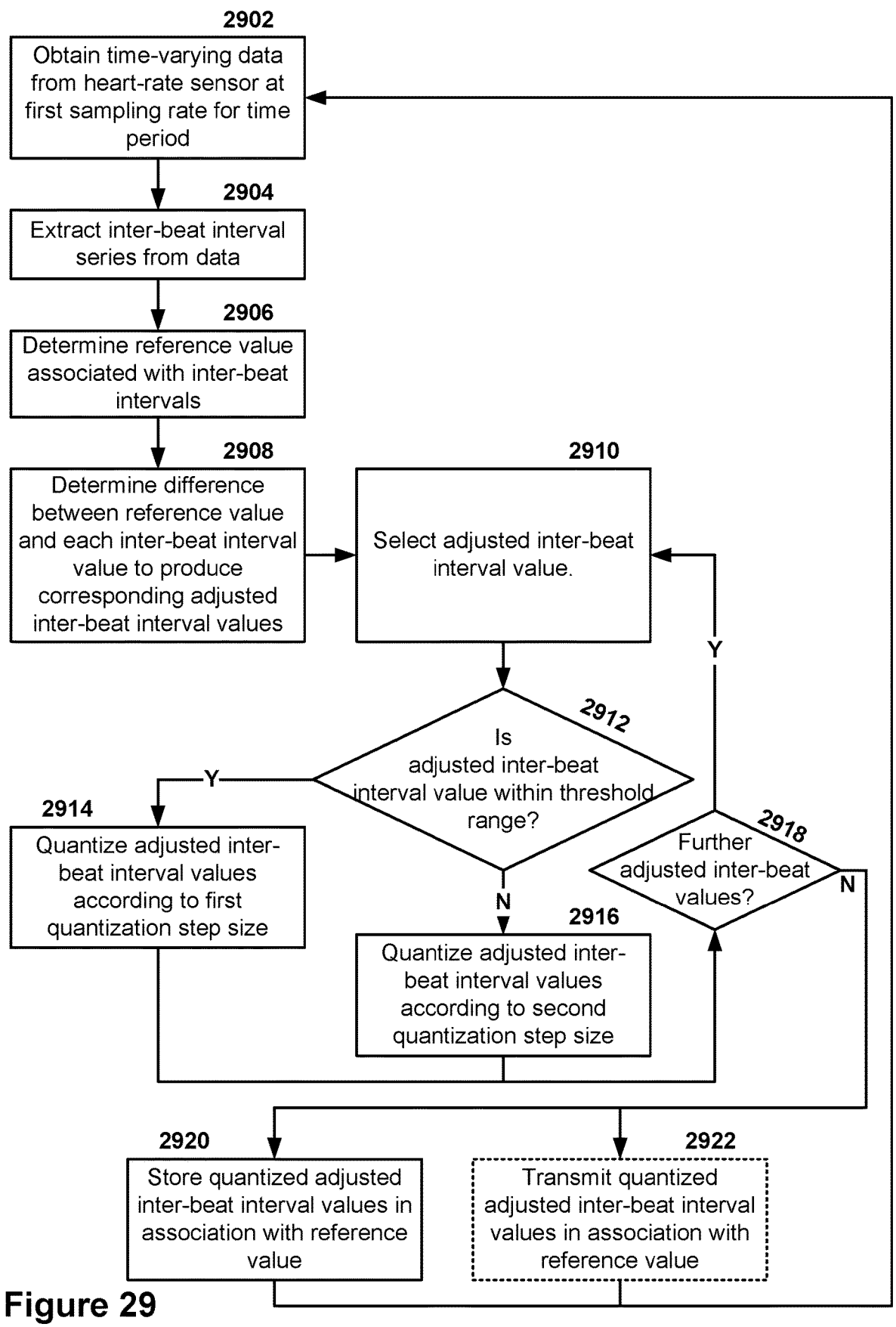
FIG. 29 depicts a flow diagram for a further technique for compressing inter-beat interval data.

A further technique for compressing inter-beat interval data is discussed with reference to FIG. 29, which is a flow diagram for such a technique. In FIG. 29, blocks 2902 through 2908 correspond with blocks 2802 through 2808 of FIG. 28, and the earlier description of those blocks is equally applicable with reference to FIG. 29. However, after the difference between the reference value (which, in this technique, is calculated as the average of the inter-beat interval values for the time period being compressed) and each inter-beat interval value is determined in block 2908, the technique may proceed to block 2910, where one of the adjusted inter-beat intervals may be selected before proceeding to block 2912, where a determination may be made as to whether the selected adjusted inter-beat interval value is within a first threshold range. For example, the first threshold range may be −96 to +95 milliseconds (spanning 192 counts), and adjusted inter-beat interval values of −96 counts to +95 counts may be considered to be within the first threshold range. If it is determined in block 2912 that the selected adjusted inter-beat interval value is within the first threshold range, then the technique may proceed to block 2914, in which the selected adjusted inter-beat interval value may be quantized according to a first quantization step size, e.g., 4 milliseconds. In such quantization, the inter-beat intervals may be mapped into "bins" according to a quantization step size in order to reduce the number of discrete values in the dataset. For example, if the quantization step size is 4 milliseconds (or, in this example, 4 counts), then the range of the data being quantized according to that quantization step size may be subdivided into bins that each have a size commensurate with the quantization step size. Thus, if one were to quantize values ranging from 1 to 20 according to a quantization step size of 4, this would map the values 1-4 to bin 1, values 5-8 to bin 2, values 9-12 to bin 3, and so forth. In this example, the quantization step size of 4 reduces the range of potential values by 75%. If it is determined in block 2912 that the selected adjusted inter-beat interval value is not within the first threshold range, then the technique may instead proceed to block 2916, in which the selected adjusted inter-beat interval value may be quantized according to a second quantization step size, e.g., 20 milliseconds, larger than the first quantization step size. Since the inter-beat interval values for a person's heart rate typically exhibit a Gaussian distribution, this has the effect of preserving resolution for the bulk of the inter-beat interval values, which will be clustered around the average/reference value. Outlier inter-beat interval values may be quantized at a coarser resolution, although there will be far fewer of these as compared with the inter-beat interval values quantized at the finer resolution.

The threshold range may, for each time period having adjusted inter-beat interval values being quantized, be set to a fixed range or may be dynamically adjusted based on the adjusted inter-beat interval values being quantized. For example, in some embodiments, the same fixed range may be used as the threshold range for every time period for which adjusted inter-beat interval values are quantized. In other embodiments, however, the threshold range may be re-determined for each time period based on the values of the adjusted inter-beat intervals being quantized. For example, the threshold range may be re-set for each time period such that a given percentage (or at least a given percentage), e.g., at least 80%, of the adjusted inter-beat interval values falls within the threshold range. In some such embodiments, the quantization step size may be adjusted to maintain the same total number of quantization bins overall and within/without the threshold range.

In block 2918, a determination may be made as to whether there are further inter-beat interval values in the current time period needing quantization—if so, the technique returns to block 2910, and a new inter-beat interval value in the inter-beat interval value series may be quantized. If not, then the technique may proceed to blocks 2920 and/or 2922, in which the quantized adjusted inter-beat interval values for the time period being analyzed may be stored or transmitted in association with the reference value associated with that time period. The technique may then return to block 2902 for processing of another time period. Because of the quantization scheme discussed above, the bit values used to represent the inter-beat interval values may be further decreased. For example, if the 4 ms/20 ms and first threshold range of −96 to +95 counts example quantization scheme discussed earlier is used, in conjunction with the conversion from an 11-bit value to a 9-bit value achieved through use of the reference value (see blocks 2906 and 2908), the 9-bit value may be further reduced to, for example, a 6 bit value. This is because there may be only 64 total quantization levels in the quantized data—48 in which the quantization step size is 4 ms and 16 in which the quantization step size is 20 ms.

It is to be understood that additional quantization levels may be used, as desired, in order to provide a three-, four-, or N-level quantization scheme—each quantization level may be associated with a different threshold range. It is also to be understood that a single quantization level may be used throughout, although such embodiments may not provide nearly as much data compression (or, if they do, the data that is compressed may be decreased significantly in quality due to the application of a large quantization step size to the bulk of the data).

It is also to be understood that while in this examples discussed above, the quantization occurs after the determination of the adjusted inter-beat interval values, it is also possible to perform quantization on the unadjusted inter-beat interval values, e.g., prior to the operations of block 2906. In such embodiments, the quantization may only be single-step quantization, as the first threshold range of the multi-step quantization technique is centered on the reference value, which is not applicable to the data until after block 2906.

The techniques above, as can be seen, can result in a reduction of nearly 50% in the bit cost to store an inter-beat interval value series, which can significantly reduce data storage and transmission resource costs.

CONCLUSION

As is evident from the above discussion, the techniques, systems, and apparatuses discussed herein may be utilized to facilitate sleep stage tracking using a wearable device. The techniques discussed herein may be practiced as methods, or may be embodied in the form of computer-readable instructions stored on one or more memory devices for controlling one or more processors to perform the techniques discussed herein. Such memory devices may be part or parts of an apparatus or system, e.g., part of a wearable device, secondary device, and/or backend system, or may be free-standing memory devices, e.g., a disk or flash memory device that may be connected with a computing device in order to copy such instructions to the computing device or execute the instructions from the free-standing memory device using the computing device.

Importantly, the concepts discussed herein are not limited to any single aspect or implementation discussed herein, nor to any combinations and/or permutations of such aspects and/or implementations. Moreover, each of the aspects of the present invention, and/or implementations thereof, may be employed alone or in combination with one or more of the other aspects and/or implementations thereof. For the sake of brevity, many of those permutations and combinations will not be discussed and/or illustrated separately herein.

What is claimed is:

1. A computer-implemented method for labeling stages of sleep, the computer-implemented method comprising:
   executing instructions stored within a non-transitory, machine-readable storage medium that is operatively coupled to one or more processors to cause the one or more processors to perform the following operations:
   obtaining, using a wrist-worn device, motion data for a user during a time window in which the user is asleep;
   obtaining, using the wrist-worn device, cardiopulmonary data for the user during the time window;
   processing the motion data and the cardiopulmonary data with a classifier model to generate one or more labels, each of the one or more labels generated for a corresponding time period within the time window,
   each label indicating the user is awake or in one of a plurality of different stages of sleep during the corresponding time period,
   extracting a first feature from the motion data for the user;
   extracting a second feature from the cardiopulmonary data or from inter-beat intervals for the user,
   wherein the second feature comprises at least one of a variability of a de-trended respiration rate, an inter-percentile spread of a heart rate, and a normalized de-trended heart rate,
   and wherein the processing of the motion data and the cardiopulmonary data with the classifier model includes processing the first feature and the second feature to generate the one or more labels;
   and displaying, on a graphical user interface, the one or more labels;
   where the displaying of the one or more labels includes a graphic report of at least one time period and a label that correspond to the time period.

2. The computer-implemented method of claim 1, wherein:
   the obtaining of the motion data for the user includes obtaining the motion data from a first sensor;
   and the obtaining of the cardiopulmonary data for the user includes obtaining the cardiopulmonary data from a second sensor that is different than the first sensor.

3. The computer-implemented method of claim 2, wherein the first sensor includes an accelerometer and the second sensor includes an optical sensor.

4. The computer-implemented method of claim 3, wherein the optical sensor includes a photoplethysmogram (PPG) sensor.

5. The computer-implemented method of claim 1, wherein the first feature includes an amount of time that has lapsed since the motion data last indicated a threshold amount of motion by the user.

6. The computer-implemented method of claim 1, wherein the second feature includes a difference between a minimum heart rate of the user during a threshold amount of time and a maximum heart rate of the user during the threshold amount of time.

7. The computer-implemented method of claim 1, wherein a third feature includes:
   a variability of an envelope of inter-beat intervals, or a cross-correlation of each pulse shape of one or more pulse shapes in the cardiopulmonary data with a previous pulse shape in the cardiopulmonary data,
   wherein the pulse shapes are normalized to a common duration prior to the cross-correlation.

8. The computer-implemented method of claim 1, wherein the plurality of different stages of sleep include a light sleep stage, a deep sleep stage, and a rapid eye movement (REM) sleep stage.

9. The computer-implemented method of claim 1, wherein the classifier model includes a random forest classifier or a linear discriminant classifier model.

10. A system for labeling stages of sleep, the system comprising:
    a plurality of sensors within a wrist-worn device;
    one or more processors; and a non-transitory, machine-readable storage medium operatively coupled to the one or more processors and having stored therein instructions that, when executed, cause the one or more processors to perform operations, the operations including:

obtaining, via one or more sensors of the plurality of sensors, motion data for a user during a time window in which the user is asleep and wearing the wrist-worn device;

obtaining, via one or more sensors of the plurality of sensors, cardiopulmonary data for the user during the time window;

and processing the motion data and the cardiopulmonary data with a classifier model to generate a one or more labels, each of the one or more labels generated for a corresponding time period within the time window, each label indicating the user is awake or in one of a plurality of different stages of sleep during the corresponding time period, extracting a first feature from the motion data for the user;

extracting a second feature from the cardiopulmonary data or from inter-beat intervals for the user, wherein the second feature comprises at least one of a variability of a de-trended respiration rate, an inter-percentile spread of a heart rate, and a normalized de-trended heart rate, and wherein the processing of the motion data and the cardiopulmonary data with the classifier model includes processing the first feature and the second feature to generate the one or more labels;

and displaying, on a graphical user interface, the one or more labels;

where the displaying of the one or more labels includes a graphic report of at least one time period and a label that correspond to the time period.

11. The system of claim 10, wherein:

the obtaining of the motion data for the user includes obtaining, via a first sensor of the plurality of sensors, the motion data;

and the obtaining of the cardiopulmonary data includes obtaining, via a second sensor of the plurality of sensors, the cardiopulmonary data, the second sensor being different than the first sensor.

12. The system of claim 11, wherein:
the first sensor includes an accelerometer;
and the second sensor includes an optical sensor.

13. The system of claim 10, wherein the first feature includes an amount of time that has lapsed since the motion data last indicated a threshold amount of motion by the user.

14. The system of claim 10, wherein the second feature includes a difference between a minimum heart rate of the user during a threshold amount of time and a maximum heart rate of the user during the threshold amount of time.

15. The system of claim 10, wherein the plurality of different stages of sleep include a light sleep stage, a deep sleep stage, and a rapid eye movement (REM) sleep stage.

16. The system of claim 10, wherein the classifier model includes a random forest classifier or a linear discriminant classifier model.

17. The system of claim 10, wherein processing the motion data and the cardiopulmonary data using the classifier model includes:

determining a first confidence score for the user being awake during one or more time periods;

and determining a second confidence score for the user being in a first stage of the plurality of different stages of sleep during the one or more time periods;

determining a third confidence score for the user being a second stage of the plurality of different sleep stages during the one or more time periods;

and labeling the one or more time periods with a label corresponding to a highest of the first confidence score, the second confidence score, and the third confidence score.

18. The computer-implemented method of claim 1, wherein the classifier model is trained using sleep stage classifications determined by a human for one or more sleep study subjects and based on motion data for the one or more sleep study subjects.

19. The system of claim 10, wherein the classifier model is trained using sleep stage classifications determined by a human for one or more sleep study subjects and based on motion data for the one or more sleep study subjects and cardiopulmonary data for the one or more sleep study subjects.

* * * * *